US006774082B2

(12) United States Patent
Bruening et al.

(10) Patent No.: US 6,774,082 B2
(45) Date of Patent: Aug. 10, 2004

(54) COMPOSITIONS FOR SEPARATING HETEROCYCLIC AROMATIC AMINE BASES, NUCLEOSIDES, NUCLEOTIDES, AND NUCLEOTIDE SEQUENCES

(75) Inventors: Ronald L. Bruening, American Fork, UT (US); Krzysztof E. Krakowiak, Provo, UT (US); David Vernell Dearden, Mapleton, UT (US); Barry L. Haymore, St. Louis, MO (US); Milton Bruening, Springville, UT (US)

(73) Assignee: IBC Advanced Technologies, Inc., American Pork, UT (US)

( * ) Notice: Subject to any disclaimer, the term of this patent is extended or adjusted under 35 U.S.C. 154(b) by 149 days.

(21) Appl. No.: 10/144,245

(22) Filed: May 10, 2002

(65) Prior Publication Data

US 2003/0050458 A1 Mar. 13, 2003

Related U.S. Application Data

(60) Provisional application No. 60/290,577, filed on May 11, 2001.

(51) Int. Cl.[7] ............................................. B01J 20/22

(52) U.S. Cl. ....................................... 502/401; 502/403

(58) Field of Search ................................ 502/401, 402, 502/403

(56) References Cited

U.S. PATENT DOCUMENTS

| | | | |
|---|---|---|---|
| 4,943,375 A | 7/1990 | Bradshaw et al. |
| 4,952,321 A | 8/1990 | Bradshaw et al. |
| 4,959,153 A | 9/1990 | Bradshaw et al. |
| 4,960,882 A | 10/1990 | Bradshaw et al. |
| 5,039,419 A | 8/1991 | Bradshaw et al. |
| 5,071,819 A | 12/1991 | Tarbet et al. |
| 5,078,978 A | 1/1992 | Tarbet et al. |
| 5,084,430 A | 1/1992 | Tarbet et al. |
| 5,173,470 A | 12/1992 | Bruening et al. |
| 5,179,213 A | 1/1993 | Bradshaw et al. |
| 5,182,251 A | 1/1993 | Bruening et al. |
| 5,190,661 A | 3/1993 | Bruening et al. |
| 5,244,856 A | 9/1993 | Bruening et al. |
| 5,273,660 A | 12/1993 | Breuning et al. |
| 5,393,892 A | 2/1995 | Krakowiak et al. |

*Primary Examiner*—Stanley S. Silverman
*Assistant Examiner*—Edward M. Johnson
(74) *Attorney, Agent, or Firm*—Thorpe North & Western, LLP

(57) ABSTRACT

The compositions of the present invention comprise one or more palladium bound ligands that are covalently bonded to inorganic or organic solid supports. These palladium bound ligands bonded to solid supports can be used for single heterocyclic amine base separation, or can be used to separate nucleotide chain containing specific sequences from other nucleotides or nucleotide chains. In one aspect of the invention, each ligand present is individually complexed to a single Pd(II) ion. If there are from 2 to 4 ligands present in the composition, then each ligand present must be separated from the other ligands by at least 3 atoms, preferably from 3 to 20 carbon atoms or equivalent spacing.

49 Claims, 1 Drawing Sheet

US 6,774,082 B2

COMPOSITIONS FOR SEPARATING HETEROCYCLIC AROMATIC AMINE BASES, NUCLEOSIDES, NUCLEOTIDES, AND NUCLEOTIDE SEQUENCES

This application claims the benefit of U.S. Provisional Application No. 60/290,577 filed on May 11, 2001.

FIELD OF THE INVENTION

The present invention is drawn to compositions and methods for separating desired heterocyclic aromatic amine bases, nucleosides, nucleotides, or sequences of DNA using separation techniques, preferably non-chromatographic separation techniques.

BACKGROUND OF THE INVENTION

Deoxyribonucleic Acid (DNA) is generally comprised of four different types of nucleotides. These nucleotides are comprised of three components: (1) heterocyclic aromatic amine base; (2) 2-deoxy-D-ribose; and (3) phosphoric acid. The bases are generally from two N-heterocyclic categories, namely pyrimidine and purine, the general structures of which are shown below; respectively.

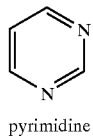   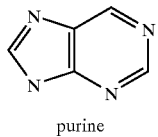

pyrimidine              purine

In DNA, the two pyrimidine-type bases are cytosine (C) and thymine (T). Additionally with respect to DNA, the two purine-type bases are adenine (A) and guanine (G).

Likewise, Ribonucleic Acid (RNA) is similar to DNA in that they too are comprised of long, unbranched chains of nucleotides joined by phosphodiester bonds between the 3'-hydroxyl of one pentose and the 5'-hydroxyl of an adjacent pentose. However, there are three main differences between DNA and RNA including: (1) the pentose unit in the RNA is D-ribose rather than 2-deoxy-D-ribose; (2) the pyrimidine base found in RNA is uracil (U) rather than thymine (T); and (3) RNA is single stranded rather than double stranded. The three pyrimidine-type heterocyclic aromatic amine bases found in DNA and RNA are shown below:

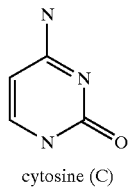   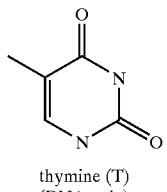   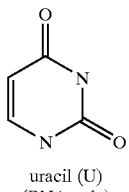

cytosine (C)    thymine (T)      uracil (U)
                (DNA only)       (RNA only)

The two purine-type heterocyclic aromatic amine bases found in both DNA and RNA are shown below.

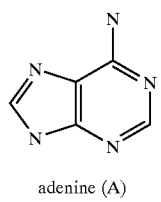   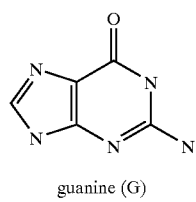

adenine (A)           guanine (G)

In the case of DNA, a nucleoside is a glycoside in which nitrogen 9 of a purine or nitrogen I of a pyrimidine base is bonded to 2-deoxy-D-ribose. An example is shown below.

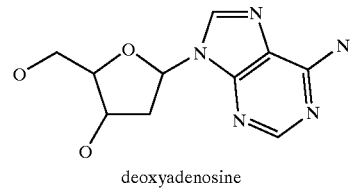

deoxyadenosine

Further, with respect to DNA, a nucleotide is a nucleoside monophosphate ester in which a molecule of phosphoric acid is esterified with a free hydroxy group of 2-deoxy-D-ribose. An example is shown below.

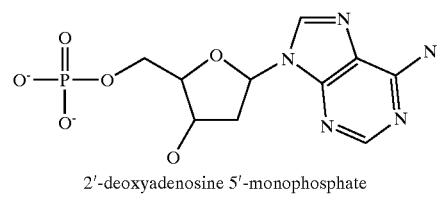

2'-deoxyadenosine 5'-monophosphate

In the prior art, the separation of nucleotides has primarily been accomplished by utilizing separation devices that selectively bind to the phosphoric acid portion, or the 2-deoxy-D-ribose portion of the DNA. For example, ligand complexes containing zinc, copper, and nickel have been used to selectively bind the phosphoric acid portion of a nucleotide. Though the selectivity of such compounds has been somewhat effective in separating nucleotides from other impurities, these systems and methods do not exhibit high selectivity properties when the desire is to separate one nucleotide from another, e.g., A from T. With these systems, if the desired heterocyclic amine is merely in the form of a nucleoside, there is no phosphoric acid portion present and the separation cannot occur. Additionally, with such compositions, lone heterocyclic aromatic amine bases cannot be separated without being present as an intact nucleotide.

SUMMARY OF THE INVENTION

The compositions and methods of the present invention comprise one or more palladium bound ligands that are covalently bonded to inorganic or organic solid supports. These palladium bound ligands bonded to solid supports can be used to separate single heterocyclic amine bases, nucleosides, nucleotides, or nucleotide chains containing specific sequences from other non-desired molecular units present. In one aspect of the invention, each ligand present as part of the composition is individually complexed to a single Pd(II) ion. If there are from 2 to 4 ligands present on a single composition, then each ligand present can be bound to a palladium ion and each ligand should be separated from the other ligands by at least 3 atoms, preferably from 3 to 20 carbon atoms or an equivalent spacer chain.

BRIEF DESCRIPTION OF THE DRAWINGS

In the accompanying drawings which illustrate embodiments of the invention.

DETAILED DESCRIPTION OF THE INVENTION

Figure 1:
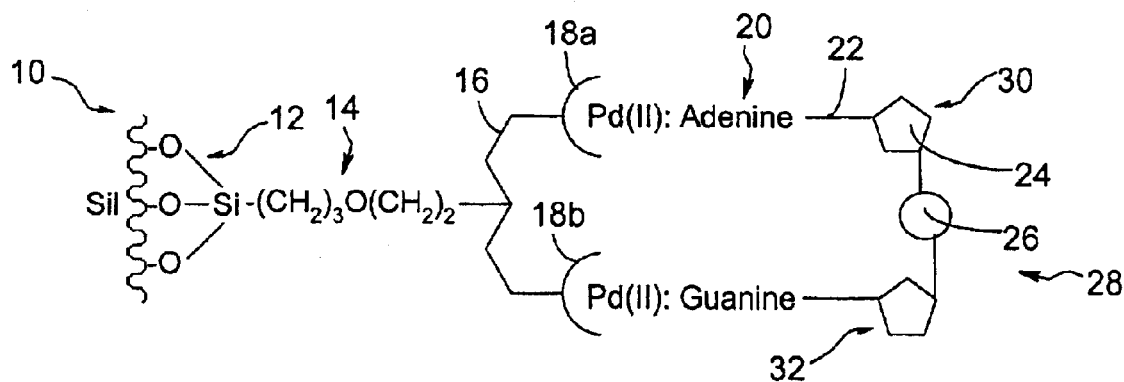
FIG. 1 is a schematic representation of an embodiment of the present invention wherein nucleotide sequence A-G is selected.

Before the present invention is disclosed and described, it is to be understood that this invention is not limited to the particular process steps and materials disclosed herein because such process steps and materials may vary somewhat. It is also to be understood that the terminology used herein is used for the purpose of describing particular embodiments only. The terms are not intended to be limiting because the scope of the present invention is intended to be limited only by the appended claims and equivalents thereof.

It is noted that, as used in this specification and the appended claims, the singular forms "a," "an," and "the" include plural referents unless the content clearly dictates otherwise.

"Lower alkyl" includes straight chain alkyl groups having from 1 to 10 atoms, and branched chain alkyl groups having from 3 to 10 carbon atoms.

"Heterocyclic aromatic amine bases" include the five bases that are present in RNA and DNA, namely: cytosine (C), thymine (T), uracil (U), adenine (A), and guanine (G).

"Nucleoside" is a glycoside between a nitrogen of the heterocyclic aromatic amine base and 2-deoxy-D-ribose. For example, adenine bonded to 2-deoxy-D-ribose is known as deoxyadenosine.

"Nucleotide" is a nucleoside monophosphate ester. For example, the nucleoside deoxyadenosine can be esterified with a free hydroxy group of the 2-deoxy-D-ribose to become 2'-deoxyadenosine 5'-monophosphate.

"Organic backbone" or "Backbone" refers to an organic chain having from about 3 to 20 atoms, including carbon atoms, that are present to tether multiple ligands to one another. Other constituents that can form part of or be attached to the backbone, other than carbon, include oxygen, sulfur, nitrogen, and the like, as long as such atoms do not substantially interfere with the palladium-bound ligands being supported by the backbone.

"Palladium(II)-bound ligand backbone grouping" shall include from 2 to 4 ligands that are tethered together by an organic backbone. Between each ligand, from about 3 to 20 atoms can be present to appropriately space the ligands from one another. The palladium(II)-bound ligand backbone grouping is typically used when separating nucleotide sequences rather than individual heterocyclic aromatic amine bases.

When referring to a specific purine and pyrimidine ring found in DNA and/or RNA, e.g., cytosine (C), thymine (T), uracil (U), adenine (A), and/or guanine (G), its isolated form as well as its nucleoside and nucleotide forms are included. For example, in the specification and claims where it is stated that a palladium(II)-bound ligand is selective of adenine, or where adenine is bound to a palladium(II)-bound ligand, such a statement shall include not only adenine itself, but deoxyadenosine and 2'-deoxyadenosine 5'-monophosphate. In other words, adenine-containing molecules are included as the selectivity described in the present invention is typically with respect to the adenine-portion of the molecule, as opposed to the 2-deoxy-D-ribose and/or the monophosphate portion of the nucleotide and/or nucleoside.

With these definitions as a reference, a composition for selectively binding a desired nucleotide sequence can comprise from 2 to 4 palladium(II)-bound ligands. The palladium(II)-bound ligands can be tethered together by an organic backbone having from 3 to 20 atoms between each palladium(II)-bound ligand, thereby forming a palladium (II)-bound ligand backbone grouping. The palladium(II)-bound ligand backbone grouping can also be covalently bonded to a solid support, wherein each palladium(II)-bound ligand is independently selective of a desired heterocyclic aromatic amine base of the nucleotide sequence. In an alternative embodiment, an alternative composition can comprise a palladium(II)-bound ligand covalently bonded to a solid support, wherein the palladium(II)-bound ligand is further complexed to a heterocyclic aromatic amine base.

In a further detailed aspect, the compositions of the present invention can comprise one or more ligands that are covalently bonded to an inorganic or organic solid support through a spacer and are represented by Formula 1 as follows:

$$SS\text{-}A\text{-}X\text{-}B_m[L\text{:}Pd(II)]_n \qquad \text{Formula 1}$$

wherein SS is an inorganic or organic solid support, A is a covalent linkage mechanism, X is a spacer grouping, B is an organic backbone, and each L present is a ligand independently selective of a desired heterocyclic aromatic amine base that may be present in a source solution with other undesired heterocyclic aromatic amine bases. As such, n can be an integer from 1 to 4 such that when n is 1, there is one ligand and one Pd(II) ion present; when n is 2, there are two ligands and two Pd(II) ions present; and so forth. In one aspect of the invention, each ligand present is individually complexed to a single Pd(II) ion. When n is 1, m is 0, e.g., there is no backbone B, and spacer grouping X is attached directly to the ligand L. When n is from 2 to 4, m is 1 (denoting a backbone B is present). Though the spacer grouping is shown attached to the organic backbone, it can also be attached directly to the ligand, such as when n is 1, and even sometimes when n is from 2 to 4. For example, the spacer grouping can be attached to a first ligand, and a second (or third or fourth) ligand can be tethered to the first ligand by the organic backbone. If there are from 2 to 4 ligands present in the composition, then each ligand present should be separated from the other ligands by at least 3 atoms of the backbone, preferably from 3 to 20 carbon atoms or equivalent spacer atoms.

The SS-A-X- portion of Formula 1 is well known for use with ion binding ligands. Therefore, when referring to the SS-A-X- portion of the formula, reference will be made to a solid support covalently bonded to a ligand (or palladium (II)-bound ligand), or a ligand covalently bonded to a solid support.

With respect to specific embodiments of the SS-A-X-portion of Formula 1, certain preferred embodiments will be shown and described. These embodiments are not meant to be limiting, as other solid supports and covalent linkage mechanisms may be used with similar success.

In Formula 1, the solid support (SS) is an inorganic and/or organic particulate support material selected from the group consisting of silica, silica gel, silicates, zirconia, titania, alumina, nickel oxide, glass beads, phenolic resins, polystyrenes, agarose, sepharose, and polyacrylates. However, other organic resins or any other hydrophilic organic and/or inorganic support materials meeting the above criteria can also be used.

The use of organic ion binding ligands attached to an SS-A-X- solid support by means of a covalent linkage spacer grouping is illustrated in U.S. Pat. Nos. 4,943,375; 4,952,321; 4,959,153; 4,960,882; 5,039,419; 5,071,819;

5,078,978; 5,084,430; 5,173,470; 5,179,213; 5,182,251; 5,190,661; 5,244,856; 5,273,660; and 5,393,892. These patents, which disclose various spacers that can be used in forming an organic ligand attached to a solid support, are fully incorporated herein by reference.

When the solid support (SS) is an inorganic material such as silica, silica gel, silicates, zirconia, titania, alumina, nickel oxide, or glass beads, the covalent linkage (A) is a silane such that A-X can be represented by Formula 2 as follows:

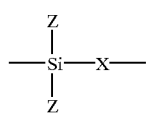

Formula 2 where each Z is independently selected from the group consisting of Cl, Br, I, lower alkyl, lower alkoxy, substituted lower alkyl or substituted lower alkoxy and S (as used herein, lower alkyl or lower alkoxy means a group having 1 to 10 carbon atoms); and X can be, for example, a spacer grouping represented by Formula 3 as follows:

$(CH_2)_a[OCH_2CHR^1CH_2]_b$  Formula 3 wherein $R^1$ is a member selected from the group consisting of H, SH, OH, lower alkyl, and aryl; a is an integer from 2 to about 10; and b is 0 or 1. In Formula 3, the terminal carbon (or —$CH_2$— group most distal to the solid support) can attach to the ligand (or group of ligands) by any suitable bond. It is preferred that the terminal carbon on the spacer be covalently bonded to a nitrogen or another carbon present on the ligand or ligand backbone. However, it is not the purpose of the invention to describe the point of attachment between the SS-A-X- portion of the composition and the L portion of the composition. Any functional point of attachment may be implemented.

When the particulate solid support (SS) is an organic resin or polymer, such as phenolic resins, polystyrenes, and polyacrylates, it will generally be a hydrophilic polymer or polymer derivatized to have a hydrophilic surface and contain polar functional groups. The ligand (L) (or backbone supporting a group of ligands) will then generally contain a functional grouping reactive with an activated polar group on the polymer. The covalent linkage (A) and the spacer (X) can then be integrated, and may actually be a single linkage, formed by the reaction between the activated polar group from the polymer and the functional group from the ligand and may be represented by Formula 4 below:

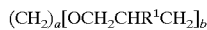

Formula 4 where u is 0 or 1; v and z are independently 0 or an integer from 1 to 10; and Y is a functional group or aromatic linkage such as an ether (O), sulfide (S), imine (C=N), carbonyl (CO), ester (COO), thioester (CSO), amide (CONH), thioamide (CSNH), amine (NH), lower alkylamine (NR), sulfoxide (SO), sulfone ($SO_2$), sulfonamide ($SO_2NH$), phenylene ($C_6H_4$), benzylene ($CH_2$—$C_6H_4$), and the like. At least one of x, y or z must be 1.

The SS-A-X- portion of Formula 1 can be attached to any functional location of a palladium(II)-bound ligand backbone grouping, e.g., the -$B_m$[L:Pd(II)]$_n$ portion of Formula 1. For example, when m is 1, B is a 5 carbon chain, and n is 2, the structure can be [$L^1$:Pd(II)]—[$(CH_2)_5$]—[$L^2$:Pd(II)]. With this arrangement, the SS-A-X- portion can be covalently attached to $L^1$ directly, $L^2$ directly, or any of the 5 carbons separating $L^1$ from $L^2$. In another example, when m is 1, B is a 14 carbon chain, and n is 3, one possible structure of the palladium(II)-bound ligand backbone grouping can be [$L^1$:Pd(II)]—[$(CH_2)_5$]—[$L^2$:Pd(II)]—[$(CH_2)_9$]—[$L^3$:Pd(II)]. With this arrangement then, the SS-A-X- portion can be covalently attached to L1 directly, $L^2$ directly, $L^3$ directly, or any of the 14 carbons present on the organic backbone. If other atoms are present on the organic backbone, then the SS-A-X- portion of the composition can be attached to those constituents as well.

Turning now to the specifics of the ligand (L) portion of Formula 1, several ligands can be used to complex with specific heterocyclic aromatic amine bases. When these ligands are complexed with Pd(II) and tethered to a solid support, nonchromatographic separations can be carried out that are selective of one heterocyclic aromatic amine base over another. Additionally, if from 2 to 4 properly selected ligands are each complexed with Pd(II), tethered to a solid support, and appropriately spaced, then specific nucleotide sequences can be separated from other nucleotide sequences.

When the desired heterocyclic aromatic amine base to be selected and/or separated is guanine (G) (including that in its nucleoside or nucleotide form), then a ligand (L) containing the sequence of formula 5 below, complexed to a Pd(II) ion can be used.

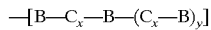

Formula 5

In the above formula, each B can individually be nitrogen, sulfur, or phosphorus; x can be 2 or 3; and y can be 0, 1 or 2. Pendent functional groups or R groups (not shown) can be present on each of the carbons that include H or straight or branched chained lower alkyl, aryl, or lower alkyl aryl. An example of a pendent alkyl group is shown in Formula Si. Alternatively, one or more heterocyclic or carbon aromatic ring(s) can be present that incorporates two adjacent carbons of Formula S. An example of a pendent aryl group that utilizes this arrangement is shown in Formula Sh. This being stated, it is not the purpose of the invention to describe each and every possible side chain that can be present on the ligand. All that is required is that the ligand contain a section as shown in Formula 5. For example, a pyridine ring, or the like, could be used to provide one or more B groups of Formula 5, and still be within the scope of Formula 5. A symbol for a bond and brackets are shown to denote that the ligand will be attached to a solid support, such as through a covalent linkage mechanism, a spacer grouping, and/or an organic backbone, depending on the embodiment.

Below are included, by way of illustration, examples of ligands that can be used for the nonchromatographic selection and/or separation of guanine (G) (including its nucleoside or nucleotide) from other heterocyclic aromatic amine bases and their nucleotides and nucleosides. Each of these ligands (5a–5k) are included within the scope of Formula 5.

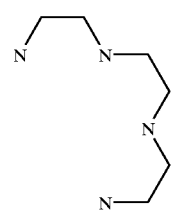

5a

5b 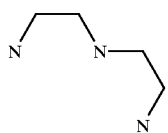

5c 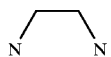

5d 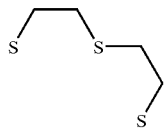

5e 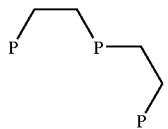

5f 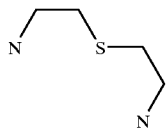

5g 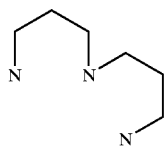

5h 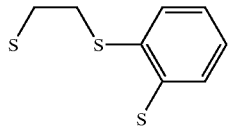

5i 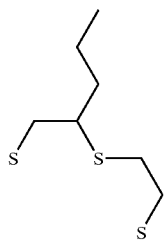

5j 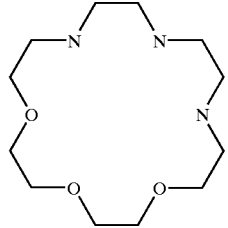

5k 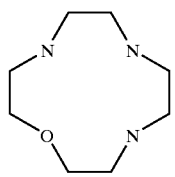

It is important to note that the ligands shown above are not, in and of themselves, the novel feature of the invention. The invention resides in the compositions and methods of using the compositions for separating desired heterocyclic aromatic amine bases, nucleosides, nucleotides, or sequences of DNA or RNA using non-chromatographic separation techniques. These ligands must be complexed to Pd(II) and bound to a solid support in order for the separation to be effectuated.

An example of a ligand of Formula 5, bound to a solid support, and complexed to Pd(II) is shown below.

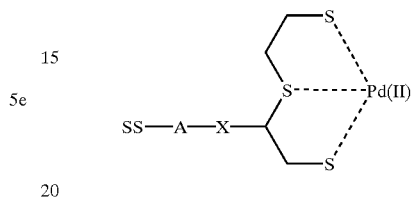

The above structure (using ligand 5d) is particularly adapted for the separation of guanine (G) from other nucleotides, nucleosides, or heterocyclic aromatic amine bases because three coordination sites are used to bind the Pd(II) to each of the sulfur groups, leaving one additional coordination site on the Pd(II) ion to bind with the guanine (G). Likewise, any of the ligands where y is 1 (as shown in Formula 5) generally provide the highest selectivity in separations. The point of attachment where the SS-A-X-portion attaches to the ligand is shown by way of example, and does not necessarily provide better separation results compared to structures where the point of attachment is different.

Turning now to the separation of adenine (A) (including that in its nucleoside or nucleotide form) from other undesired heterocyclic aromatic amine bases, certain ligands when complexed to Pd(II) provide for effective separations. These ligands (L) contain the sequence of Formula 6 below:

-[D-C—N—C-D]                   Formula 6

In Formula 6, N and C are nitrogen and carbon, respectively; and each D is independently a negative binder in addition to that provided by nitrogen. Appropriate negative binders include carboxyl moieties, phosphonic moieties, and sulfonic moieties. Additionally, C—N—C can either be covalently bonded as shown, or can combine to be part of a heterocyclic ring. Again, pendent functional groups or R groups (not shown) can be present on each of the carbons, or if applicable, on the aromatic ring. Such groups can include H or straight or branched chained lower alkyl, aryl or lower alkyl aryl. Additionally, any other of such R groups can be present, provided they do not significantly intefere with the binding of adenine (A). This being said, it is not the purpose of the invention to describe each and every possible side chain that can be present on the ligand. All that is required is that the ligand contain a section as shown in Formula 6. A symbol for a bond and brackets are shown to denote that the ligand will be attached to a solid support, such as through a covalent linkage mechanism, a spacer grouping, and/or an organic backbone, depending on the embodiment.

Below are included, by way of illustration, examples of ligands that can be used for the nonchromatographic separation of adenine (A) (including its nucleoside or nucleotide) from other heterocyclic aromatic amine bases and their nucleotides and nucleosides. Each of these ligands (6a–6c) shown are within the scope of Formula 6.

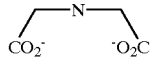

6a

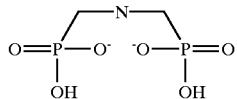

6b

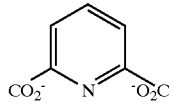

6c

Of the three examples shown, dipicolinic acid (6b) and aminodiphosphate (6c) are the most preferred ligands for use with the present invention. Additionally, though an example having a sulfonic negative binder is not shown, such structures may also provide effective separation results.

Again, it is important to note that the ligands shown above (or other ligands within the scope of Formula 6) are not of themselves the invention. The invention is found in the compositions and methods for separating desired heterocyclic aromatic amine bases, nucleosides, nucleotides, or sequences of DNA or RNA using nonchromatographic separation techniques. Thus, these ligands must be complexed to Pd(II) and bound to a solid support in order for the separation to be effectuated.

An example of a ligand of Formula 6, bound to a solid support, and complexed to Pd(II) is shown below.

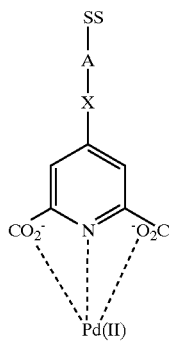

With respect to the above structure, or any other ligand structure within the parameters set forth in Formula 6, the point of attachment where the SS-A-X- portion attaches to the ligand is shown by way of example, and does not necessarily provide better separation results compared to structures where the point of attachment is different. Adenine (A) is considered to be more hydrophobic than some of the other heterocyclic aromatic amine bases. Thus, the use of an organic solid support such as styrene is preferred, though inorganic solid supports such as silica are also functional.

When the desired heterocyclic aromatic amine base to be separated is thymine (T) or uracil (U), then a ligand (L) containing the sequence of formula 7 below, complexed to a Pd(II) ion can be used.

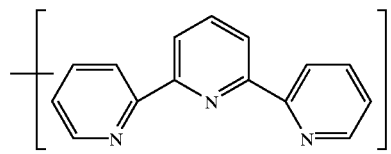

Formula 7

Though many ligands containing this structure are useful, it is preferred that a phenyl group be attached to a carbon of one or more of the heterocyclic aromatic amine groups, such as is shown below in Formula 8:

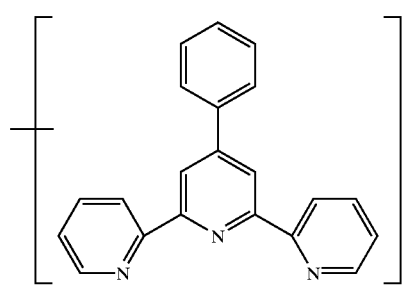

Formula 8

With respect to Formulas 7 and 8, pendent functional groups or R groups (not shown) can be present at any location off of the aromatic rings, as long as they do not significantly interfere with the binding of the Pd(II) ion to the nitrogens on the aromatic ring. Some additional R groups may, in fact, help the selectivity of the ligand in certain circumstances, as illustrated by the additional phenyl group included as part of Formula 8 compared to Formula 7. In both Formula 7 and Formula 8, a symbol for a bond as well as brackets are shown to denote that the ligand will be attached to a solid support, such as through a covalent linkage mechanism, a spacer grouping, and/or an organic backbone, depending on the embodiment.

The ligand containing the sequence shown in Formula 7 can be tethered to the solid support from any functional location. One such structure is shown below wherein the ligand of Formula 7 (having an extra phenyl group attached thereto as in Formula 8) is complexed to Pd(II) and is further attached to a solid support.

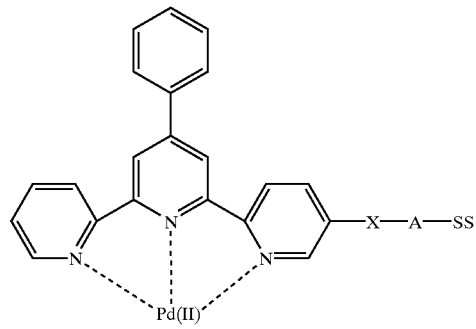

Again, with respect to the above structure, the point of attachment where the SS-A-X- portion attaches to the ligand is shown by way of example, and does not necessarily provide better separation results compared to structures where the point of attachment is different. Attachment to the phenyl group, for example, may also be desirable.

The ligand of Formula 7 (and preferably of Formula 8) functions for the separation of thymine (T) and uracil (U) because the structure aromatically lines up the nitrogen atoms in a desired stereo configuration. Thus, the structure is both planer and bulky. This configuration may also work because the Pd(II) ions are protected by bulky groups. Guanine (G) is also attracted to the Pd(II) bound ligand of Formulas 7 and 8, but because guanine (G) is larger than thymine (T) and uracil (U), guanine (G) has difficulty binding. Conversely, thymine (T) and uracil (U) are small enough such that binding can be more easily occur.

When the desired heterocyclic aromatic amine base to be separated is cytosine (C) (including its nucleoside or nucleotide), then an appropriately configured ligand complexed to a Pd(II) ion, and bound to a solid support can also be used. Formula 9 below, which is included by way of example, provides a ligand that can be used for the non-chromatographic selection and/or separation of cytosine (C) from at least some of the other heterocyclic aromatic amine bases and their nucleotides and nucleosides:

Formula 9

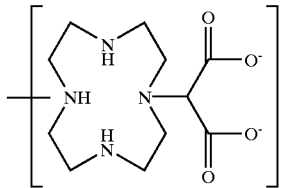

A symbol for a bond and brackets are shown to denote that the ligand will be attached to a solid support, such as through a covalent linkage mechanism, a spacer grouping, and/or an organic backbone, depending on the embodiment. A specific example of a ligand of Formula 9, bound to a solid support, and complexed to Pd(II) is shown below.

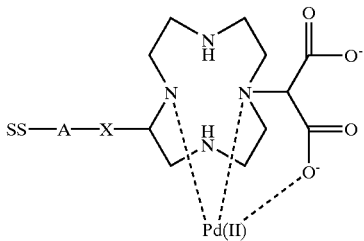

The above structure is provided by way of example, and is particularly adapted for the separation of cytosine (C) from other nucleotides, nucleosides, or heterocyclic aromatic amines, particularly uracil, thymine, and adenine. The point of attachment where the SS-A-X- portion attaches to the ligand is also shown by way of example, and does not necessarily provide better separation results compared to structures where the point of attachment is different. The unpaired carboxy group can provide some steric hindrance and provides symmetry to the ligand, and assists in the selectivity.

Turning to the loading of the palladium to the ligands described herein, Pd(II) can be loaded on the ligands described herein by one of a number of techniques. Before loading Pd(II) on a specific ligand, a basal capacity (mmol/g) of the ligand should be ascertained. The basal capacity is typically determined by shaking the specific ligand with a dilute buffered solution of a base metal known to be complexed by the ligand, or by shaking with a dilute solution of Pd(II) at a pH from about 2 to 3. The amount of Pd(II) needed to load a specific mass of ligand can then be calculated as described below in Formulas 10 and 11:

$$\text{mmol Pd(II)} = [\text{ligand mass (g)}] \times [\text{desired loading (mmol/g)}] \times [\text{excess factor (1.01-3)}] \quad \text{Formula 10}$$

$$\text{volume of solution (ml)} = [\text{mM Pd(II)}/1000] \times [\text{mmoles Pd(II) required}] \quad \text{Formula 11}$$

Larger excess factors are needed if the ligand is to be Pd(II) loaded above its 1:1 stoichiometric basal level. Additionally, the concentration of Pd(II) can be increased 5-10 fold if the Pd(II) is to be loaded above its basal capacity. Normally, 1 mM Pd(II) is used for loadings at or below the basal capacity.

Pd(II) can be loaded onto ligand bound solid supports by any functional method. Two examples are provided herein by way of example. A first method of loading Pd(II) onto a ligand bound solid support is described below. First, a Pd(II) solution is made by diluting a stock solution of $Pd(NO_3)_2$ or $PdCl_2$ into 0.5M or 0.125M $NaHPO_4$ at a pH of about 6–7. The pH is NaOH adjusted and brought to a final volume using $H_2O$. Next, the ligand or ligand bound to a solid support is mixed into the Pd(II) solution and shaken until the composition becomes clear or colorless. This can take from a few minutes to a few hours. Alternatively, if color remains, then the mixing should be allowed to occur until equilibrium is reached, e.g., from about 2 to 15 hours. The Pd(II) loaded ligands (attached to the solid supports) can then be washed with 3–4 aliquots of 0.5M $NaHPO_4$, decanted, blofted, and stored wet for a short period of time, or allowed to dry for longer period storage.

A second method for loading a ligand bound solid support with Pd(II) can be as follows. With respect to some ligands, the use of a phosphate buffer is either so kinetically slow, or otherwise inhibited such that it is not practical to load Pd(II) using a phosphate solution. In these circumstances, the Pd(II) solution can be diluted with water and pH adjusted to 2–3 with acid or base as needed. Above pH 4, $Pd(OH)_2$ often forms a precipitate. Following the shaking of the ligand bonded to the solid support in a low pH Pd(II) solution, the composition is washed using 0.5M phosphate buffer at pH 7 or water until a pH of about 7 is reached.

The ability to separate one heterocyclic aromatic amine base from others using the palladium bound compositions disclosed herein is advantageous. Typically, with this type of technology, selectivity is provided in large part due to the choice of metal. In other words, the metal dominates the selectivity. With the present invention, no matter what heterocyclic aromatic amine base is desired for separation, Pd(II) is the metal ion that is used. Thus, the specified ligand (L) combined with the Pd(II) is what provides the selectivity, whereas the Pd(II) provides a significant amount of the attraction.

Thus far, description has been given with respect to compositions described in Formula 1 where "n" is 1. However, if the desire is to separate out nucleotide sequences from other nucleotide sequences, i.e., when "n" is from 2 to 4, then any of the Pd(II) bound ligands described above can be bound to another Pd(II) bound ligand(s) described above (or like ligands) by a ligand supporting backbone. With each Pd(II) bound ligand covalently attached to one or more other Pd(II) bound ligands via a backbone, such a combination is in condition to bind nucleotide sequences. However, in order to effectuate the separations of the present invention, the ligand supporting backbone (or one of the ligands bound to the ligand supporting backbone) is also tethered to a solid support as described previously. All that is required is that the ligand supporting backbone be of a functional length such that desired heterocyclic aromatic amine bases of a nucleotide sequence can be bound to the Pd(II) bound ligands. Optimally, the backbone can be from 3 to 20 carbons in length (between any two adjacent ligands), though this is a preferred range only and other configurations may also be functional. Additionally, the ligand supporting backbone does not have to consist solely of carbon atoms. For example, oxygen and/or sulfur may also be present, as long as their presence does not substantially interfere with nucleotide binding at the ligand/Pd(II) site or sites. Examples of structures having a ligand supporting backbone wherein "n" of Formula 1 is other than 1 are shown in FIG. 1 and FIG. 2.

In FIG. 1, a structure is shown that can be used to bind adenine-guanine nucleotide sequences. A solid support 10 is shown. In this embodiment, the solid support 10 is silica gel. Attached to the solid support 10 is a covalent silane linkage mechanism 12. The covalent linkage mechanism is used to bridge the gap between organic chains and the inorganic solid support 10. A spacer grouping 14 is also shown. The spacer grouping 14 in this example contains glycidyloxypropyl. The spacer grouping 14 is bound to a ligand supporting backbone 16. In this embodiment, the ligand supporting backbone is a 5 carbon straight chain group having the point of attachment to the spacer grouping at C3. Attached at each end of the ligand supporting backbone 16, i.e., C1 and C5, are two Pd(II) bound ligands 18a, 18b. Pd(II) bound ligand 18a is preferably a Pd(II) bound ligand such as that described in connection with Formula 6. Pd(II) bound ligand 18b is preferably a Pd(II) bound ligand such as that described in connection with Formula 5.

Shown attached to the structure described above is a desired nucleotide sequence 28. The desired nucleotide sequence is comprised of adenine and guanine which collectively comprise the heterocyclic aromatic amine bases 20. Each base 20 is bound to 2-deoxy-D-ribose 24 by a β-N-glycoside bond 22. Connecting each 2-deoxy-D-ribose is a monophosphate 26. The 5' end 30 and the 3' end 32 are also shown.

Figure 2:
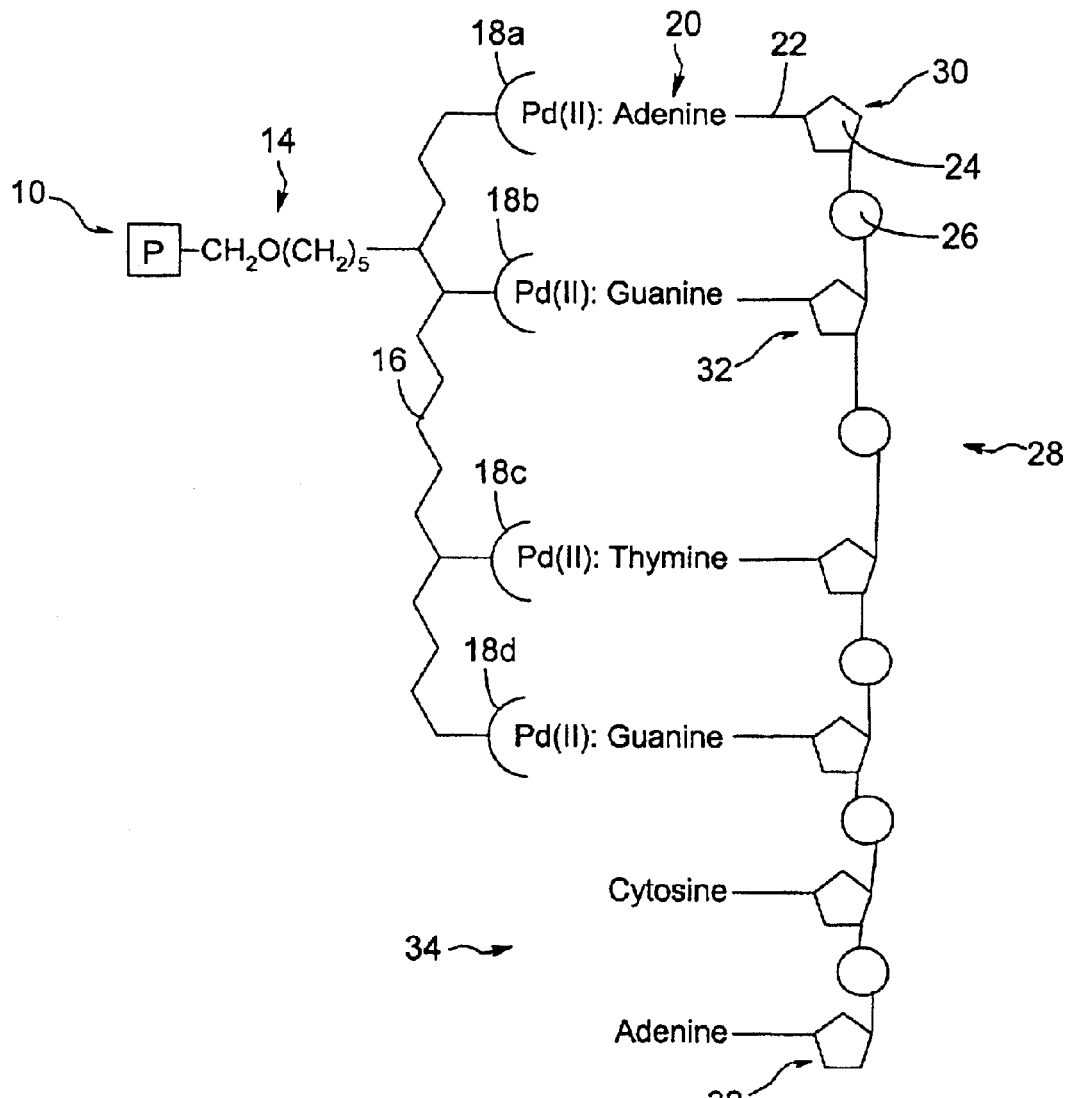
FIG. 2 is a schematic representation of an embodiment of the present invention wherein nucleotide sequence A-G-T-G is selected.

Turning now to FIG. 2, a structure is shown that is selective for the nucleotide sequence adenine-guanine-thymine-guanine. In this figure, a solid support 10 is shown that is organic. Specifically, in this embodiment, the solid support 10 is polystyrene. Because the solid support 10 is organic, there is no need for a separate covalent linkage mechanism. In accordance with Formula 4, the covalent linkage mechanism (not shown) and a spacer grouping can be integrated into a single spacer grouping 14. In some cases, the spacer grouping may actually be a single linkage formed by the reaction between an activated polar group from the polymer and a functional group from the ligand (or ligand backbone). In this embodiment, the spacer grouping 14 is more than a single linkage and is attached to a ligand supporting backbone 16. The point of attachment is at C4 of a 15 carbon alkyl chain. Though it has been described that the spacing between respective ligands is preferably from 3 to 20 carbons in length, to be clear, that is meant to mean carbon atoms of the chain between each individual ligand. Additionally, carbon is not the only constituent that can be present in the backbone. In FIG. 2, there is a 15 carbon chain backbone, however spacing between each ligand is 3 carbons, 5 carbons, and 3 carbons, respectfully. Additionally, the four remaining carbons on the 15 carbon chain are attached to a Pd(II) bound ligand 18a–d. Pd(II) bound ligand 18a is preferably a Pd(II) bound ligand such as that described in connection with Formula 6. Pd(II) bound ligands 18b, 18d are preferably Pd(II) bound ligands such as those described in connection with Formula 5. Pd(II) bound ligand 18c is preferably a Pd(II) bound ligand such as that described in connection with Formula 7 or Formula 8.

Shown attached to the structure described above is a desired nucleotide sequence 28. The desired nucleotide sequence is comprised of adenine, guanine, and thymine which are individually heterocyclic aromatic amine bases 20 in a nucleotide sequence form. Each base 20 is bound to 2-deoxy-D-ribose 24 by a β-N-glycoside bond 22. Connecting the each 2-deoxy-D-ribose is a monophosphate 26. The 5' end 30 and the 3' end 32 are also shown. It is noted in FIG. 2 that the nucleotide sequence contains six nucleotide bases. As such, two unbound bases 34 are shown. Thus, the present invention can separate nucleotide sequences that contain more bases than the Pd(II) bound ligands 18a–d are designed to coordinate or complex with.

Although in both FIG. 1 and FIG. 2, the spacer grouping 14 is attached to the ligand supporting backbone 16, this is not required. This being the case, the spacer grouping 14 can be attached to one of the Pd(II) bound ligands 18 itself. For example, if the Pd(II) bound ligand is an ethyleneamine, then the spacer grouping 14 can be covalently attached directly to a nitrogen. In this situation, the ligand supporting backbone 16 is used for the single purpose of separating one Pd(II) bound ligand from other Pd(II) bound ligands (whereas in FIG. 1 and FIG. 2, the backbone also acts as the point of attachment).

The separation methods of the present invention can be carried out by utilizing the compositions previously described. Steps that can be carried out in the separation methods of the present invention can include the following: 1) identifying the heterocyclic aromatic amine base, nucleoside, nucleotide, or nucleotide sequence that is desired to be separated from other undesired amines or substances; 2) selecting corresponding Pd(II) bound ligands that are selective for the heterocyclic amine base, nucleoside, nucleotide; or alternatively, selecting a corresponding appropriately spaced series of Pd(II) bound ligands, i.e., preferably from 2 to 4 Pd(II) bound ligands, that are selective for the nucleotide sequence; 3) tethering the Pd(II) bound ligands (or series of Pd(II) bound ligands) to solid supports, forming the selective composition; 4) loading the selective composition in a separation device with a source solution, thereby loading the Pd(II) bound ligands with desired heterocyclic aromatic amine base, nucleoside, nucleotide, or nucleotide sequence; 5) washing the loaded column with a biologically acceptable and compatible buffer (if in the form of nucleotides, the buffer cannot hydrolyze the nucleotide(s)); 6) eluting with a smaller amount of receiving solution; and 7) washing the receiving solution from the column as part of a post-elution wash. Though these steps are all mentioned together, these steps are not all critical. For example, some steps can be removed, depending on the circumstances.

For example, in one embodiment, a method for concentrating, removing, or separating a desired heterocyclic aromatic amine base or a nucleotide sequence containing the desired heterocyclic aromatic amine base from a source solution can comprise several of the above-mentioned steps. In this method, steps can include (a) contacting a source solution having a first volume with a composition comprising a palladium(II)-bound ligand covalently bonded to a solid support, wherein the source solution contains a desired heterocyclic aromoatic amine base and an undesired heterocyclic aromatic amine bases, and wherein the palladium(II)-bound ligand is preferentially selective of the desired heterocyclic aromatic amine base; (b) removing the source solution from contact with said composition to which the desired heterocyclic aromatic amine base has been complexed; (c) contacting the composition having the desired heterocyclic aromatic amine bases associated therewith with a smaller volume of an aqueous receiving solution in which the desired heterocyclic aromatic amine bases are stripped from the composition; and (d) recovering the desired heterocyclic aromatic amine bases in concentrated form in said receiving solution.

In an alternative embodiment, a method for concentrating, removing, or separating a nucleotide chain containing a specific nucleotide sequence from a source solution can comprise the steps of (a) identifying a nucleotide chain that contains a desired nucleotide sequence that is desired for concentrating, removing, or separating from a source solution; (b) providing a composition that will selectively bind the nucleotide sequence; (c) contacting the source solution having a first volume with the composition wherein a chemical attraction between the composition and the nucleotide sequence occurs; (d) removing the source solution from contact with the composition, wherein the composition has the nucleotide sequence attracted thereto; (e) contacting the composition having the nucleotide sequence attracted thereto with a smaller volume of an aqueous receiving solution in which the nucleotide chain is stripped from the composition; and (f) recovering the nucleotide chain in concentrated form in the receiving solution.

If a washing step is followed, a preferable buffer for use is a phosphate buffer, though other buffers can be used as would be known to those skilled in the art. Additionally, with respect to the eluting step, preferably at from 0.1 to 1.0 M of ammonia or ammonia buffer can be used, though other known receiving solutions will work, e.g., ethylene diamine and thiocyanate. Ammonia is particularly useful from a chemical perspective because it is a stronger binder to Pd(II) than the base it displaces. Additionally, at pH of 9–10, even oligonucleotides are still stable. Thus, the pH is high enough to strip the nucleotide from the compositions of the present invention, but is not high enough to alter the properties of nucleotide or nucleotide sequences. When selecting an elution composition for use, the desired properties to achieve include elution substances that are 1) strong enough to displace the base without altering its configuration; 2) not strong enough to displace the Pd(II); and 3) can be washed off.

With respect to the washing step, if ammonia is used as the elution agent, then a phosphate buffer works well at removing the ammonia (when the pH of ammonia gets below about 8.5, it is protonated and becomes an ammonium ion). If ethylenediamine is used as the elution agent, then the pH must be lowered even further, making it a less desirable elution material. Likewise, thiocyanate requires a pH of about 2 to effectuate a wash. This is not a problem at this stage because the bases have already been removed in the receiving solution. However, the column must be returned to its original more neutral state (pH) to reuse the column for a further separation. Thus, the use of ammonia for the elution stage and a phosphate buffer for the washing stage is desirable, as little or no further preparation steps are required with respect to the separation device before running another separation.

EXAMPLES

The following examples illustrate embodiments of the invention that are presently best known. Thus, these examples should not be considered as limitations of the present invention, but are merely in place to teach how to make the best known compositions of the present invention based upon current experimental data. As such, a representative number of compositions and their method of manufacture are disclosed herein.

In the following examples, several abbreviations will be used will be understandable to one skilled in the art. Some abbreviations include: DMF (dimethylformamide), RT (room temperature), Trit (triphenylmethyl), THF (tetrahydrofuran), Me (methyl), Et (ethyl), DMAP (4-dimethylaminopyridine), Ts (tosylate), and BOC (t-butoxycarbonyl).

Example 1

Preparation of Diethylenetriamine Bonded to Silica Gel

To 0.3 L of toluene was added 13 g of y-glycidoxypropyltrimethoxysilane and 6.24 g of diethylenetriamine and the mixture was stirred overnight. To the mixture was added 60 g of silica gel (35–60 mesh) and the product was heated at 80° C. for 16 hours. A product was filtered off, washed with water and methanol, and dried under reduced pressure. The product produced can have one of the following structure (a or b):

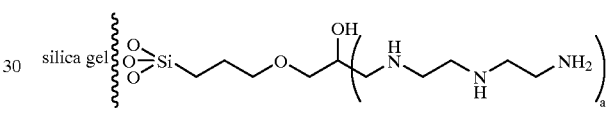

or

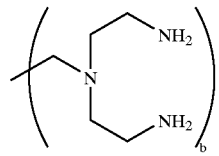

Example 2

Preparation of Polystyrene Bonded to Diethylenetriamine

About 0.5 g of chloromethylpolystyrene (predried by coevaporation with 50 ml of benzene) was heated at 120° C. with 10 g of diethylenetriamine for 24 hours. After the product was cooled, the beads were collected by filtration, washed with $CH_3$ OH, and dried under reduced pressure. The product produced can have one of the following structure (a or b):

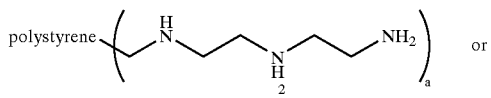

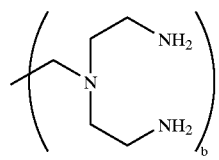

Example 3

Preparation of Tetramethyldiethylenetriamine Bonded to Silica Gel

To a well-stirred solution of 1 g tetramethyldiethylenetriamine and 0.8 ml of triethylamine in 75 ml DMF at room temperature was added 1.0 ml of bromopropyltrimethoxysilane dropwise. The resulting mixture was heated to 80° C. After 16 hours, 11 g of silica gel was added. After an additional 4 hours, the reaction product was cooled to room temperature. The solution was decanted and silica gel was added to the THF, filtered, and washed with excess THF and methanol. Next, the product was dried under vacuum for 16 hours at 55° C., producing about 11.5 g of tetramethyldiethylenetriamine bonded to silica gel. The reaction formula is shown below:

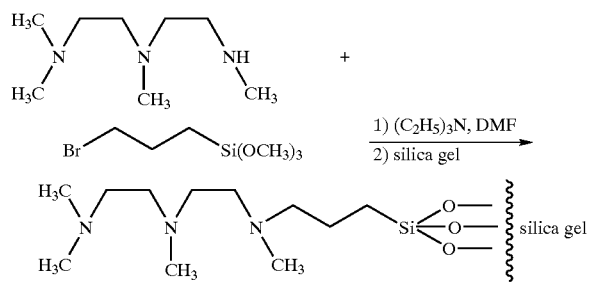

EXAMPLE 4

Preparation of Tetramethyldiethylenetriamine Bonded to Polystyrene

About 318 mg of tetramethyldiethylenetriamine and 0.5 g of the Merrifield resin was refluxed in 25 ml of dioxane. After 16 hours it was cooled, filtered, and the resin was washed with an excess of THF and methanol and dried under vacuum for 16 hours at 55° C. About 0.55 g of a tetramethyldiethylenetriamine bonded to polystyrene was produce. The reaction formula is shown below:

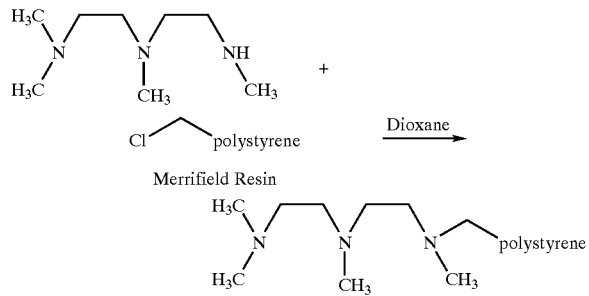

Example 5

Preparation of N,N-dimethyl-N'-tosylethylenediamine

To 10.5 g of N,N'-dimethylethylenediamine in 250 ml of THF was added 26 g of tosylchloride (TsCl) in small portions at room temperature. After 16 hours, solvents were evaporated and the residue was apportioned between $H_2O$ and $CH_2Cl_2$. A $CH_2C_2$ layer was separated and washed with brine, dried ($MgSO_4$), filtered, and concentrated under reduced pressure. About 26.5 g of N,N-dimethyl-N'-tosylethylenediamine (93%) was produced. The reaction steps are shown below:

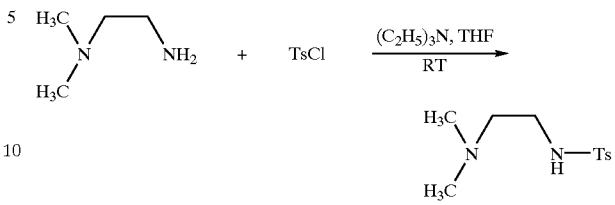

Example 6

Preparation of N,N'-ditosyl-2-{3-allyloxy-2-[2-(2-hydroxy-ethylamino)-ethoxy]-propylamine}-ethanol To 9.2 g of N-tosylaminoethanol and 55 g of cesium carbonate in 300 ml of DMF at room temperature was added dropwise a solution of 10 g of allyloxy ditosylate glycol in 100 ml of DMF. The temperature was raised to 70° C. After 16 hours, the product was cooled to room temperature and filtered. The DMF was evaporated under reduced pressure and the resulting residue was portioned between $H_2O$ and $CH_2Cl_2$. A $CH_2Cl_2$ layer was washed with brine, dried ($MgSO_4$), filtered, and concentrated under reduced pressure. A crude product N,N'-ditosyl-2-{3-allyloxy-2-[2-(2-hydroxy-ethylamino)-ethoxy]-propylamine}-ethanol (85%) was formed as an intermediate. The process steps are shown below:

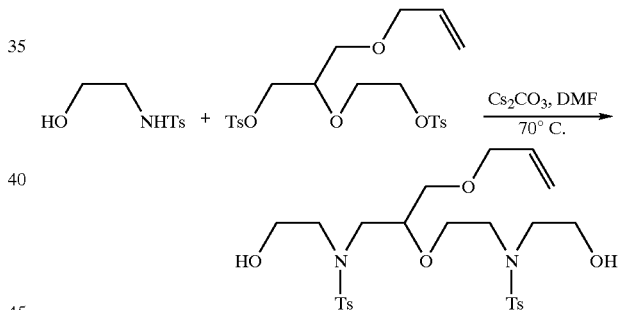

Example 7

Preparation of N,N'-ditosyl-2-{3-allyloxy-2-[2-(2-tosyloxy-ethylamino)-ethoxy]-propylamine}tosyloxyethane To a well-stirred solution of 11.8 g of the N,N'-ditosyl-2-{3-allyloxy-2-[2-(2-hydroxy-ethylamino)-ethoxy]-propylamine}-ethanol in 200 ml of THF at 0° C. was added 6.7 g powdered KOH followed by a dropwise addition of a solution of 8.5 g tosychloride in 100 ml of THF. After 16 hours at room temperature, the product was filtered and the solvents evaporated off. The residue was apportioned between $H_2O$ and $CH_2Cl_2$. A $CH_2Cl_2$ layer was washed with brine, dried ($MgSO_4$), filtered, and concentrated under reduced pressure. The residue was purified using silica gel and eluted with ethyl acetate/hexane. About 14 g (75%) of N,N'-ditosyl-2-{3-allyloxy-2-[2-(2-tosyloxy-ethylamino)-ethoxy]-propylamine}tosyloxyethane was obtained. The reaction is shown below:

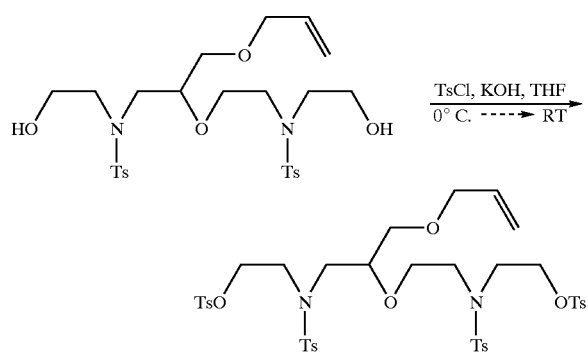

Data verifying the composition was collected using HNMR, and is provided as follows: ¹HNMR(CDCl₃): 7.8–7.5(m, 8H), 7.4–7.2(m,8H), 5.9–5.7(m,1H), 5.3–5.1(m,2H), 4.3–4.1(t,4H), 3.9(d,2H), 3.7–3.0(m,13H), 2.4(s,6H) 2.3(s, 6H).

Example 8

Preparation of a Tetratosylate of Oxohexaamine

To a well-stirred solution of 2.7 g of N,N-dimethyl-N'-tosylethylenediamine and 13.5 g of cesium carbonate in 150 ml of DMF at room temperature was added a solution containing 4.5 g of N,N'-ditosyl-2-{3-allyloxy)-2-[2-(2-tosyloxy-ethylamino)-ethoxy]-propylamine}tosyloxyethane in 50 ml of THF. After 40 hours at 70° C., the product was cooled, filtered and concentrated under reduced pressure. The residue was apportioned between H₂O and CH₂Cl₂. A CH₂Cl₂ layer was separated, washed with brine, dried (MgSO₄), filtered, and concentrated under reduced pressure. The residue was purified on silica gel and eluted with ethyl acetate/methanol (2/1 v/v). About 4.7 g (85%) of N,N',N'', N'''-tetratosyl-N-(3-allyloxy-2-{2-[2-(2-dimethylamino-ethylamino)ethylamino]-ethoxy}-propyl-N'-(2-dimethylamino-ethyl)-ethane-1,2-diamine was obtained, as shown by the reaction steps below:

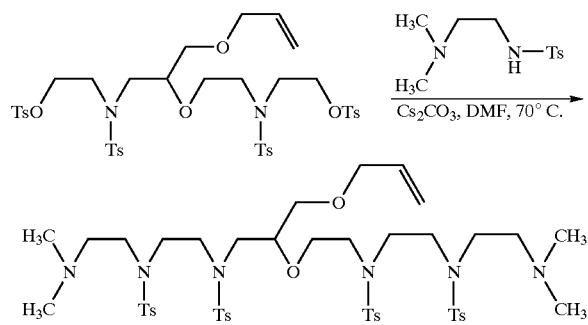

Data verifying the composition was collected using HNMR, and is provided as follows: ¹HNMR(CDCl₃): 7.6(d,8H) 7.3(d,8H), 5.8(m,1H), 5.2(m,2H), 3.9(d,2H), δ 3.7–3.1(m, 21H), 2.5–2.3(m,16H), 2. 1(s,12H).

Example 9

Preparation of a N-(3-allyloxy)-2-{2-[2-(2-dimethylamino-ethylamino]-ethoxy}-propyl-N'-(2-dimethylamino-ethyl)ethane-1,2-diamine To a well-stirred solution of 4.7 g of a tetratosylate in 50 ml of methanol was added 5.8 g of sodium hydrogen phosphate, 37 g of a 6% of sodium amalgam and 20 mg of anthracene. The solution was refluxed and after 5 days, was cooled, filtered, and concentrated under reduced pressure. The residue was purified using a silica gel and eluted with methanol/ammonium hydroxide (5/1). About 1.3 g of a N-(3-allyloxy)-2-{2-[2-(2-dimethylamino-ethylamino]-ethoxy}-propyl-N'-(2-dimethylamino-ethyl)ethane-1,2-diamine (70%) was produced as a pale yellow oil. Specifically, the process steps were as follows:

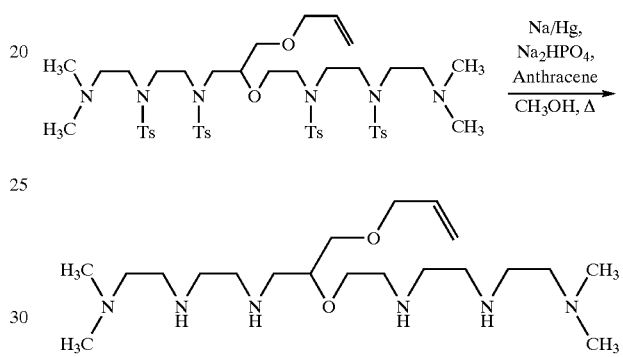

Data verifying the composition was collected using HNMR, and is provided as follows: ¹HNMR(CDCl₃): 5.9(m,1H), 5.2(m,2H), 4.0(d,2H), 3.9(d,2H), 3.7–3.4(m,4H), 2.7–2.6 (m,16H), 2.4(t,4H), 2.1(s,12H), 1.6(s,4H).

Example 10

Preparation of N-(3-allyloxy)-2-{2-[2-(2-dimethylamino ethylamino]-ethoxy}-propyl-N'-(2-dimethylamino-ethyl)ethane-1,2-diamine Bonded to Silica Gel To a well-stirred solution of 100 mg of a N-(3-allyloxy)-2-{2-[2-(2-dimethylamino-ethylamino]-ethoxy}-propyl-N'-(2-dimethylamino-ethyl)ethane-1,2-diamine in 25 ml of toluene was added 60 mg of glycidoxypropyltrimethoxysilane at room temperature. After 16 hours, 0.3 g of silica was added and the product was heated to 85° C. After 24 hours at 85° C., the product was cooled and the solution decanted. The residue was taken in THF, filtered, washed with excess THF and methanol, and dried under reduced pressure for 16 hours at 55° C. About 0.35 g of a N-(3-allyloxy)-2-{2-[2-(2-dimethylamino-ethylamino]-ethoxy}-propyl-N'-(2-dimethylamino-ethyl)ethane-1,2-diamine ligand bonded to a silica gel was produced. The process steps are shown below:

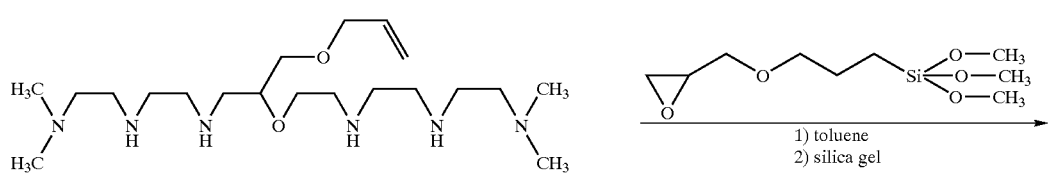

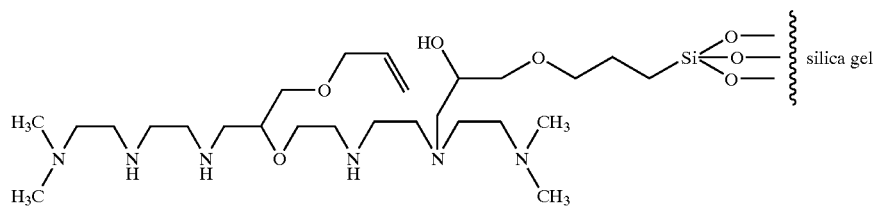

Example 11

Preparation of a N-(3-allyloxy)-2-{2-[2-(2-dimethylamino-ethylamino]-ethoxy}-propyl-N'-(2-dimethylamino-ethyl)ethane-1,2-diamine Bonded to Agarose To a well-stirred solution of 1.0 g (wet) activated agarose in 10 ml of phosphate buffer (pH 10.0) was added 400 mg of a N-(3-allyloxy)-2-{2-[2-(2-dimethylamino-ethylamino]-ethoxy}-propyl-N'-(2-dimethylamino-ethyl)ethane-1,2-diamine. The reaction was heated to 45° C. After 16 hours, the product was cooled, filtered, washed with water and acetone, and dried under reduced pressure for 16 hours at 45° C. About 1.1 g of a N-(3-allyloxy)-2-{2-[2-(2-dimethylamino-ethylamino]-ethoxy}-propyl-N'-(2-dimethylamino-ethyl)ethane-1,2-diamine bonded to agarose was prepared. The preparation is shown schematically below:

Example 12

Preparation of a N-(3-allyloxy)-2-{2-[2-(2-dimethylamino-ethylamino]-ethoxy}-propyl-N'-(2-dimethylamino-ethyl)ethane-1,2-diamine Bonded to Chloromethylpolystyrene To a stirring solution of 0.28 g Merrifield resin in 25 ml of THF was added 0.24 g of a N-(3-allyloxy)-2-{2-[2-(2-dimethylamino-ethylamino]-ethoxy}-propyl-N'-(2-dimethylamino-ethyl)ethane-1,2-diamine ligand. After 16 hours at reflux, the product was cooled, filtered, and washed with methanol, water, methanol, and THF, and dried under reduced pressure for 16 hours at 55° C. About 0.32 g of N-(3-allyloxy)-2-{2-[2-(2-dimethylamino-ethylamino]-ethoxy}-propyl-N'-(2-dimethylamino-ethyl)ethane-1,2-diamine bonded to chloromethylpolystyrene was produced. The preparation is represented schematically below:

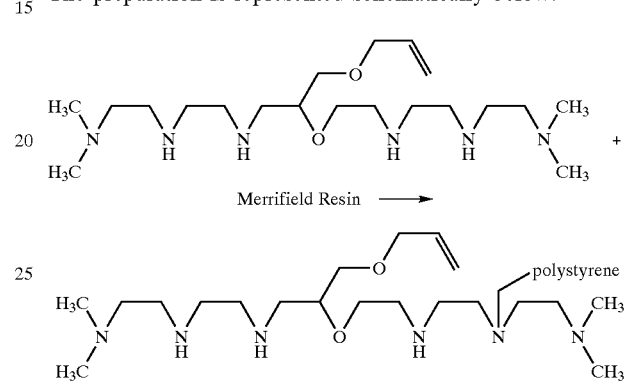

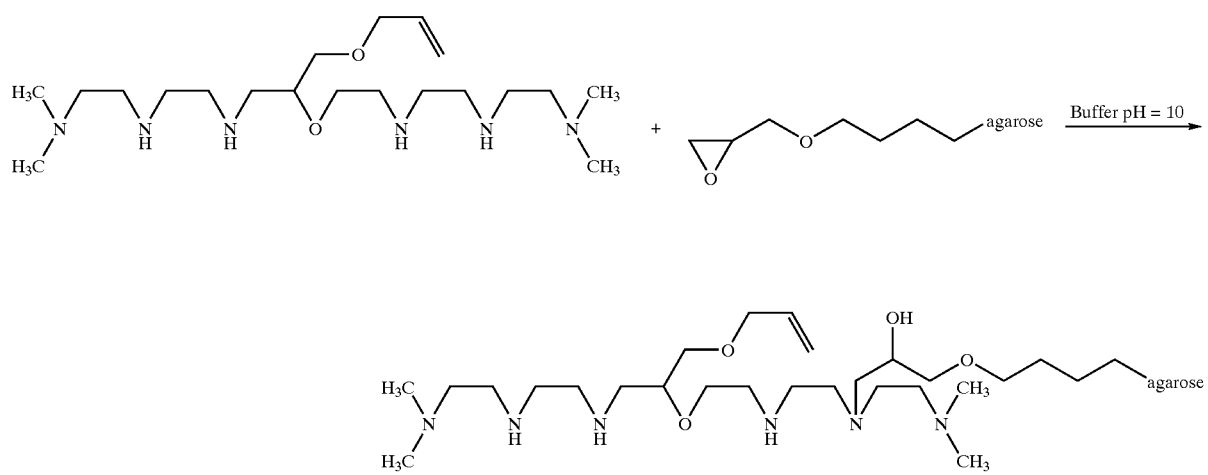

Example 13

Preparation of 1,3-dithiapropane Bonded to Silica Gel

To 0.4 L of toluene and 17 g of 3-mercaptopropyl-trimethoxysilane was added 4.66 g of sodium methoxide in 50 ml of methanol. Next, 8.72 g of 1,3-dibromopropane was dropped into the solution over 10 minutes and was heated to 80° C. (some methanol was distilled off). About 100 g of silica gel (35–60 mesh) was added and then heated and stirred at 80° C. for over 12 hours. After cooling, the product was filtered and washed with water and methanol. About 105 g of 1,3-dithiapropane bonded to silica gel was prepared, as shown in the following structure:

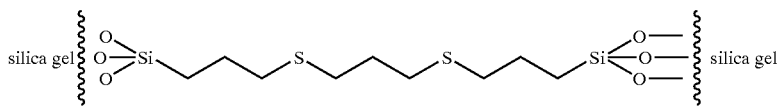

Example 14

Preparation of 4,13-dithia-7,10-dioxa-1,16-hexadecanediol

Into 1 liter of DMF were dissolved 33.35 g of 3-bromopropanol and 20 g of 3,6-dioxa-1,8-octanedithiol, followed by the addition of 225 g of $Cs_2CO_3$. The mixture was stirred at 70° for 3 days and then the DMF was evaporated under reduced pressure. Next, the residue was dissolved in $H_2O$ and $CH_2Cl_2$ and a water layer was extracted twice more with $CH_2Cl_2$. Organic layers were combined, dried over $MgSO_4$, and evaporated. The oil product was distilled (b.p.=210°/0.45 mm Hg) and 19.53 g of 4,13-dithia-7,10-dioxa-1,16-hexadecanediol (59.8%) was collected. The preparation scheme is shown below:

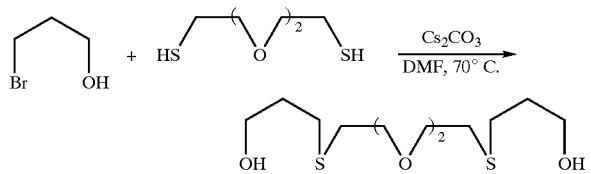

Data verifying the composition was collected using HNMR, and is provided as follows: $^1$HNMR ($CDCl_3$): 3.65(m, $^{121}$I), 2.17(dt,8H), 2.5(s,2H), 1.8(m,4H) $C^{13}$NMR, 71.5, 70.5, 61.5, 32.3, 31.7, 29.2.

Example 15

Preparation of 4,13-dithia-7,10-dioxa-1,16-hexanedecanediol ditosylate

Into 250 ml of $CH_2Cl_2$ was dissolved 19.53 g of the 4,13-dithia-7,10-dioxa-1,16-hexadecanediol of Example 14 and cooled to –5° C. Next, 22.34 g of $Et_3N$ was added to the solution and 27.9 g of TsCl dissolved in 250 ml of $CH_2Cl_2$ and added dropwise at 0° C. The solution was stirred for 24 hours and then washed 3 times with 200 ml $H_2O$. The $CH_2Cl_2$ layer was dried over $MgSO_4$ and evaporated. The resulting oil was purified on silica using ethylacetate/Hexane (1/1 v/v). About 25.78 g (65%) of 4,13-dithia-7,10-dioxa-1,16-hexanedecanediol ditosylate was obtained. The reaction is shown below schematically:

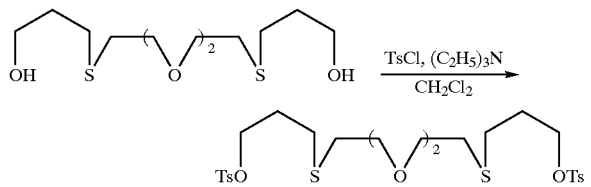

Data verifying the composition was collected using HNMR, and is provided as follows: $^1$HNMR ($CDCl_3$): 7.75(d,4H), 7.35(d,4H), 4.1(t,4H), 3.55(t,8H), 2.65(t,4H), 2.55(t,4H), 2.4(s,6H), 1.9(q,4H).

Example 16

Preparation of 4,13-dithia-7,10-dioxahexadecane-1,16-thiobenzoic Acid

To 700 ml of $CH_3CN$ was dissolved 25.78 g of 4,13-dithia-7,10-dioxa-1,16-hexanedecanediol ditosylate and 16.41 g of potassium thiobenzoate. The product was refluxed for 72 hours. Acetonitrile was evaporated and the crude oil was dissolved in $CHCl_3$. The chloroform layer was washed with $H_2O$ and dried over $MgSO_4$ and evaporated. The reacting product yielded 22.62 g of 4,13-dithia-7,10-dioxahexadecane-1,16-thiobenzoic acid (100%). The reaction described is shown below:

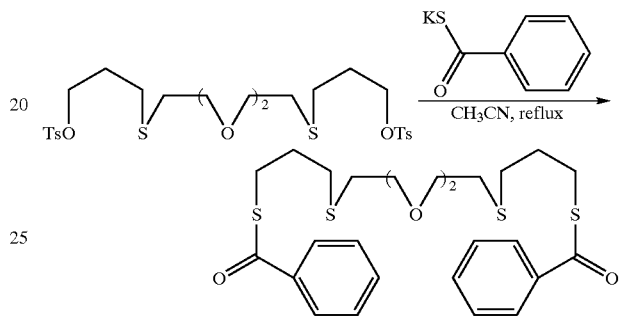

Data verifying the composition was collected using HNMR, and is provided as follows: $^1$HNMR: 7.95(d,4H), 7.52(t,2H), 7.4(t,4H), 3.6(dt,8H), 3.2(t,4H), 2.2(dt,8H), 1.9(1,4H).

Example 17

Preparation of 1,5,14,18-tetrathia-8,11-dioxaoctadecane

To 6.38 g of $LiAlH_4$ in 125 ml THF under argon at 0° C. was added dropwise 22.62 g of 4,13-dithia-7,10-dioxahexadecane-1,16-thiobenzoic acid dissolved in 125 ml of THF. After addition, the product was refluxed for 3 days. Following a cooling step, about 50 ml of $H_2O$ was added dropwise and then the solution was filtered. The filtrate was mixed with 600 ml of $CHCl_3$ and stirred overnight. The product was then filtered, evaporated, and a crude product was purified on alumina oxide with $CHCl_3$/Hexane (2/1 v/v) followed by $CHCl_3$. About 1.85 g (13%) of 1,5,14,18-tetrathia-8,11-dioxaoctadecane was collected. The process steps for obtaining this composition are shown schematically below:

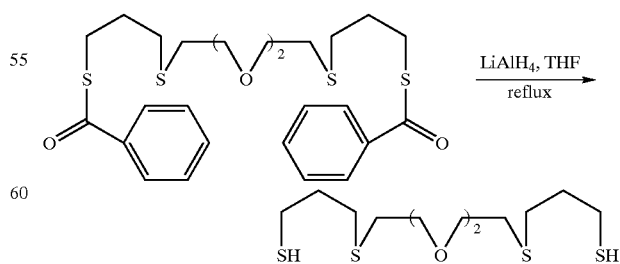

Data verifying the composition was collected using HNMR, and is provided as follows: $^1$HNMR: ($CDCl_3$): 3.7(dt,8H), 2.75(dt2H), 2.0(q,4H).

Example 18

Preparation of 1,5,14,18-tetrathia-8,11-dioxaoctadecane Bonded to Silica Gel About 132 mg of 1,5,14,18-tetrathia-8,1-dioxaoctadecane was dissolved in 10 ml of toluene. Then 194 mg of glycidoxypropyltrimethoxysilane and 6.4 mg of 25% $NaOCH_3$ in methanol was added. The mixture was heated to 80° C. and stirred overnight with a mechanical stirrer. The reaction product was cooled to 50° C. and 2 g of 35–60 mesh silica gel was added to the product and stirred for an additional 3 days. About 2.2 g of 1,5,14,18-tetrathia-8,11-dioxaoctadecane bonded to silica gel was filtered and washed with toluene and $CH_3OH$ and dried. This process is represented schematically below:

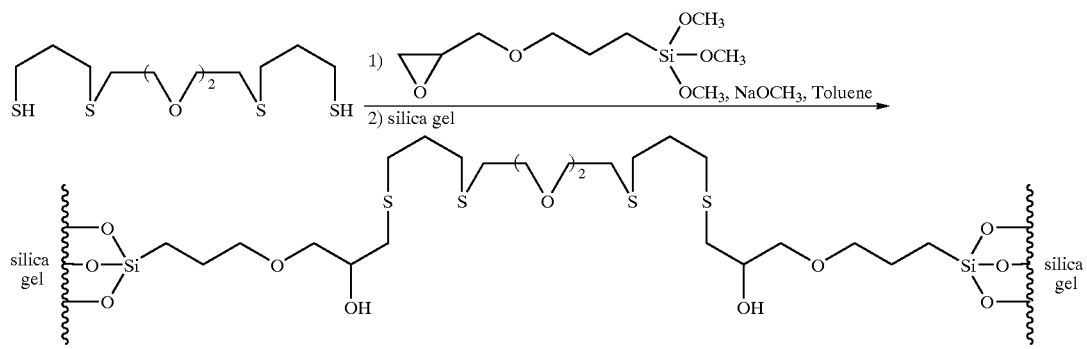

Example 19

Preparation of 4-allyloxy-1,10-dithia-18-crown-6

Into a solution containing 1600 ml of $CH_3CN$ and 40.6 g of $Cs_2CO_3$ was dropped at 65° C. a mixture of 60 g of ditosylate and 20.6 g of 1,10-dithia-4,7-dioxadecane dissolved in 200 ml of $CH_3CN$. The reaction mixture was refluxed 36 hours. The precipitate was filtered off and the filtrate was concentrated to a predetermined dryness. The residue was purified by column chromatography (aluminum oxide, $CH_2Cl_2$ then $CH_2Cl_2/CH_3COOC_2H_5$ 7/1 v/v). About 10 g (24%) of an allyloxydithiacrown was collected and the compound was used without further purification in the next step. The reaction is shown below:

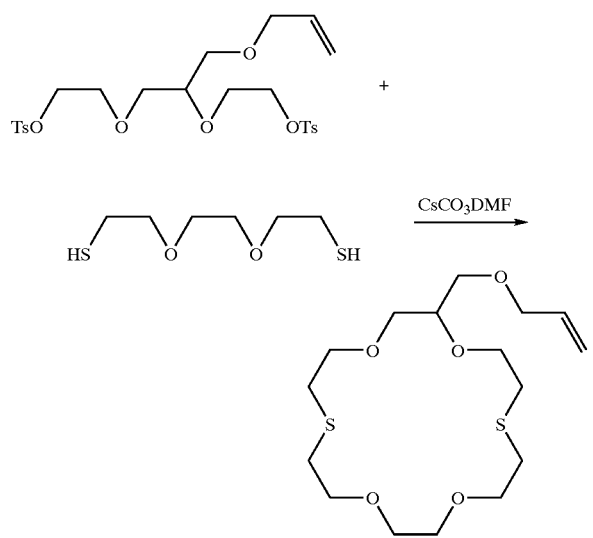

Example 20

Preparation of 4-hydroxypropyloxymethyl-1,10-dithia-18-crown-6

To 3.11 g of the 4-allyloxy-1,10-dithia-18-crown-6 (collected in Example 19) in 10 ml of THF, 40 mg of sodium hydride was added and stirred for 1 hour at room temperature. Next, the THF was removed under reduced pressure and 30 ml of diglyme and 1.18 g of trimethylamine N-oxide dihydrate was added. The mixture was refluxed overnight, the solvent was removed under reduced pressure and the residue was purified by column chromatography, (aluminum oxide, acetone/$CH_2Cl_2$/$CH_3OH$ 40/1 v/v). About 2.6 g (83%) of a hydroxypropyldithiacrown was collected. The reaction is shown generally below:

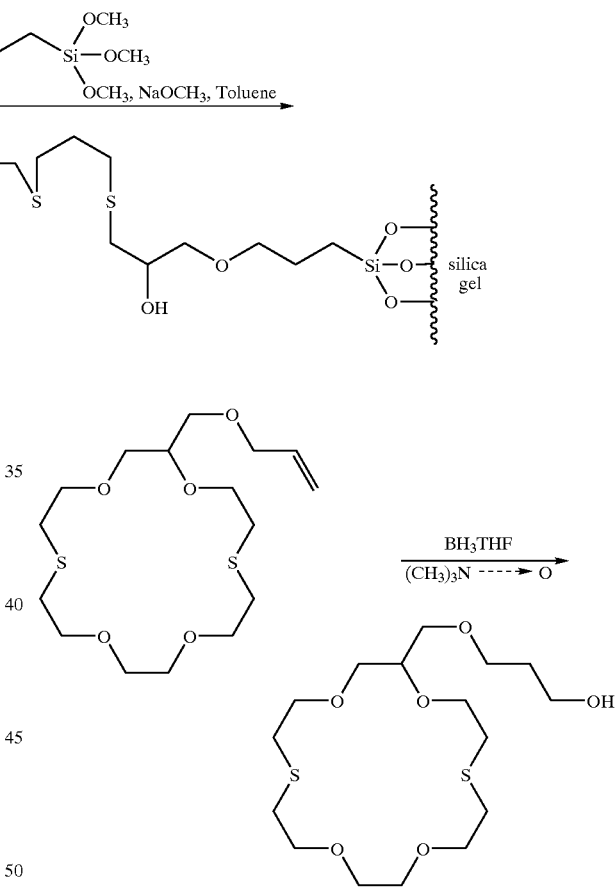

Example 21

Preparation of 1,16-Bis(5'-methoxy-1', 10'-dithia-18-crown-6)-10 alkyloxy-4,7,10,13-tetraoxahexadecane To 560 mg of dissolved hydroxypropyldithiacrown (collected in Example 20) in 15 ml dry THF was added 40 mg of sodium hydride and the mixture was stirred for 1 hour. A solution of 343 mg of ditosylate in 20 ml THF was added dropwise. After addition, the reaction mixture was refluxed 3 days and then cooled, filtered, and evaporated under reduced pressure. The residue was purified by column chromatography, (aluminum oxide, acetone/$CH_2Cl_2$ 5%–10%–15%–20% v/v). An essentially pure 1,16-Bis(5'-methoxy-1', 10'-dithia-18-crown-6)-10-alkyloxy-4,7,10,13-tetraoxahexadecane (35%) was collected, as shown below:

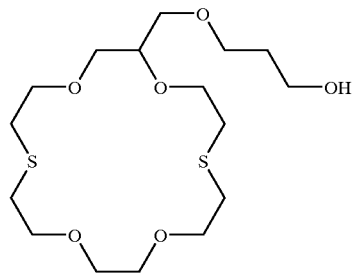
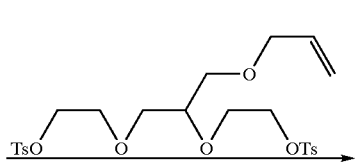

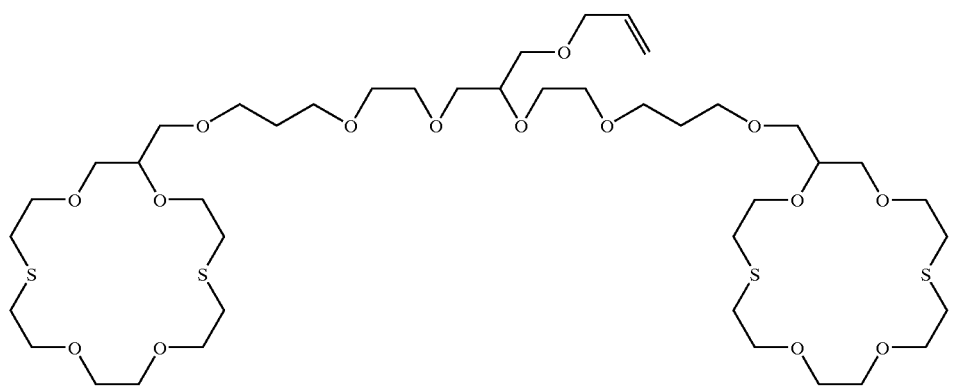

¹HNMR (CDCl₃): 5.989–5.82(m,1H), 5.33–5.16(m,2H), 4.0–3.44(m,58H), 2.88–2.77(m,16H), 1.85(t,4H)HRMS (FAB): m/z for $C_{42}H_{84}O_{15}S_4(M+1)^+$=953.4461, found: 953.4454.

Example 22

Preparation of 1,16-Bis(5'-methyloxy-1'10'-dithia-18-crown-6)-10-hydroxypropyloxymethyl-4,7,10,13-tetraoxahexadecane To 0.58 g of 1,16-Bis(5'-methoxy-11',10'-dithia-18-crown-6)-10-alkyloxy-4,7,10,13-tetraoxahexadecane in 0.5 THF was added 0.21 ml 1 M BH₃-THF. The mixture was stirred at 0° C. for 1 hour, and then further stirred for 4 hours at room temperature. After evaporation of the solvent, 81 mg $(CH_3)_3N^+—O^-$ and 2 ml diglyme was added and refluxed for 2 hours, and then the solvent was removed under reduced pressure. The residue was then purified by column chromatography (aluminum oxide, 5% acetone/CH₂Cl₂), and a 1,16-Bis(5'-methyloxy-1'10'-dithia-18crown-6)-10-hydroxypropyloxymethyl-4,7,10,13-tetraoxahexadecane (34%) was collected, as shown below:

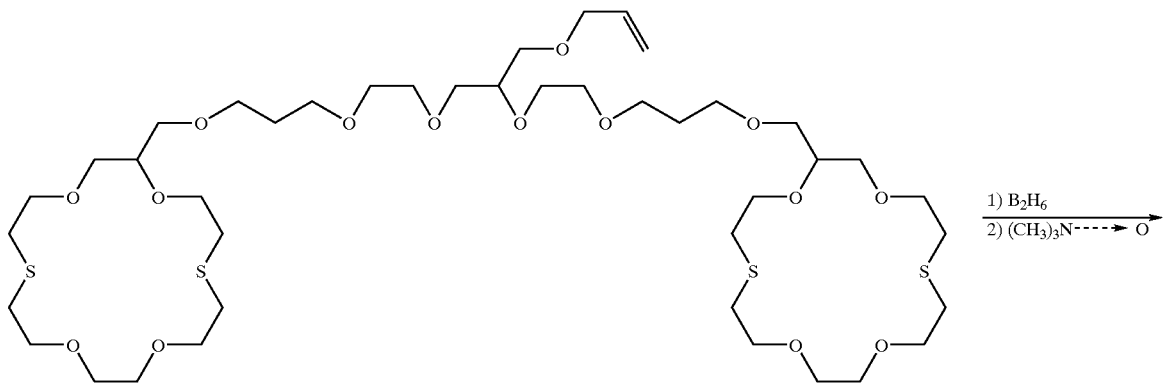

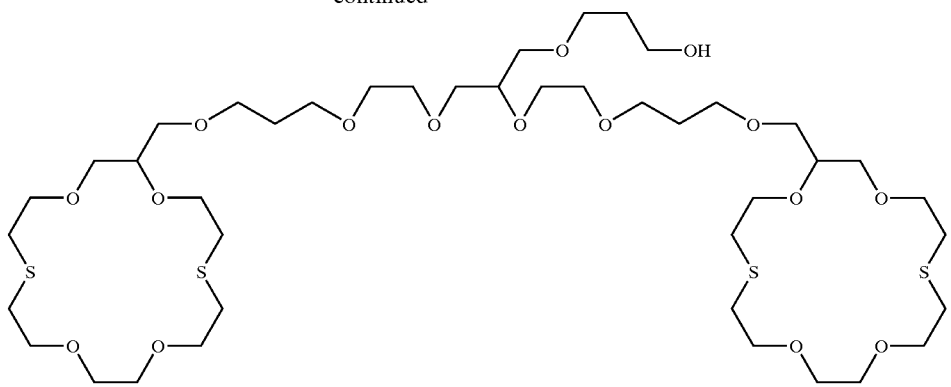

Data verifying the composition was collected using HNMR, and is provided as follows: ¹HNMR (CDCl₃): 3.8?–3.43(m, 59H), 2.88–2.77(m,16H), 1.83(m,6H) MS(FAB): m/z 993 (M+Na)⁺.

Example 23

Preparation of 1,16-Bis(5'-methyloxy-1'10'-dithia-18crown-6)-10-hydroxypropyloxymethyl-4,7, 10,13-tetraoxahexadecane Bonded to Silica Gel A mixture of 364 mg of 1,16-Bis(5'-methyloxy-1'10'-dithia-18crown-6)-10-hydroxypropyloxyrnethyl-4,7,10,13-tetraoxahexadecane, 27 mg NaH (95%), and 10 ml dry 1,4-dioxane was stirred for 1 hour. Tfhen, 375 mg of epoxy silica gel was added and stirred at 90° C. After 3 days, the product was filtered, washed with THF and MeOH. About 426.5 mg of 1,16-Bis(5'-methyloxy-1'10'-dithia-18crown-6)-10-hydroxypropyloxymethyl-4,7,10,13-tetraoxahexadecane bonded to silica gel was obtained. The reaction is shown schematically below:

Example 24

Preparation of Chelidamic Acid Bonded to Polystyrene

A suspension having 3.4 g of Cs₂CO₃ in 150 ml of DMF containing 3 g of dimethyl ester of chelidamic acid was stirred for 1 hour at room temperature. About 2.5 g of Merrifield resin was added and allowed to react for 48 hours at 75° C. After cooling, the solid was filtered off, washed with water, dioxane/water (3/1 v/v), dioxane, and methanol. The resin was dried overnight under vacuum. This intennediate resin in 200 ml of 1,2-dichloroethane was treated with 30 ml of an aqueous solution of 50% potassium hydroxide containing 2 g of ADOGEN 464. The resulting mixture was allowed to react for 48 hours at 70° C. under nitrogen. After cooling down, the solid was filtered off and washed with water, methanol, water, tetrahydrofuran/water (3/1 v/v), tetrahydrofuran, acetone, methylene chloride, and water. The washed product was dried under reduced pressure at 50° C. About 3.0 g of chelidamic acid bonded to poly-

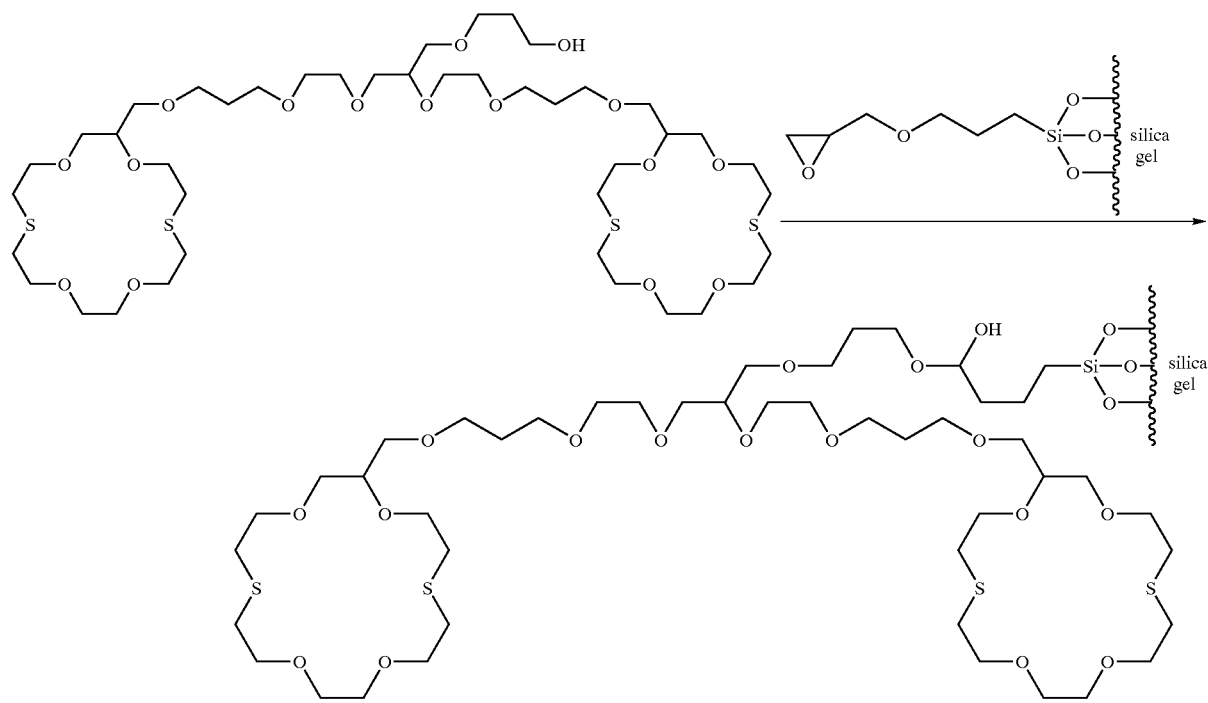

styrene was prepared, the reaction is shown schematically below:

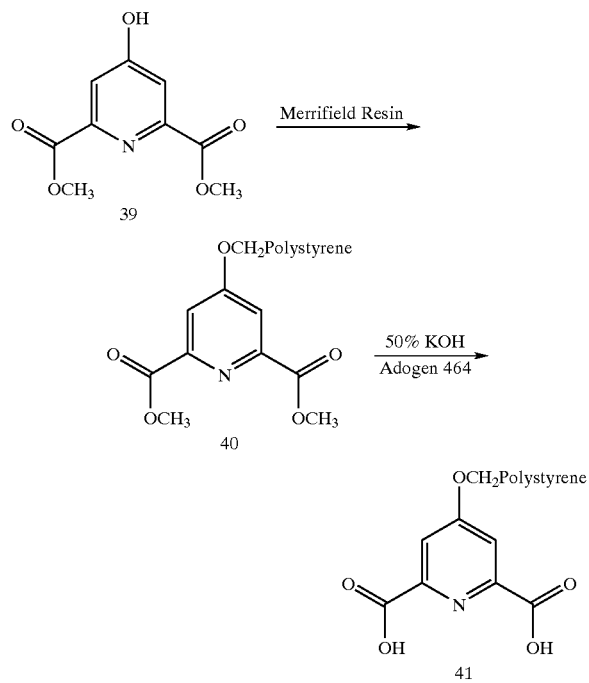

Example 25

Preparation of Iminodi(Methylphosphonic Acid) Bonded to Silica Gel

About 32 ml of 6 N HCl and 13.5 g of phosphorous acid was added and stirred to allow the phosphorous acid to dissolve completely in a 100 ml flask. About 17.7 g of aminopropyltrimethoxysilane was added dropwise at 25° C., refluxed ten minutes, and cooled down to 65° C. Next 25.6 g of formaldehyde was added dropwise, refluxed 1.5 hours, and cooled down to 25° C. The solution was transferred into a 1000 ml flask that was equipped with a mechanical stirrer where 320 ml of 4N HCl was added. Next, 100 g of silica gel was added and the product was heated to 65°–70° C. and kept overnight at that temperature. After cooling, the mixture was filtered, and the solid was washed with $H_2O$, dried under a hood, and dried in a vacuum oven. About 110 g of iminodi(methylphosphonic acid) bonded to silica gel was prepared.

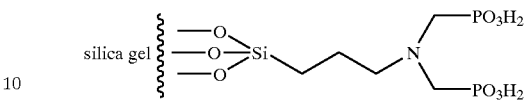

Example 26

Preparation of 4-aminomethyl-1,8-octanediamine Bonded to Silica Gel

A mixture of 5.2 g of 4-aminomethyl-1,8-octanediamine and 0.7 g of glycidoxypropyltrimethoxysilane in 50 ml toluene was stirred at room temperature for 5 hours. Next, 2 g (60–100 mesh) silica gel was added, and stirred at 85° C. for 3 days. The product was then cooled, filtered, and washed with MeOH. About 2.3 g of 4-aminomethyl-1,8-octanediamine bonded to silica gel was prepared. The reaction is shown below:

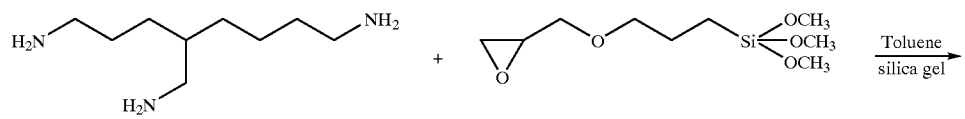

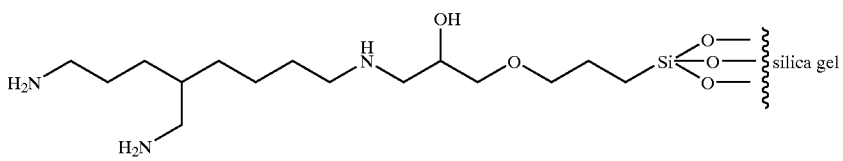

Example 27

Preparation of Penta(Methylphosphonic Acid)-4-aminomethyl-1,8-octanediamine Bonded to Silica Gel A mixture of 2 g of 4-aminomethyl-1,8-octanediamine bonded to silica gel, 1.64 g of phosphorous acid, and 1.08 g of paraformaldehyde in 6N HCl (10 ml $H_2O$, 10 ml conc HCl) was stirred at 65°–70° C. for 3 days. The product was filtered, washed with $H_2O$ and MeOH, and dried to give 2.3 g of penta(methylphosphonic acid)-4-aminomethyl-1,8-octanediamine bonded to silica gel. This reaction is shown below:

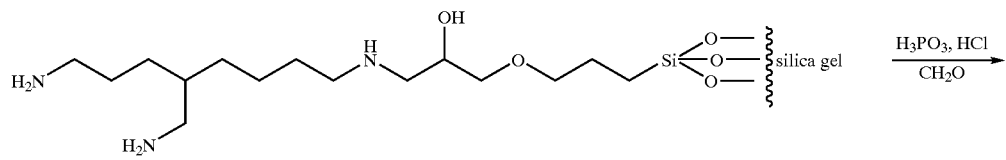

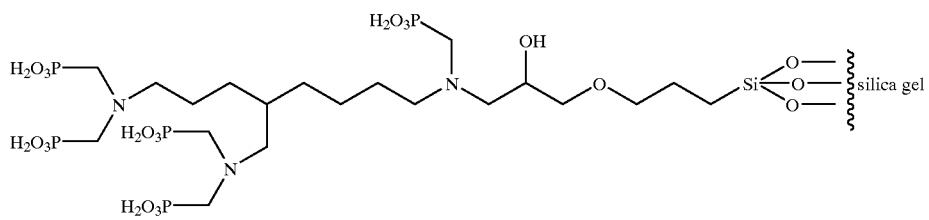

Example 28

Preparation of 4-hydrophenyl Terpyridine Bonded to Silica Gel

To a stirred solution of 1.14 g of 4-hydrophenyl terpyridine in 75 ml DMF was added 350 mg of NaH (60%) and 0.766 g of 3-bromopropyltrimethoxysilane at room temperature. The product was heated at 70° C. for 16 hours and 3 g of silica gel was added. Continued heating was applied for an additional 16 hours. The reaction was then cooled and the solution decanted. The silica gel was washed in THF, filtered, and washed with excess MeOH and THF. Then, the product was dried under reduced pressure for 16 hours at 65° C. About 3.5 g of 4-hydrophenyl terpyridine bonded to silica gel was prepared, the reaction being shown below:

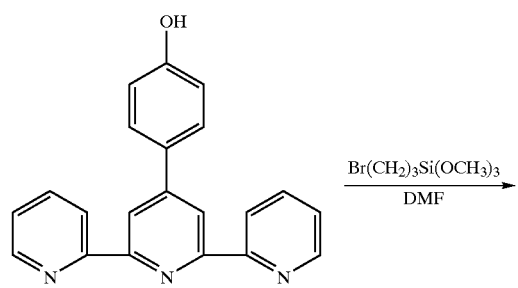

-continued

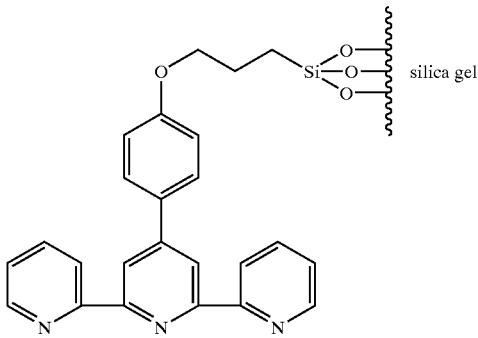

Example 29

Preparation of 5-hydroxymethyl-1,4,7,10-tetaoxadecanediol Ditosylate

A mixture of 15 g of 5-allyloxymethyl-1,4,7,10-tetraoxadecanediol, 0.86 g of 10% Pd/C, and 0.3 g of p-toluenesulfonic acid in 100 ml of ethanol was stirred and heated at 40° C. overnight. The reaction was monitored by TLC (silica plates, $CH_2Cl_2$/MeOH 20:1). When no more starting compound remained, the mixture was filtered off. The filtrate was then evaporated and the residue was purified on column chromatography (silica gel, $CH_2Cl_2$/$CH_3OH$ 40/1 v/v). About 8.18 g (59%) of 5-hydroxymethyl-1,4,7,10-tetraoxadecane-1,10-diol ditosylate was collected, as shown below:

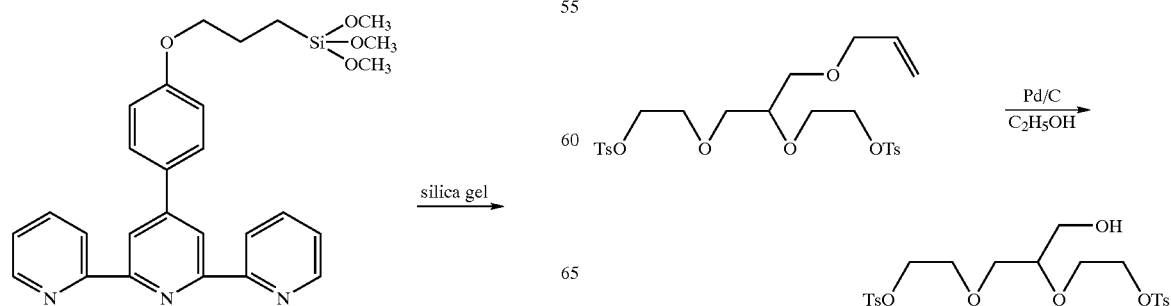

Data verifying the composition was collected using HNMR, and is provided as follows: $^1$HNMR (CDCl$_3$): 7.7(d,4H), 7.3(d,4H), 4.2–3.4(m,13H), 2.1(t,1H).

Example 30

Preparation of 1,10-phenylterpyridine-5-hydroxymethyl-1,4,7,10-tetraoxatetradecane To 100 ml of DMF was dissolved 2.45 g of the hydroxymethyl triethylene glycol ditosylate prepared in Example 29, 3.25 g of terpyridylphenol, and 2.0 g of K$_2$CO$_3$. The mixture was heated at 105° C. for 48 hours and then cooled. After cooling, DMF was removed under reduced pressure. The residue was dissolved in 200 ml of CHCl$_3$ and washed with H$_2$O. The organic layer was dried over MgSO$_4$, filtered, and the CHCl$_3$ layer was concentrated. The crude product was purified using column chromatography (Aluminum oxide, CHCl$_3$/CH$_3$OH 60/1 v/v). About 2.50 g of a 1,10-phenylterpyridine-5-hydroxymethyl-1,4,7,10-tetraoxatetradecane was collected in a 63% yield. The formulation is shown schematically below:

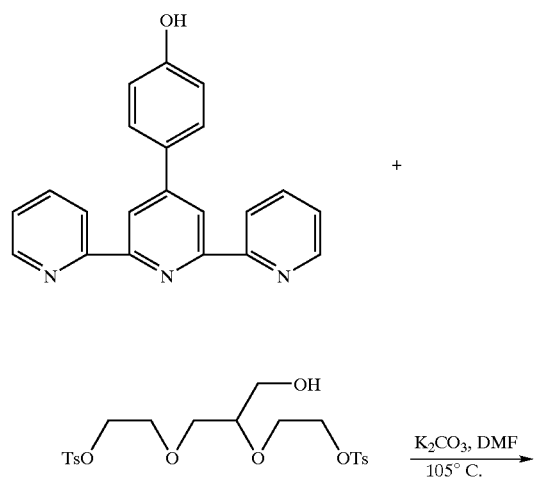

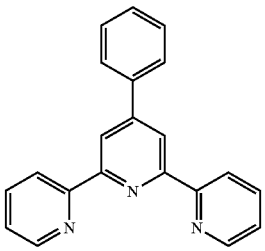

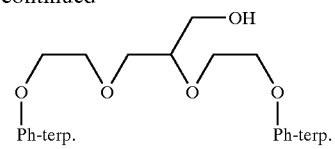

Data verifying the composition was collected using HNMR, and is provided as follows: $^1$HNMR (CDCl$_3$): 8.8–8.5(m, 12H), 7.7–7.6(m,8H), 7.3(d,4H), 7.0(d,H), 4.2–3.0(m,13H), 2.1 (t,1H).

Example 31

Preparation of 1,10-phenylterpyridine-5-hydroxymethyl-1,4,7,10-tetraoxatetradecane Bonded to Silica Gel About 1.20 g of a 1,10-phenylterpyridine-5-hydroxymethyl-1,4,7,10-tetraoxatetradecane prepared in accordance with Example 30 was heated with 0.8 g of an epoxy silica gel, 30 ml of dioxane, and 80 mg of NaH at 85° C. for 48 hours. After cooling, the silica gel was washed with an excess of CH3OH and dried under reduced pressure at 55° C. overnight. About 0.84 g of 1,10-phenylterpyridine-5-hydroxymethyl-1,4,7,10-tetraoxatetradecane bonded to silica gel was collected. The reaction is shown schematically below:

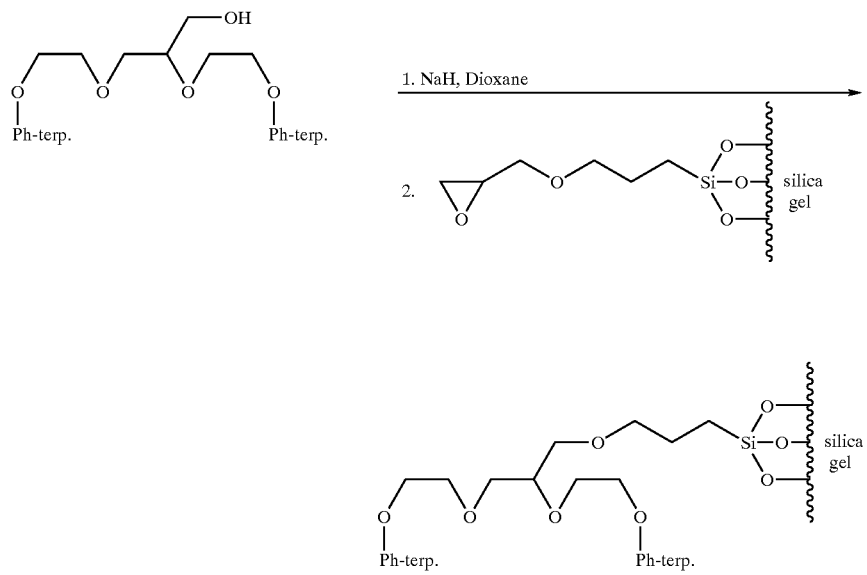

Example 32

Preparation of [4'-(2,2',6', 2"-terpyridine) phenyloxy]ethoxy-ethoxy-ethanol A mixture of 5.09 g of terpyridylphenol, 3.91 g of (chloroethoxy)ethoxyethanol, and 3.8 g of potassium carbonate was heated in 130 ml DMF at 120° C. overnight. The insoluble material was filtered off and washed with DMF. The filtrate was then concentrated under vacuum and the residue was co-evaporated with 100 ml of toluene twice. Finally, the residue was dissolved in toluene, washed with $H_2O$, dried over $MgSO_4$, filtered, and concentrated to give 7.51 g of a thick light brown oil which solidified upon standing overnight. The solid was then crushed, stirred in $Et_2O$, filtered, dried in the air to give 5.81 g (83%) of a [4'-(2,2',6',2"-terpyridine) phenyloxy]ethoxy-ethoxy-ethanol composition. The reaction is shown below:

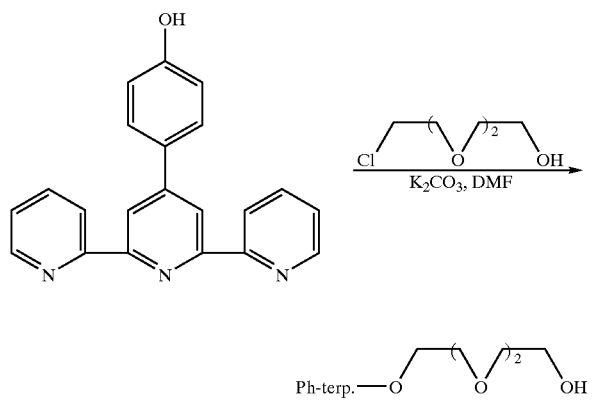

Data verifying the composition was collected using HNMR, and is provided as follows: $^1$HNMR(CDCl$_3$): 3.65(t,2H), 3.70–3.80(m,6H), 3.92(t, 2H), 4.21(t,2H), 7.06(d,2H), 7.35 (m,2H), 7.89(m,4H), 8.66–8.75(m,6H).

Example 33

Preparation of tris-{[4'-(2,2',6',2"-tepyridine) phenyloxy] ethoxy-ethoxy-ethoxy} Pentaerythrityl-Bromide About 4.25 g of [4'-(2,2',6',2"-terpyridine) phenyloxy] ethoxy-ethoxy-ethanol prepared in Example 32, 1.14 g of pentaerythrityl tetrabromide, and 0.97 g of potassium hydroxide was heated in 35 ml of DMSO at 60° C. for 36 hours. After cooling, the reaction mixture was poured onto a stirring mixture of ice/$H_2O$. A solid was collected by filtration and washed with water. After the solid was dissolved in CHCl$_3$, 2N HCl was added. A bright yellow solid formed and was collected by filtration. Next, the solid was stirred with 3N NaOH until the bright yellow color faded to off-white. Then the product was extracted with CHCl$_3$ and filtered. To the insoluble material was added water and then it was extracted with CHCl$_3$. The above procedure was repeated from 3 to 4 times, and the combined chloroform layers were dried over MgSO$_4$, filtered, and concentrated to give 2.50 g of a pale-brown thick oily tris-{[4'-(2,2',6',2"-tepyridine)phenyloxy] ethoxy-ethoxy-ethoxy} pentaerythrityl-bromide. The reaction is shown below:

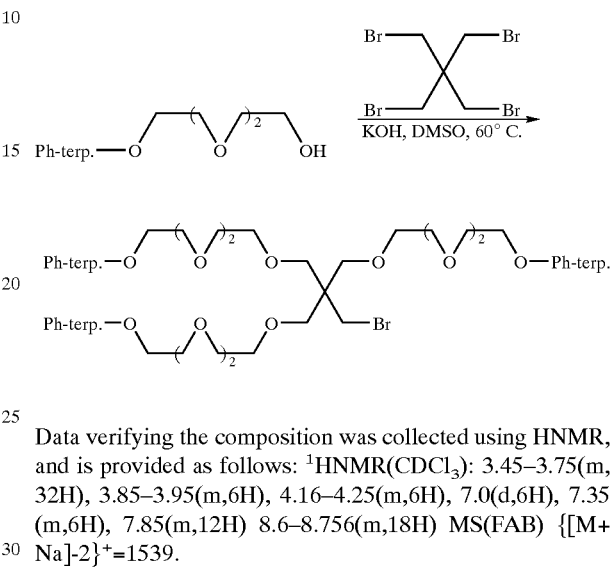

Data verifying the composition was collected using HNMR, and is provided as follows: $^1$HNMR(CDCl$_3$): 3.45–3.75(m, 32H), 3.85–3.95(m,6H), 4.16–4.25(m,6H), 7.0(d,6H), 7.35 (m,6H), 7.85(m,12H) 8.6–8.756(m,18H) MS(FAB) {[M+Na]-2}$^+$=1539.

Example 34

Preparation of tris {[4'-(2,2',6',2"-terpyridine) phenyloxy]ethoxy-ethoxy-ethoxy}pentaerythrityl-tetraethylene Glycol To a preheated solution (40° C.) of 2.47 g of tris-{[4'-(2, 2',6',2"-terpyridine)phenyloxy)ethoxy-ethoxy-ethoxy}-pentaerythrityl bromide prepared as in Example 34 and 40 ml of tetraethylene glycol was added 0.75 g of sodium (cautiously added piece by piece). The reaction mixture was heated at 125° C. overnight. After cooling, the reaction mixture was poured into 300 ml of stirred $H_2O$. Crude product was extracted by CHCl$_3$ (150 ml×3), dried over MgSO$_4$, filtered, and concentrated to give 2.39 g of a brown oil which was redissolved in 6 ml of CHCl$_3$ and treated with 2N HCl. A greenish sticky material formed that was separated from the top of the aqueous phase by decantation, and washed with a small amount of 2N HCl. To the residue was added 3N NaOH to pH 11 and the product was extracted with CH$_2$Cl, dried over MgSO$_4$, filtered, and concentrated to give 1.60 g (61%) of a yellow oily tris{[4'-(2,2',6',2"-terpyridine)phenyloxy]ethoxy-ethoxy-ethoxy}penta-erythrityl-tetraethylene glycol. The reaction is shown below:

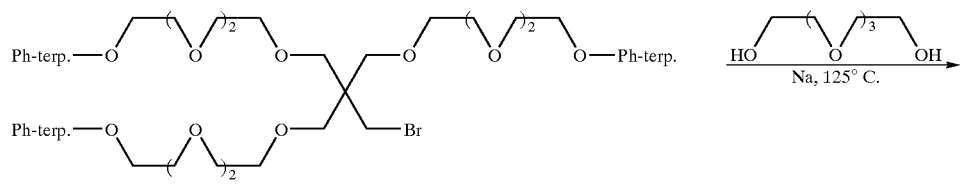

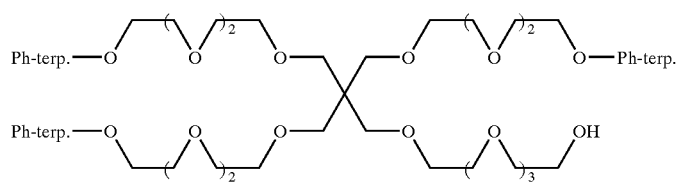

Data verifying the composition was collected using HNMR, and is provided as follows: $^1$HNMR(CDCl$_3$): 3.4–3.75(m, 48H, including 25 singlets at 3.44 & 3.61), 3.86(t,6H), 4.16(t,6H), 7.0(m,6H), 7.31(m,6H), 7.84(m,12H), 8.58–8.72 (m, 8H) MS(FAB) [(M+Na)–1]$^+$=1652.

Example 35

Attachment of tris-{[4'-(2,2',6',2''-terpyridine) phenyloxy]ethoxy-ethoxy-ethoxy} Pentaerytrityl Tetraethylene Glycol to Silica Gel To a preheated solution of 0.8 g tris-{[4'-(2,2',6',2''-terpyridine)phenyloxy]ethoxy-ethoxy-ethoxy} pentaerytrityl tetraethylene glycol in 30 ml dioxane was added 0.09 g of NaH cautiously. After stirring at room temperature for 10 minutes, 0.82 g of glycidyl-silica gel was added, and the temperature was brought up to 80° C. After stirring overnight at 80° C., the reaction was quenched by the addition of CH$_3$OH. The silica gel with tris-{[4'-(2,2',6',2''-terpyridine)phenyloxy]ethoxy-ethoxy-ethoxy} pentaerytrityl tetraethylene glycol attached thereto was then collected by filtration, washed with H$_2$O, CH$_3$OH, CH$_2$Cl$_2$, CH$_3$OH, and H$_2$O successively, and finally dried in a vacuum oven at 55° C. overnight. About 1.0 g of tris-{[4'-(2,2',6',2''-terpyridine)phenyloxy]ethoxy-ethoxy-ethoxy} pentaerytrityl tetraethylene glycol bonded to silica gel was prepared. The reaction is shown below:

Example 36

Preparation of 3-t-butyldimethylsilyloxymethyl-triethyleneglycolditosylate

A 4.90 g amount of 3-hydroxymethyl-triethylene glycol ditosylate and 1.36 g of imidazole were dissolved in 50 ml of DMF. A solution of 1.51 g of t-butyl dimethyl silylchloride in 20 ml of DMF, was added dropwise into the system. After stirring 2 hours at room temperature DMF was removed under reduced pressure. The residue was purified by a silica gel column eluted with CHCl$_3$/CH$_3$OH (70/1). About 1.77 g of product was obtained. The reaction is shown schematically below:

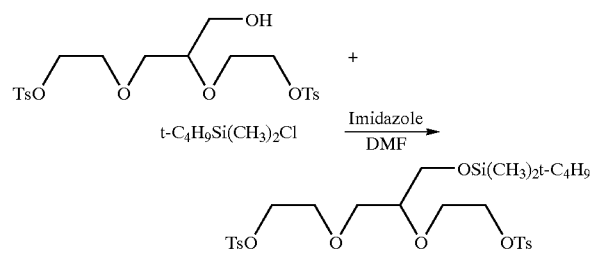

Data verifying the composition was collected using H NMR and is provided as follows: $^1$H NMR (CDCl$_3$) 7.8(d,4H), 6.8(d,4H), 3.4–4.2(m,13H), 2.5(s,6H), 0.8(s,9H), 0.1(s,6H).

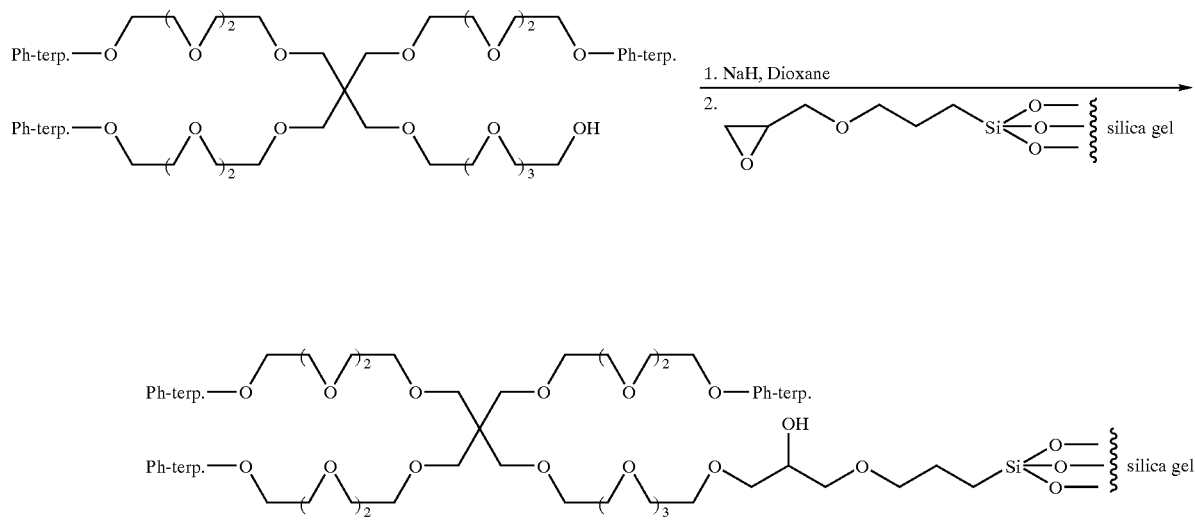

Example 37

Preparation of t-butyldimethyl Silyloxymethyl Triethylene Glycol Terpyridine Dimer Under Argon, 3.16 g of hydroxy methyl terpyridine triethylene glycol dimer was dissolved in 100 ml of dry DMF. Then, 0.32 g of NaH was added to the system and stirred at room temperature for half an hour. Next, 1.51 g of 3-t-butyldimethylsilyloxymethyl-triethylene glycol ditosylate was added to the system in one portion. After stirring at 105° C. for 40 hours, DMF was removed under reduced pressure. The residue was dissolved in CHCl$_3$ and washed with H$_2$O and brine. The CHCl$_3$ layer was separated and dried with MgSO$_4$. After filtration and concentration, the crude product was purified by a silica gel column, and eluted with CHCl$_3$/MeOH (80/1). About 1.8 g of product was obtained. The reaction is shown schematically below:

Data verifying the composition was collected using H NMR and is provided as follows: $^1$H NMR (CDCl$_3$): 8.6(m,24H), 7.8(t,16H), 7.2(t,8H), 7.0(d,8H), 3.5–4.2(m,39H), 0.8(s,9H), 0.1(s,6H).

Example 38

Preparation of Hydroxy Methyl Triethylene Glycol Terpyridine Tetramer

A 0.65 g amount of t-butyl dimethyl silyloxy methyl triethylene glycol terpyridine tetramer and 0.80 g of ammonium fluoride were refluxed in 50 ml of CH$_3$OH for 20 hours. After removing CH$_3$OH, the residue was dissolved in CHCl$_3$ and washed with H$_2$O. The CHCl$_3$ layer was dried with MgSO$_4$. After filtration and concentration, 0.6 g of product was obtained. The reaction is shown schematically below:

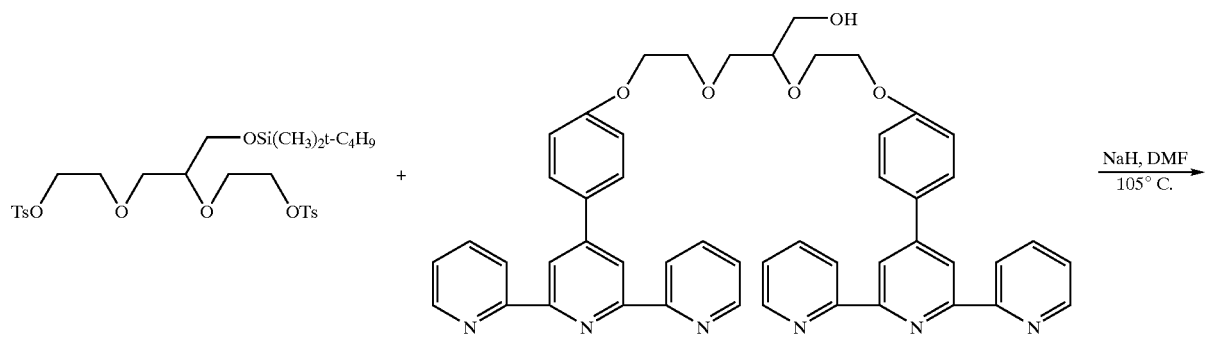

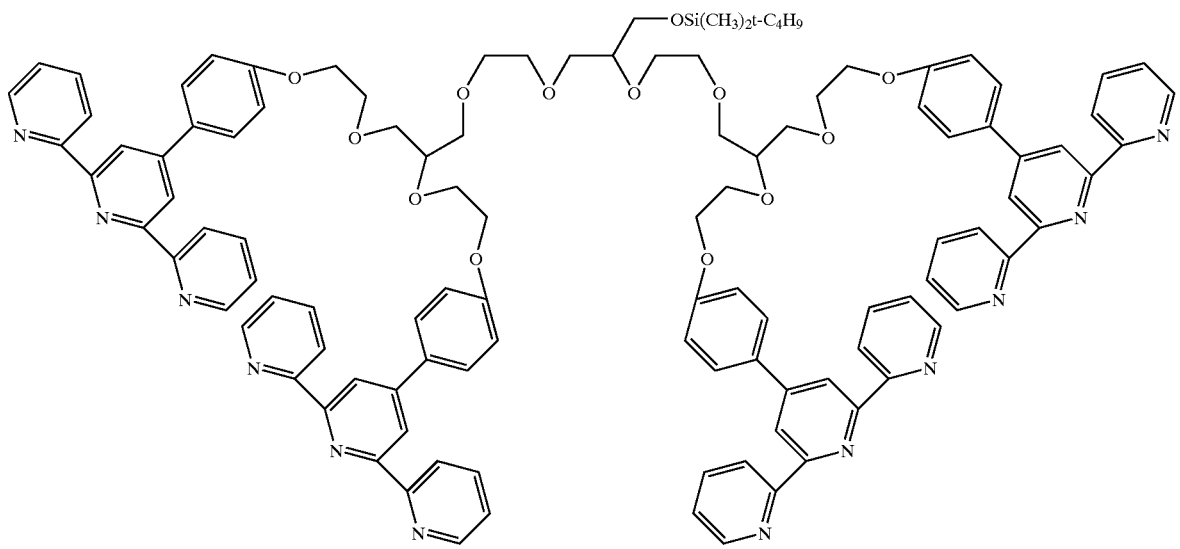

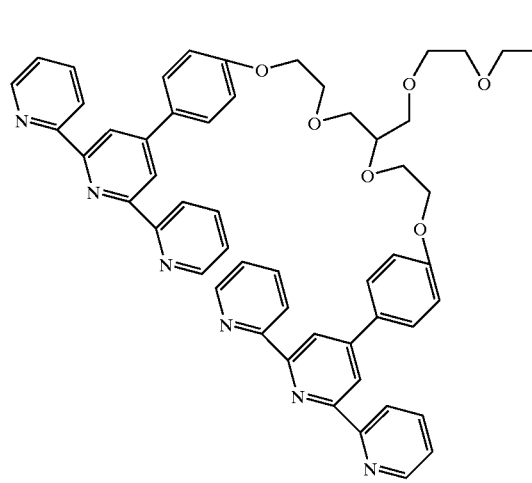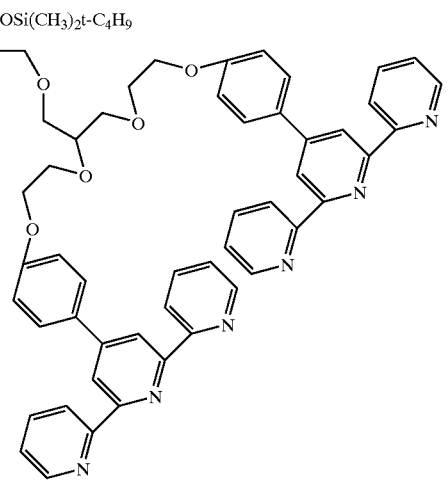

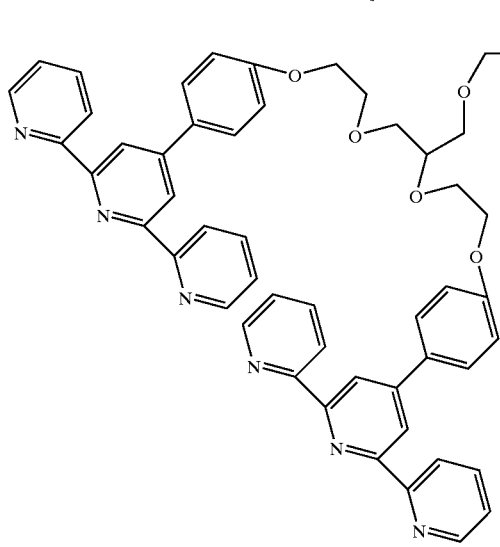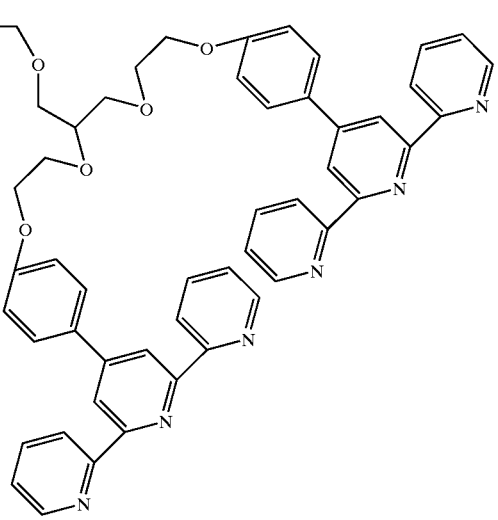

Data verifying the composition was collected using H NMR and is provided as follows: $^1$H NMR (CDCl$_3$): 8.6(m,24H), 7.8(t,16H), 7.2(t,8H), 70(d,8H), 3.5–4.2(m,39H).

Example 39
Preparation of Terpyridine Tetramer Bonded to Silica Gel

A 0.9 g amount of hydroxymethyl terpyridine tetramer was dissolved in 20 ml of dioxane. Under Argon, 0.12 g of NaH were added and stirred for 15 minutes at room temperature. After adding 0.40 g of epoxide modified silica gel, the temperature was raised to 90° C. for 72 hours. Upon cooling, the mixture was filtered and the silica was washed with a large amount of CH$_3$OH. The product was dried in a vacuum oven at 50° C. for 8 hours. The reaction is shown schematically below:

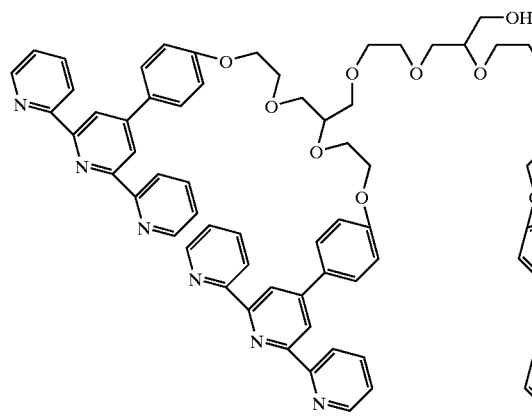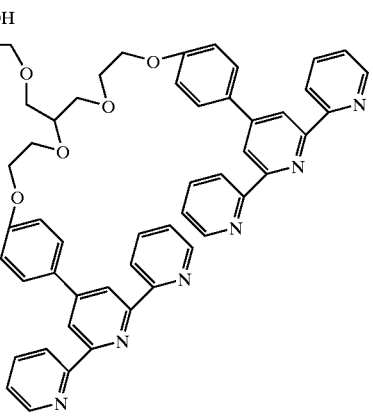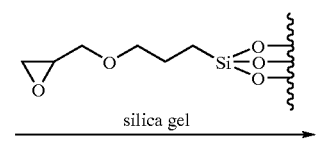

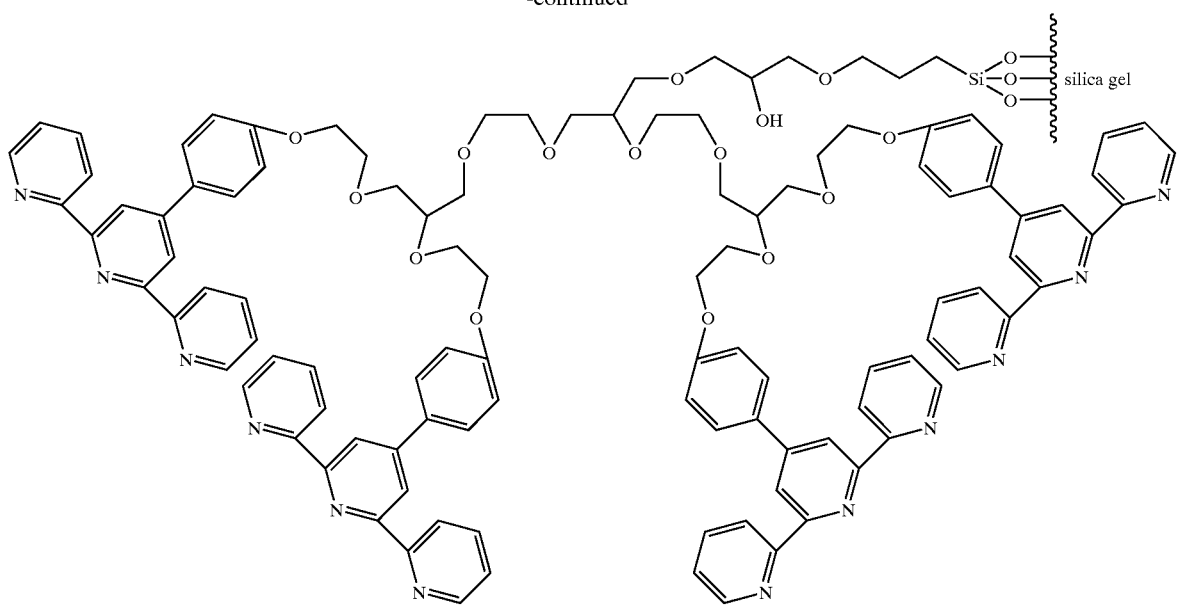

Example 40

Preparation of Triethylene Glycol Tosylate of Dimethyl Ester of Chelidamic Acid

A mixture of 4.22 g of a dimethyl ester of chelidamic acid, 32 g of a triethylene glycol ditosylate, and 4.14 g of $K_2CO_3$ in 100 ml $CH_3CN$ was refluxed for 3 days, cooled, filtered, and evaporated. The residue was purified by column chromatography (silica gel, 2.5% acetone/$CH_2Cl_2$). A triethylene glycol tosylate of dimethyl ester of chelidamic acid (50%) was collected. The reaction is shown below:

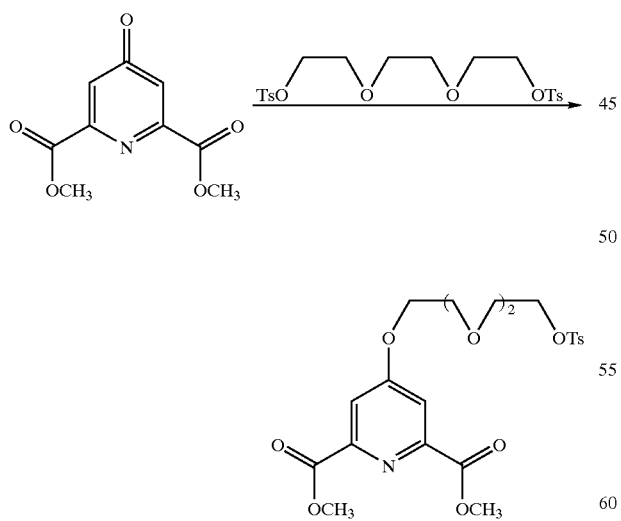

Data verifying the composition was collected using HNMR, and is provided as follows: $^1$HNMR ($CDCl_3$): 7.83 (d, 2H), 7.79 (s, 2H), 7.34 (d, 2H), 4.33–4.18 (m, 8H), 4.02 (s, 6H), 3.92–3.63 (m, 4H), 2.45 (s, 3H).

Example 41

Preparation of 3,6-dioxa-9,12,15-triaza-9,12,15-triethyldodecane-1-O'-chelidamic Acid Dimethyl Ester A mixture of 2.0 g of a triethylene glycol tosylate of dimethyl ester of chelidamic acid of Example 36, 3.0 g of N,N',N"-triethyl-diethylenetriamine and 3.40 g of $Na_2CO_3$ in 100 ml $CH_3CN$ was refluxed for 3 days, cooled, filtered, and evaporated. The residue was purified by column chromatography (silica gel, $CH_2Cl_2$–30% MeOH/$CH_2Cl_2$). A 3,6-dioxa-9,12,15-triamine-9,12,15-triethyldodecane-1-O'-chelidamic acid dimethyl ester (45%) was collected, as shown schematically below:

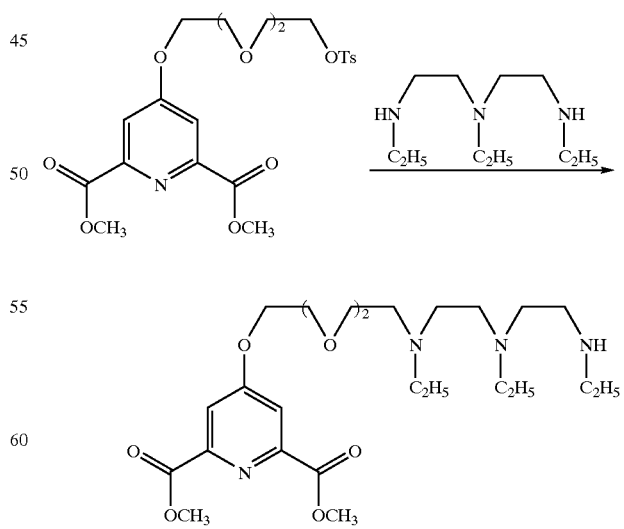

Data verifying the composition was collected using HNMR, and is provided as follows: $^1$HNMR ($CDCl_3$): 7.82(s,2H), 4.32(m,2H), 4.02(s,6H), 3.9(m,2H), 3.74–3.53(m,6H), 2.72–2.53(m,16H), 1.17–0.98(m,9H), MS(FAB): m/z 535 (M+Na)⁺.

Example 42

Preparation of 3,6-dioxa-9,12,15-triaza-9,12,15-triethyldodecane-1-O'-chelidamic Acid About 470 mg of a 3,6-dioxa-9,12,15-triaza-9,12,15-triethyldodecane-1-O'-chelidamic acid dimethyl ester was added to a solution of 1514 mg of KOH in 25 ml CH$_3$OH. The product was stirred at room temperature for 20 hours, the solvent was evaporated, the residue was acidified by adding 3N HCl, and the solvent was again evaporated. A crude chelidamic acid derivative was collected, as shown below:

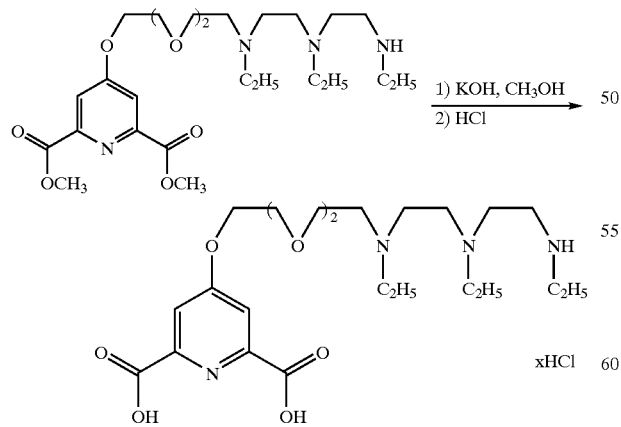

Data verifying the composition was collected using HNMR, and is provided as follows: ¹HNMR (CDCl$_3$): 7.78 (s, 2H), 4.86 (t, 1H), 3.84–2.61 (m, 26H), 1.36 (m, 6H), 0.99 (m, 3H), MS(FAB): m/z 485 (M+1)⁺.

Example 43

Preparation of 3,6-dioxa-9,12,15-triaza-9,12,15-triethyldodecane-1-O'-chelidamic Acid Bonded to Silica Gel About 384 mg of a 3,6-dioxa-9,12,15-triaza-9,12,15-triethyldodecane-1-O'-chelidamic acid (0.65 mmol) as prepared in Example 38 was dissolved in 2 ml H$_2$O and neutralized to pH 7–8 by adding 6N NaOH. To the above solution was added 10 ml of a pH 10 buffer solution and 300 mg of silica gel (60–100 mesh). The mixture was stirred at 45° for 3 days. Next, the silica gel with ligand was filtered off and washed with H$_2$O and CH$_3$OH. About 326 mg of chelidamic acid triethyleneglycoltriethyl diethylenetriamine bonded to silica gel was collected. The structure and reaction are shown below:

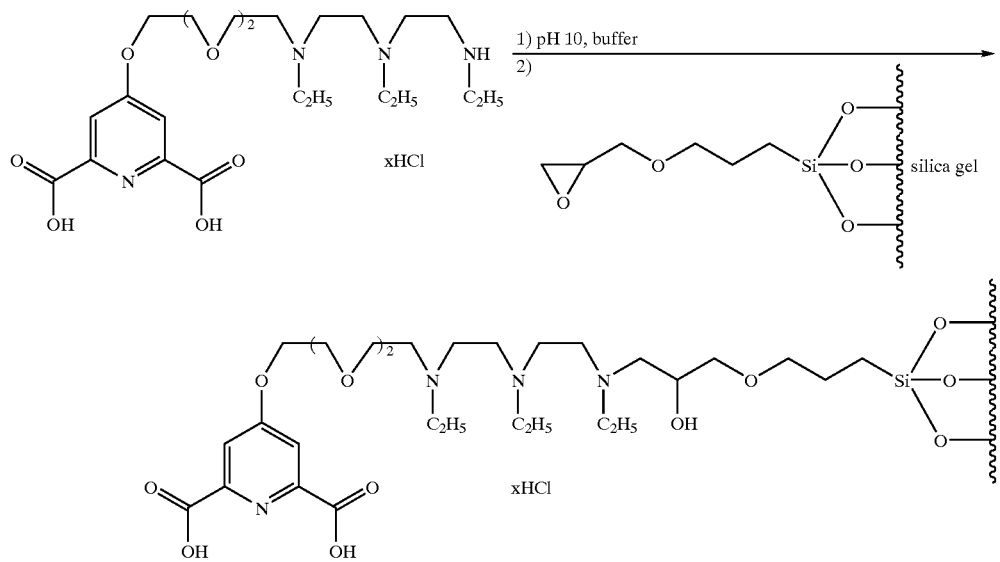

Example 44

Preparation of 9,13-Dithia-3,6,16,19-tetraoxaheneicosane-1,21-diol Ditosylate

To 20 ml of methylene chloride and 5.1 g of triethylamine was added 5.6 g of 9,13-dithia-3,6,16,19-tetraoxaheneicosane 1,21-diol. Then 6.1 g of p-toluenesulfonyl chloride at 0° to 5° C. in 20 ml of methylene chloride was added dropwise. The mixture was stirred overnight at room temperature and then was washed with 50 ml of water. The organic layer was dried over MgSO$_4$. After filtration, the solvent from the filtrate was evaporated and the residue was purified using silica gel column chromatography (CH$_2$Cl$_2$/CH$_3$COCH$_3$) (50:1 v/v). About 8 g (78%) of 9,13-dithia-3,6,16,19-tetraoxaheneicosane-1,21-diol ditosylate was collected. The process step for obtaining this composition is shown schematically below:

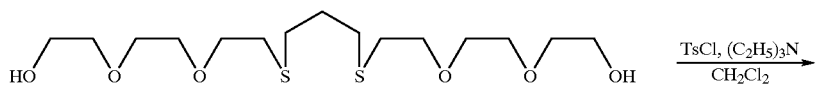

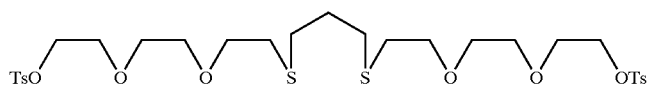

Data verifying the composition was collected using H NMR and is provided as follows ¹HNMR (CDCl$_3$): 1.85(m,2H), 2.45(s,6H), 2.70(m,8H), 3.7–3.5(m, 16H), 4.15(t,4H), 7.35 (d,4H), 7.75(d,4H).

Example 45

Preparation of 1,31-ditrityl 1,5,14,18,27,31-hexathia-8,11,21,24-tetraoxaheneicosatriacontane About 5.97 g of S-trityl-1,3-dithiapropane and 9,13-dithia-3,6,16,19-tetraoxaheneicosane-1,21-diol ditosylate was added to 50 ml of DMF with 9.14 g of cesium carbonate. The mixture was stirred at 60° to 70° C. for 72 hours. This mixture was then cooled down, evaporated under reduced pressure and the residue dissolved in 100 ml of CH$_2$Cl$_2$/Acetone (20/1 v/v). About 3.3 g of 1,31-ditrityl-1,5,14,18,27,31-hexathia-8,11,21,24-tetraoxaheneicosatriacontane was collected. The process steps for obtaining this composition are shown schematically below:

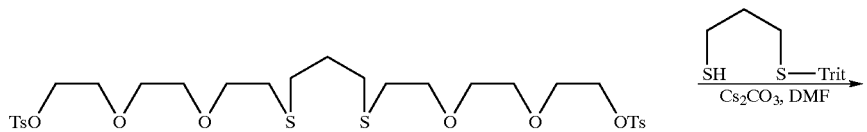

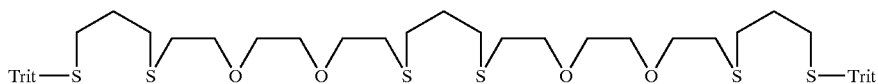

Data verifying the composition was collected using H NMR, and is provided as follows: ¹HNMR: (CDCl$_3$):1.65(m,16H), 1.8(m,2H), 2.25(t,4H), 2.50(t,4H), 2.65(m,12H), 3.80(m, 16H), 7.74–7.70(m,30H).

Example 46

Preparation of 1,5,14,18,27,31-hexathia-8,11,21,24-tetraoxaheneicosatriacontane

A 2.43 g amount of 1,31-ditrityl-1,5,14,18,27,31-hexathia-8,11,21,24-tetraoxaheneicosatriacontane was added to a mixture of 7 ml of methylene chloride and 10 ml of triflouracetic acid and 0.75 ml of triethylsilane. The mixture was stirred at room temperature for 1 hour. Then, 100 ml of methylene chloride was added and the reaction mixture was washed with 100 ml of water. The organic layer was dried over MgSO$_4$. The solution was filtered and the filtrate solvents were evaporated. The crude product was purified on silica gel column chromatography with CH$_2$Cl$_2$/Acetone (5:1 v/v). About 360 mg of 1,5,14,18,27,31-hexathia-8,11,21,24-tetraoxaheneicosatriacontane was collected. The process steps for obtaining this composition are shown schematically below:

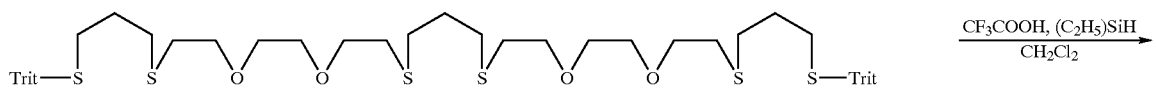

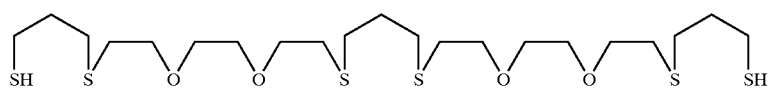

Data verifying the composition was collected using H NMR, and is provided as follows: ¹HNMR: (CDCl₃): 1.47(t,2H), 1.85(m,6H), 2.65(m,20H), 3.65(m,16H).

Example 47

Preparation of 1,5,14,18,27,31-hexathia-8,11,21,24-tetraoxaheneicosatriacontane Bonded to Silica Gel About 280 mg of 1,5,14,18,27,31-hexathia-8,11,21,24-tetraoxaheneicosatriacontane was dissolved in 80 ml of dioxane under nitrogen. Then 46 mg of sodium hydride was added and was stirred for 2 hours. Next, 248 mg of 3-bromopropyltrimethoxysilane was added and was refluxed overnight. Then, 600 mg of silica gel (Grace) grade 646 was added and was stirred at 90° C. for 48 hours. After cooling down, the silica gel was filtered off and was washed with methanol. The product was dried at 50° C. under vacuum. The process is represented schematically below:

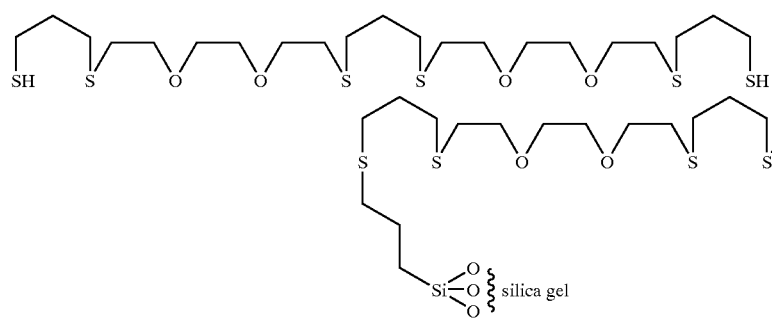

Example 48

Preparation of 1,26-Ditrityl-1,5,9,18,21,26-hexathia-12,15-dioxahexacosane

A mixture of 5.97 g of S-trityl-1,3 propanadithiol and 4.7 g of 4,13-dithia-7,10-dioxa-1,16-hexanadecanediol tosylate and 6.09 g of cesium carbonate was stirred at 60° to 70° C. in 50 ml of DMF during 72 hours. The solvent was removed under vacuum and the residue was dissolved in 100 ml of methylene chloride. The organic layer was washed with 30 ml of brine and dried over anhydrous MgSO₄. Next, the solids were filtered off and the solvent was removed from the solution via evaporation. The residue was purified on silica gel using methylene chloride. About 3 g (41%) of 1,26-ditrityl-1,5,9,18,22,26-hexathia-12,15-dioxa-hexacosane was obtained. The reaction is shown below schematically:

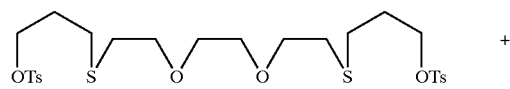

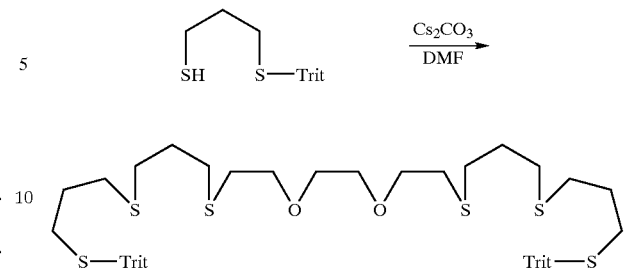

Data verifying the composition was collected using HNMR, and is provided as follows: ¹H NMR(CDCl₃): 1.65(m,4H), 1.80(m,4H), 2.65–2.25(m,20H), 3.8(t,8H), 7.25–7.5(m, 30H).

Example 49

Preparation of 1,5,9,18,22,26-hexathia-12,15-dioxahexacosane

A 2.14 g amount of 1,26 ditrityl-1,5,9,18,22,26-hexathia-12,15-dioxahexacosane was dissolved in a mixture of 9.0 ml of triflouroacetic acid and 9.0 ml of methylene chloride. About 0.7 ml of triethylenesilane was added and stirred at room temperature for a half hour. About 100 ml of methylene chloride was added to the mixture and this was washed with 50 ml of water. The organic layer was then dried with magnesium sulfate and filtered. The solvent was evaporated from filtrate and the residue was purified on silica gel using a mixture of methylene chloride and acetone (5:1 v/v). About 620 mg (58%) of 1,5,9,18,22,26-hexathia-12,15-dioxahexacosane was obtained. The preparation scheme is shown below:

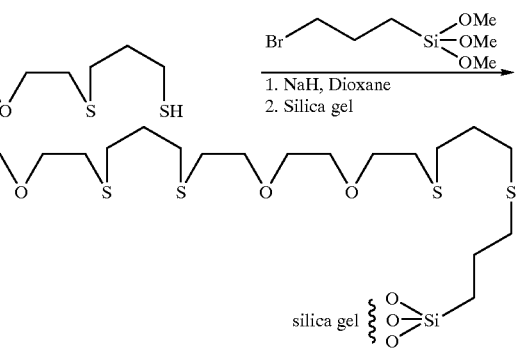

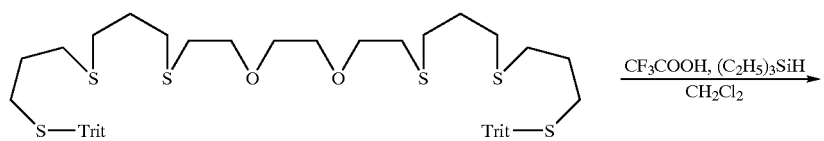

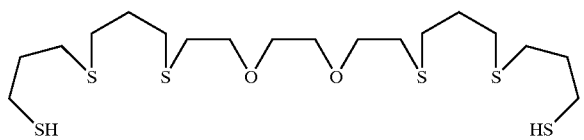

Data verifying the compound was collected using H NMR, and is provided as follows: ¹HNMR (CDCl₃): 1.4(t,2H), 1.8(m,8H), 2.7(m,20H), 3.6(m,8H).

Example 50

Preparation of 1,5,9,18,21,26-hexathia-12,15-dioxahexacosane Bonded to Silica Gel

About 239 mg of 1,5,9,18,21,26-hexathia-12,15-dioxahexacosane was dissolved in 80 ml of dioxane and to this was added 46 mg of sodium hydride. After 2 hours, 255 mg of bromopropyltrimethoxysilane was added and refluxed overnight. Then, 600 mg of silica gel was added and stirred for 8 hours at 90° C. The reaction was cooled down and was filtered. The solid was washed with methanol and dried in a vacuum oven at 60° C. This process is represented schematically below:

aluminum oxide column. About 5.68 g of product was collected. The reaction formula is shown below:

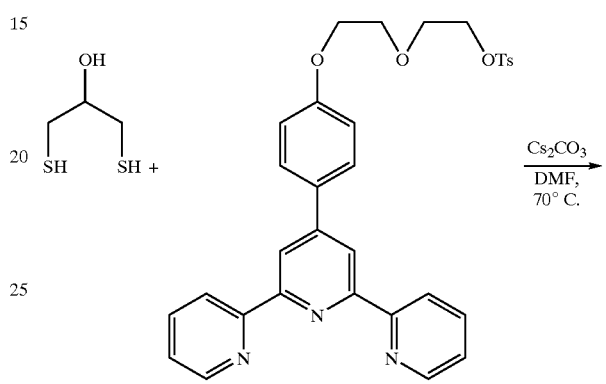

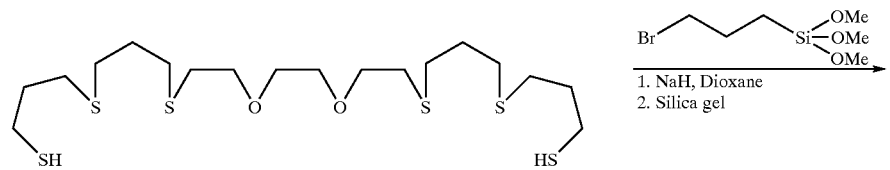

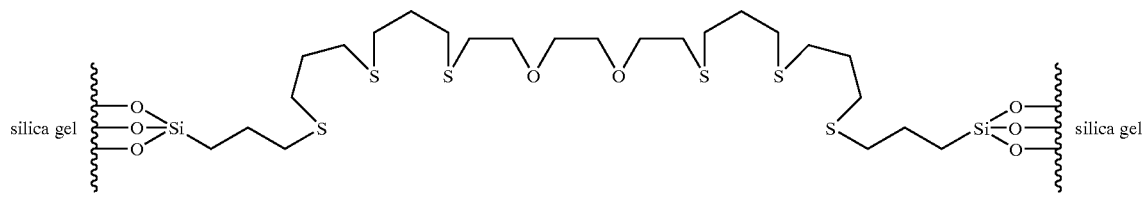

Example 51

Preparation of 1,17-di (4'''-phenyl-4'(2,2':6'2''-terpyridine))-7,11-dithia-1,4,14,17-tetraoxaheptadecane

A 5.68 g amount of tosylate of diethylene glycol phenyl-4'(2,2':6'2''-terpyridine) and 0.62 g of 1,3-dithiapropanol-2 was added to 6.52 g of Cs₂CO₃ in 50 ml of DMF. The mixture was stirred and heated 72 hours at 60° C. DMF was evaporated under reduced pressure and the residue was dissolved in 300 ml of chloroform. The organic layer was washed with 50 ml of water and 50 ml of brine and was dried over MgSO₄ and filtered. From the filtrate the solvent was evaporated and the residue was passed through a short -continued

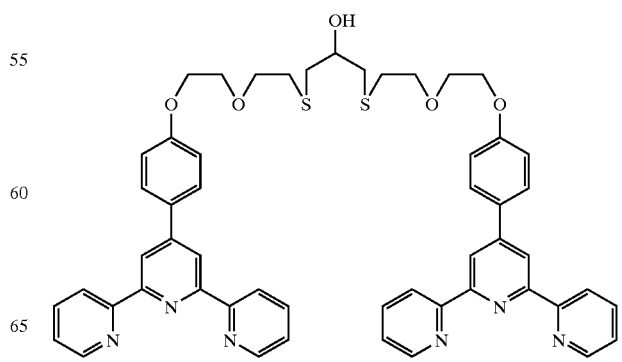

Data verifying the compound was collected using H NMR, and is provided as follows: $^1$HNMR (CDCl$_3$): 1.8(s,1H), 2.6–2.8(m,9H), 3.6(t,4H), 3.8(t,4H), 4.2(t,4H), 7.0(d,4H), 7.3(t,4H), 7.8(t,8H), 8.6–8.8(m,12H).

Example 52

Preparation of 1,17 di-(4'''-phenyl-4'(2,2':6'2''-terpyridine)-7,11-dithia-1,4,14,17-tetraoxaheptadecane Bonded to Silica Gel About 2.0 g of the above compound and 0.22 g of sodium hydride was added to 50 ml of dioxane under nitrogen. After 15 minutes of stirring, 1 g of glycidoxyproyl silica gel was added and this was heated 72 hours at 90° C. After cooling down, 10 ml of CH$_3$OH was added dropwise. Then the modified silica gel was filtered off and was washed with 200 ml of CH$_3$OH. The product was dried 24 hours at 60° C. in a vacuum dryer.

recrystallized from methanol (Yield: 80 g, 62%). The preparation scheme is shown below:

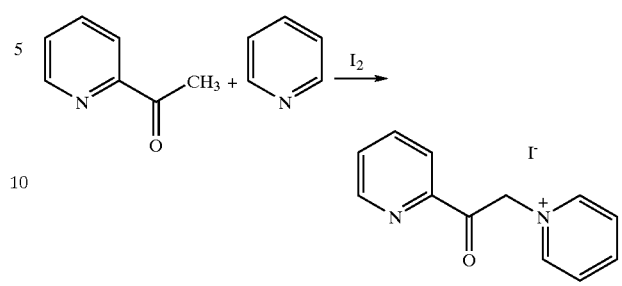

Data verifying the composition was collected using $^1$H NMR, and is provided as follows: $^1$HNMR(CDCl$_3$): 6.5(s, 2H), 7.8(m,1H) 8.1(m,2H), 8.20(t,2H), 8.7(t,1H), 8.8(d,1H), 9.0(d,2H).

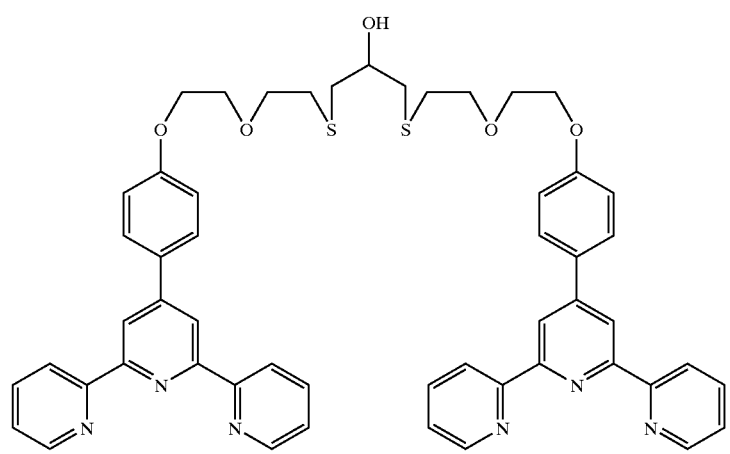

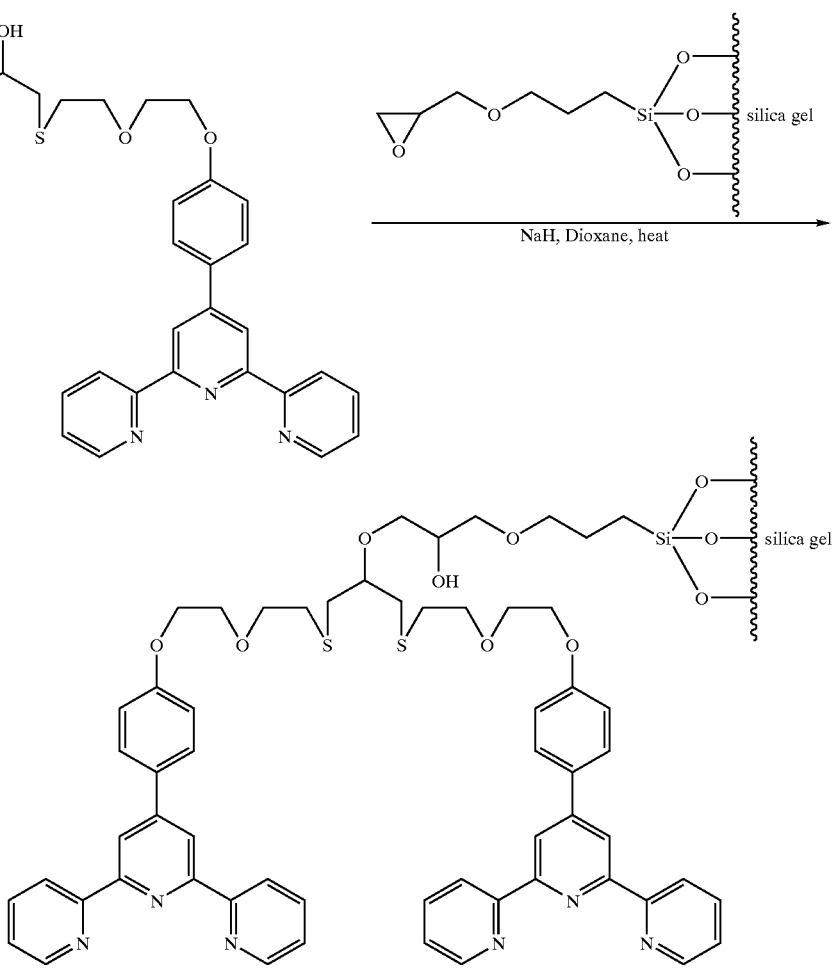

Example 53

Preparation of pyridacyl-2-pyridinium Iodide

To a well-stirred solution of pyridine (400 ml) at room temperature was added 2-acetylpyridine (50 g, 0.41 mmole) and iodine (104 g, 0.41 mmole). The resulting mixture was heated to 90° to 1001C for 5 hours. The mixture was then cooled to room temperature and allowed to stir at room temperature for 16 hours. The mixture was filtered and

Example 54

Preparation of 3,5-Dimethoxy Benzylidene-2-acetylpyridine

To a well stirred solution of NaOH (12 g, 0.3 mmole) in H$_2$O (125 ml) and methanol (250 ml) at 0° C. was added 3,5-dimethoxy benzaldehyde (19 g, 0.11 mmole) followed by a solution of 2-acetylpyridine (14.4 g, 0.12 mmole) in MeOH. The reaction was stirred at 0° C. for 1 hour and at room temperature for 16 hours. The precipitate was filtered and recrystallized from MeOH (Yield: 18 mg, 57%). The preparation scheme is shown below:

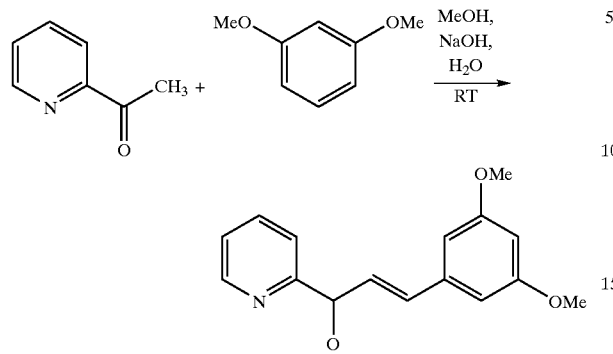

Data verifying the composition was collected using $^1$H NMR and is provided as follows: $^1$H NMR (CDCl$_3$): 3.8(s, 6H), 6.5(s,1H,b) 6.9(s,1H,b), 7.5(m,1H), 7.8–7.9(m,2H), 8.2–8.4(m,2H), 8.7(d,1H).

Example 55

Preparation of 2,6-Bis(2'pyridyl)-4-(3,5-dimethoxyphenyl)pyridine

To a well stirred solution of MeOH (300 ml) and NH$_4$OAc (66 g, 855 mmole) was added 3,5-dimethoxybenzylidene-2-acetylpyridine (17.7 g, 65.8 mmole) and pyridacyl-2-pyridinium iodide (20.5 g, 65.6 mmole). The resulting reaction mixture was refluxed for 6 hours. The reaction mixture was cooled and filtered. The solid residue was washed with MeOH. The product was purified on Al$_2$O$_3$-neutral, and eluted with CH$_2$Cl$_2$/ethyl acetate (1/1) (Yield: 5.4 g, 22%). The preparation scheme is shown below:

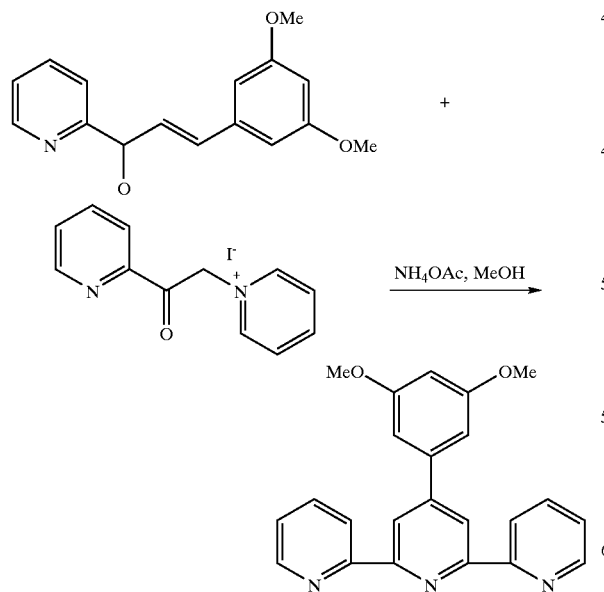

Data verifying the composition was collected using $^1$H NMR, and is provided as follows: $^1$HNMR (CDCl$_3$): 3.9(s, 6H), 7.1(s,1H,b), 7.5(s,2H,b), 7.8(m,2H), 7.9(t,2H), 8.6–8.7 (m,6H).

Example 56

Preparation of 2,6-Bis(2'pyridyl)-4-(3,5-dihydroxyphenyl) Pyridine

To a well stirred solution of 2,6-Bis(2'pyridyl)-4-(3,5-dimethoxyphenyl) pyridine (5.4 g, 140.6 mmole) in acetic acid (105 ml) was added dropwise a solution of HBr (105 ml, 49%) at room temperature. The reaction was heated to 120° C. for 8 hours. The reaction was cooled, made basic with 20% NaOH and brought to pH 12–14. The clear solution was extracted with CH$_2$Cl$_2$ and the pH then brought to 7–8. The solid was filtered and washed with MeOH (Yield: 1.6 g, 32%). The preparation scheme is shown below:

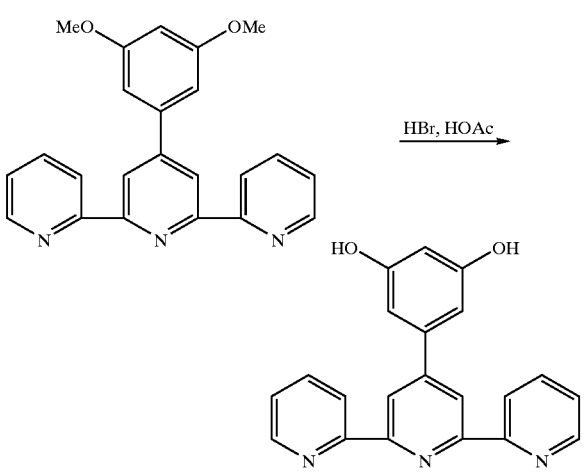

Data verifying the composition was collected using $^1$H NMR and is provided as follows: $^1$H NMR (CDCl$_3$): 6.3(s, 1H), 6.7(s,2H), 7.5(t,2H), 8.0(t,2H), 8.5–8.7(m,6H).

Example 57

Preparation of 7,10,13-tri-p-toluenesulfonyl-7,10, 13-triazatridecane ol

A 30.8 g amount of N,N'N"-Tri-p-tosyldiethylenetriamine was added to 200 ml DMF and 4.4 g of cesium carbonate. At room temperature, 5 g of 6-bromohexanol was added dropwise. The mixture was heated at 80° C. for 40 hours. The solvent was evaporated under reduced pressure and the residue was dissolved in 200 ml of methylene chloride and was washed twice with 50 ml of water and with 50 ml of brine. The organic layer was dried over MgSO$_4$ and was filtered. The solvent was evaporated and the residue was purified on silica gel with ethyl acetate/hexane. About 19 g of 7,10,13-tri-p-toluenesulfonyl-7,10,13-triazatridecane was collected. The process steps for obtaining this composition are shown schematically below:

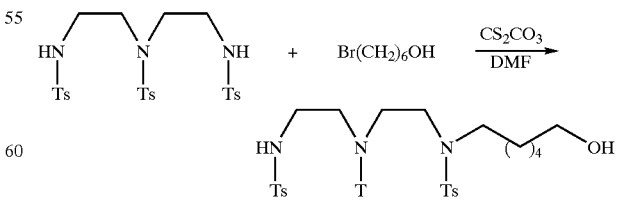

Data verifying the composition was collected using H NMR, and is provided as follows: $^1$H NMR (CDCl$_3$): 1.20–1.40 (m,4H), 1.42–1.60(m,4H), 1.75(t,1H), 2.40–2.50(m,9H), 3.0–3.4(m,10H), 3.50–3.60(t,2H), 5.40(t,1H), 7.30–7.40(m, 6H), 7.60–7.80(m,6H).

Example 58

Preparation of 7,10,13-tri-p-toluenesulfonyl-7,10, 13-triazapentadecaneol

About 9 g of 7,10,13-tri-p-toluenesulfonyl-7,10,13-triazapentadecaneol and 5.3 g of cesium carbonate was added to 200 ml of DMF and the mixture was stirred. After 1 hour 2.5 g of iodoethane in 20 ml of DMF was added dropwise. The mixture was heated for 16 hours at 60° C. After cooling the mixture, the mixture was filtered. From the filtrate, the solvent was evaporated under reduced pressure. To the residue 100 ml of CH$_2$Cl$_2$ was added. The organic layer was washed 3 times with 50 ml of water and was dried over MgSO$_4$. The inorganic salts were filtered off and the organic solvents were evaporated away from the filtrate. The residue was purified on silica gel with CH$_2$Cl$_2$/acetone (20:1 v/v). About 8.1 g of 7,10,13-tri-p-toluenesulfonyl-7,10,13-triazapentadecaneol was collected. The reaction is shown below.

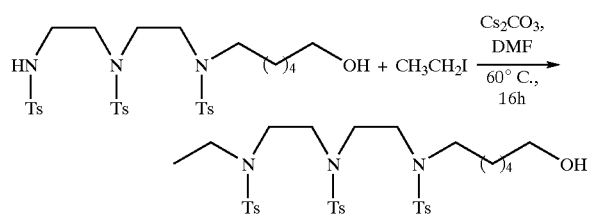

Data verifying the composition was collected using H NMR, and is provided as follows: $^1$H NMR (CDCl$_3$): 1.2(t,31H), 1.21–1.40(m,4H), 1.50–1.60(m,4H), 2.40–2.50(m,9H), 3.20–3.40(m,12H), 3.60(t,2H), 7.30–7.40(m,6H), 7.60–7.80 (m,6H).

Example 59

Preparation of 7,10,13-triazapentadecaneol

About 8 g of 7,10,13-tri-p-toluenesulfonyl-7,10,13-triazapentadecaneol was added to 3.9 g of sodium hydrogen phosphate and 66 g of sodium amalgam in 250 ml of methanol. The mixture was stirred and refluxed for 40 hours. The mixture was cooled down and was filtered. The solvent was evaporated from the filtrate and to the residue 50 ml of CH$_2$Cl$_2$ and 50 ml of 2N HCl was added. After shaking, the acidic layer was separated and neutralized with 20% NaOH. From the mixture, water was evaporated under reduced pressure and to the residue was added 100 ml of methylene chloride. Next the inorganic salts were filtered off. About 2.6 g of crude product was transferred to the next step without further purification. The reaction is shown below.

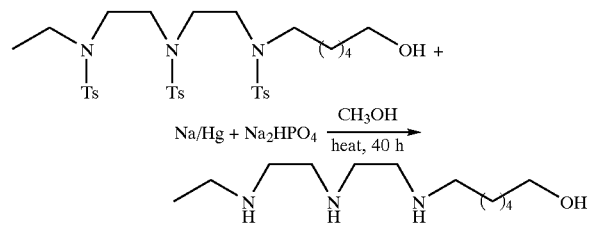

Example 60

Preparation of 7,10,13-tri(t-butoxycarbonyl)-7,10, 13-triazapentadecanol

To a well stirred solution of 7,10,13-triazapentadecanol in CH$_2$Cl$_2$(150 ml), was added (BOC)$_2$O (15 g, 69 mmole). After 16 hours at RT, the solvents were evaporated. The residue was purified on silica gel using CH$_2$Cl$_2$/acetone (20/1 v/v). The product was obtained in quantitative yield. The reaction is shown below:

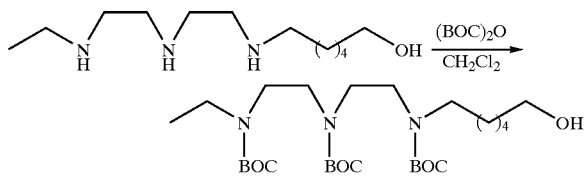

Data verifying the composition was collected using H NMR and is provided as follows: $^1$HNMR (CDCl$_3$): 1.10(t,3H), 1.2–1.6(m,37H), 3.1–3.4(m,12H) 3.60(t,2H).

Example 61

Preparation of 7,10,13-tri (t-butoxycarbonyl)-7,10, 13-triazapentadecanol Tosylate A 6.1 g amount of 7,10,13-tri (t-butoxycarbonyl)-7,10, 13-triazapentadecanol, 100 mg of dimethylaminopyridine, and 4 ml of triethylamine in 100 ml of CH$_2$Cl$_2$ was stirred at 0° C. Dropwise, 2.64 of tosyl chloride in 20 ml of CH$_2$Cl$_2$ was added at 0° to 5° C. The reaction was then stirred overnight at room temperature and then 100 ml of CH$_2$Cl$_2$ was added. The reaction mixture was washed with 30 ml of 2N HCl, 30 ml of water and 30 ml of brine. The organic layer was dried over MgSO$_4$ and was filtered. The solvent was evaporated and the residue from the filtrate was purified using a silica gel column and eluted with ethyl acetate/ hexane (1:2 v/v). About 7.8 g of 7,10,13-tri(t-butoxycarbonyl)-7,10,13-triazapentadecanol tosylate was collected. The reaction is shown below:

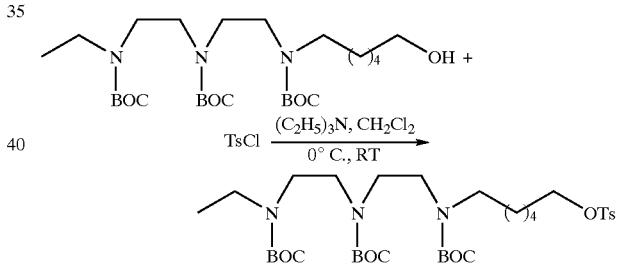

Data verifying the composition was collected using H NMR, and is provided as follows: $^1$HNMR (CDCl$_3$): 1.0–1.70(m, 3H), 2.50(s,3H), 3.00–3.40(m, 12H), 4.0(t,2H), 7.30–7.40 (d,2H), 7.70–7.80(d,2H).

Example 62

Preparation of hexa-t-butoxycarbonyl-(triamine)$_2$- hexane-meta-oxaphenyl-terpyridine About 500 mg of 3,5-dihydroxyphenylterpyridine and 2.1 g of cesium carbonate was stirred 1 hour in 70 ml of DMF at 70° C. Then 2.25 g of 7,10,13-tri-(t-butoxycarbonyl)-7, 10,13-triazapentadecanol tosylate in 20 ml of DMF (dropwise) was added at 70° C. After 16 hours, the mixture was cooled down and the solvent was evaporated under reduced pressure. To the residue 50 ml of CH$_2$Cl$_2$ and 20 ml of H$_2$O were added. The organic layer was separated and was washed with 2% NaOH and 10 ml of brine. The mixture was dried over MgSO$_4$ and the inorganic salts were filtered off. From the filtrate CH$_2$Cl$_2$ was evaporated. About 1.85 g (92%) of crude product was collected and transferred to the next step without further purification. The reaction is shown below:

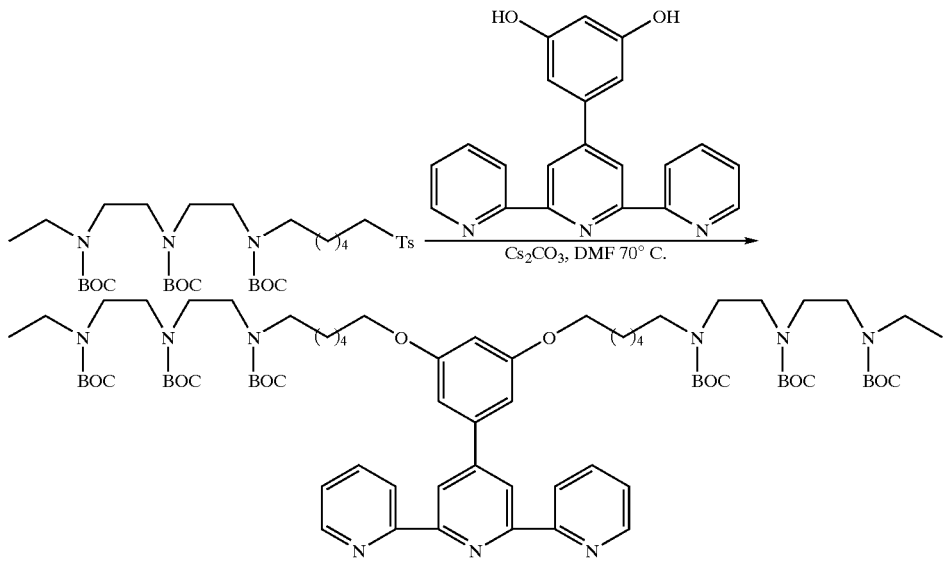

Data verifying the composition was collected using H NMR, and is provided as follows: ¹HNMR (CDCl₃): 1.10(t,6H), 1.30–1.60(m,66H), 1.70(m,4H), 3.10–3.30(m,24H), 4.0(t, 4H), 6.5(s,1H), 6.9(s,2H), 7.30(t,2H), 7.80(t,2H), 8.60–8.70 (m,4H).

Example 63

Preparation of N-ethyl-N'-{2-[3-{3-(3-(27, ethylamino-ethylamino)-ethylamino}-propoxy}-5-[2,2', 6 '2"] terpyridin-4'-yl-phenoxy)-propylamino] ethyl}-ethane-1,2-diamine About 800 mg of the product compound of the previous example was added to 20 ml of triflouroacetic acid and was stirred at room temperature 16 hours. Then, triflouroactic acid was evaporated under reduced pressure. About 1.3 g of crude triflauroacetic salt of the product was obtained. The compound was used in the next step without further purification. The reaction is shown below.

Data verifying the composition was collected using H NMR, and is provided as follows: ¹HNMR (CDCl₃): (free amine), 1.1O(t,6H), 1.25–1.80(m,12H), 2.50–2.80(m,30H), 4.0(t, 4H), 6.50(s,1H), 7.0(s,2H), 7.3(m,2H), 7.90(t,2H), 8.20(m, 6H).

Example 64

Preparation of N-Ethyl-N'-{2-[3-(3-{3-[2-(2-ethylamino-ethylamino)-ethylamino]-propoxy{-5-[2, 2';6'2"]terpyridin-4'-yl-phenoxy)-propylamino]-ethyl}-ethane-1,2-diamine Bonded to Silica Gel A 0.55 g amount of the title compound was neutralized with 5N sodium hydroxide to pH 10. Then 10 ml of buffer solution (pH 10) was added and 600 mg of glycidoxypropyl silica gel was added. The mixture was stirred 40 hours at 40° to 45° C. and was filtered. The modified silica gel was washed with methanol, THF, and then methanol and finally was dried under vacuum at 50° C. The preparation scheme is shown below:

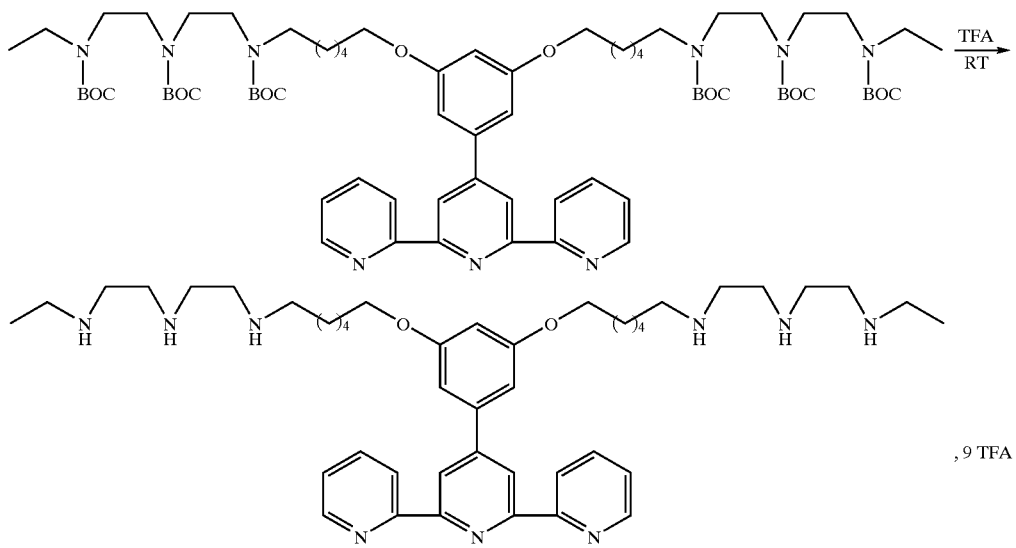

, 9 TFA

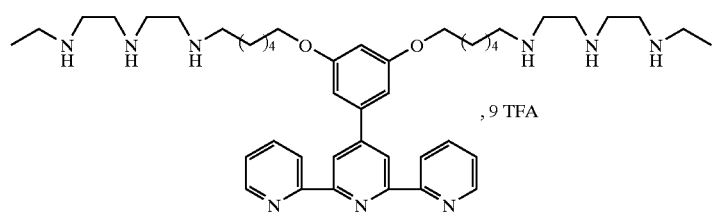 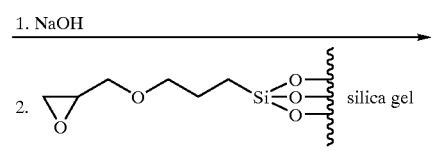

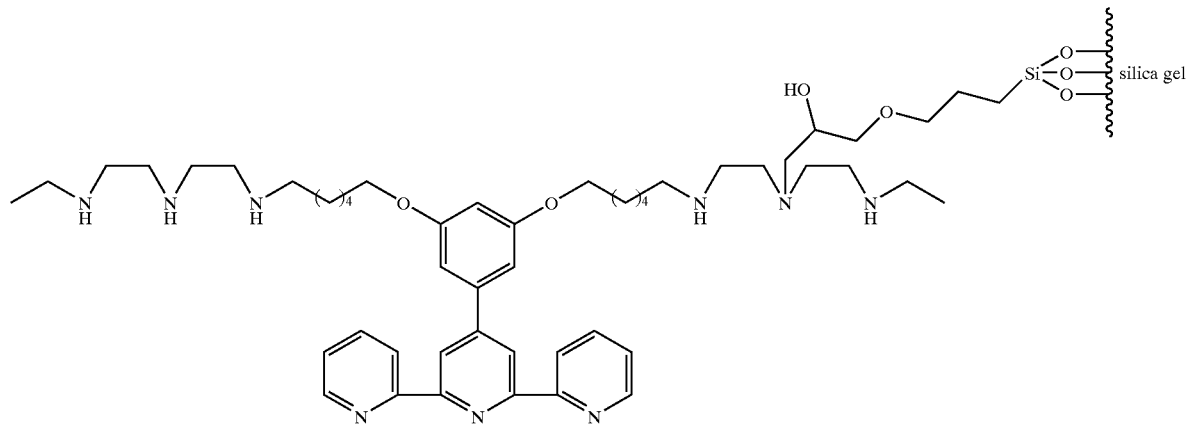

Example 65

Preparation of 1,4,7,13,16,19,25,28,31 nona(p-toluenesulfonyl)-1,4,7,13,16,19,25,28,31-nonaazaheneicosatriacontane About 5 g of 7,10,13 tri (p-toluenesulfonyl)-7,10,13-triaza-4,16-dioxanonadecane-1,19-diol ditosylate, 7.92 g of 1-butoxycarbonyl-1,4,7-tri (p-toluenesulfonyl)-1,4,7-triazaheptane, and 18 g of $Cs_2CO_3$ were mixed with 350 ml of DMF at 70 to 80° C. for 72 hours. The temperature was slowly raised to 130° C. and stirring continued for 36 hours. The mixture was cooled and poured over water with ice, and was extracted with $CH_2Cl_2$. The organic phase was dried over $MgSO_4$, filtered and concentrated under reduced pressure to give 13.52 g of crude product, which was purified on silica gel and eluted with $CHCl_3$/ethyl acetate (50/1 v/v). About 2.5 g of pure product was obtained. The preparation scheme is shown below:

Data verifying the composition was collected using H NMR, and is provided as follows: $^1$HNMR (CDCl$_3$): 2.4(m,27H), 3.2–3.6(m,40H), 7.2–7.4(m,18H), 7.6–7.8(m,18H).

Example 66

Preparation of 1,4,7,13,16,19,25,28,31-nonaazaheneicosatriacontane

A 2.13 g amount of 1,4,7,13,16,19,25,28,31-nona(p-toluenesulfonyl)-1,4,7,13,16,19,25,28,31-nonaazaheneicosatriacontane, 2.13 g of phenol, and 160 ml of a 33% solution of HBr in acetic acid were heated at 70 to 80° C. for 2 days. The solution was then cooled. The acetic acid was removed under vacuum; 100 ml toluene was added and evaporated to remove the rest of the acetic acid. The residue was allowed to partition between 100 ml $CH_2Cl_2$ and 50 ml $H_2O$. The aqueous layer was washed three times with $CH_2Cl_2$ and finally concentrated to ~5 ml: MeOH was then added until the mixture became cloudy. 500 mg (36%) of 1,4,7,13,16,19,25,28,31-nonaazaheneicosatriacontane.9HBr crystallized. The preparation is shown below:

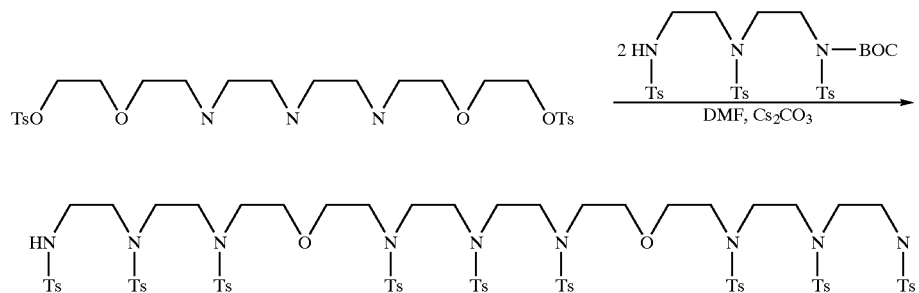

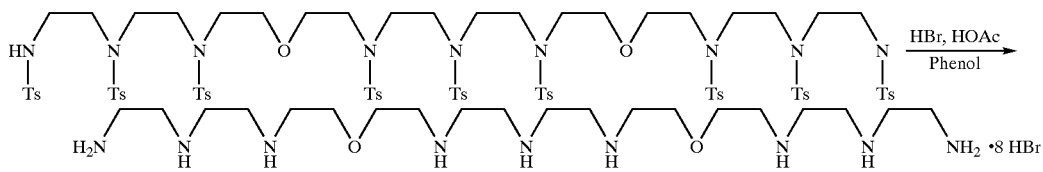

Data verifying the composition was collected using H NMR and is provided as follows: ¹HNMR (CDCl₃): 3.38–3.75(m, 32H), 3.82(t,8H).

Example 67

Preparation of 1,4,7,13,16,19,25,28,31 Nonaazaheneicosatriacontane Bonded to Silica Gel About 1 g (0.85 mmole) 1,4,7,13,16,19,25,28,31-nonaazaheneicosatriacontane9HBr was neutralized with 2 N NaOH solution to pH 8–9. Then, 10 ml of buffer solution (pH 10) and 350 mg glycidoxypropyltrimethoxysilane were added and stirred at 45° C. for 2 days. After cooling, the mixture was filtered and washed with H₂O and MeOH to give product. The preparation scheme is shown below:

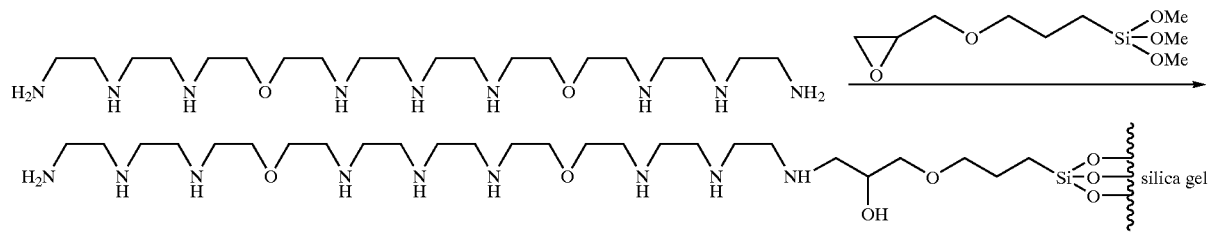

Example 68

Preparation of 1,23-di(t-butoxycarbonyl)-1,4,7,17, 20,23-hexa(p-toluenesulfonyl) 1,4,7,17,20,23-hexaazatricosene A 18.73 g amount of 1-butoxycarbonyl-1,4,7-tri(p-toluenesulfonyl)-1,4,7-triazaheptane was mixed with 3.5 g of 1,9-dibromononane and 37.5 g of Cs₂CO₃ in 1000 ml of DMF at 65 to 70° C. for 22 hours. Stirring was continued at room temperature overnight. The DMF was evaporated under reduced pressure. CH₂Cl₂ was added, the solid was filtered and the solvent was evaporated to give 21.97 g of crude product, which was purified on silica gel and eluted with CH₂Cl₂/ethyl acetate (100/1 to 70/1 v/v). 9.3 g of pure product was obtained. The preparation scheme is shown below:

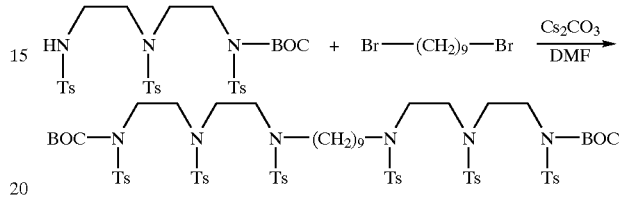

Data verifying the composition was collected using H NMR, and is provided as follows: ¹HNMR (CDCl₃): 1.2(s,10H), 1.4(s,22H), 2.4(m,18H), 3.1(t,4H), 3.4(m,12H), 4.0(m,4H), 7.3(m,12H), 7.7(m,12H).

Example 69

Preparation of 1,4,7,17,20,23-hexa(p-toluenesulfonyl) 1,4,7,17,20,23-hexaazatricosene)

A 3.68 g amount of 1,23-di(t-butoxycarbonyl)-1,4,7,17, 20,23-hexa(p-tolenesulfonyl)-1,4,7,17,20,23-hexaazatricosene and 50 ml of trifluouroacetic acid were stirred at room temperature for 2 hours. The solvent was evaporated under reduced pressure to dryness and the residue was treated with MeOH. The crystals were filtered, rinsed with MeOH and dried overnight in a vacuum oven. About 2.85 g of product was obtained. The preparation scheme is shown below:

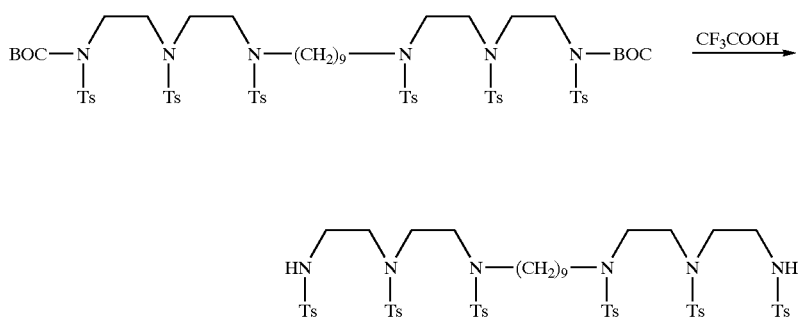

Data verifying the composition was collected using H NMR, and is provided as follows: ¹HNMR (CDCl₃): 1.2(s,14H), 1.5(s,4H), 2.4(s,18H), 3.0–3.3(m,20H), 7.2–7.8(m,24H).

Example 70

Preparation of 16-butoxycarbonyl-10,13,16-tri(p-toluenesulfonyl)-10,13,16-triazahexadecanol A mixture of 14 g of 1-butoxycarbonyl-1,4,7-tri-(p-toluenesulfonyl)-1,4,7-triazaheptane, 7.04 g of 9-bromo-1-nonanol, and 34.25 g of Cs₂CO₃ in 700 ml of DMF was stirred at 65° C. for 24 hours. The mixture was cooled and concentrated under reduced pressure. CH₂Cl₂ was added and the remaining solid was filtered and discarded. The solvent was evaporated to give 22.17 g of crude product which was purified on silica gel and eluted with CH₂Cl₂/ethyl acetate (50/1-20/1 v/v). 7.95 g of pure product was obtained. The preparation scheme is shown below:

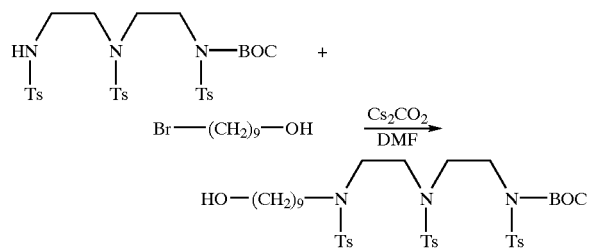

Data verifying the composition was collected using H NMR, and is provided as follows: ¹HNMR (CDCl₃): 1.2–1.7(m, 23H), 2.4(m,9H), 3.1(t,2H), 3.4(m,6H), 3.6(m,2H0, 4.0(m, 2H), 7.45(m,8H), 7.8(m,8H).

Example 71

Preparation of 16-butoxycarbonyl-10,13,16-tri(p-toluenesulfonyl)-10,13,16-triazahexadecaneol Tosylate To 5.47 g of 16-butoxycarbonyl-10, 13,16-tri(p-toluenesulfonyl)-10, 13,16-triazahexadecanol in 200 ml of CH₂Cl₂, 2.95 g of Et₃N was added and the mixture was cooled to 0° C. To the well stirred solution was added dropwise at 0° C. 0.22 g of 4-dimethylaminopyridine and then 1.67 g of p-toluenesulfonyl chloride in 100 ml of CH₂Cl₂ was added. The reaction was continued overnight at room temperature. A 0.04 g amount of 4-dimethylaminopyridine and 0.33 g of p-toluenesulfonyl chloride were added at 7° C. and stirring was continued for 4 hours. The mixture was extracted with water twice. The organic layers were dried over MgSO₄, filtered and evaporated under reduced pressure and eluted with CH₂Cl₂ and CH₂Cl₂/ethyl acetate (100/1 v/v). About 4.21 g of product was obtained. The preparation scheme is shown below:

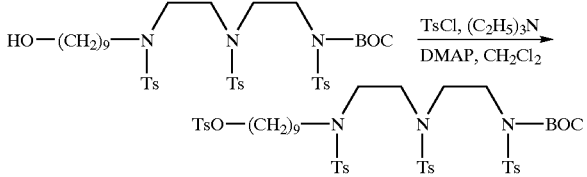

Data verifying the composition was collected using H NMR, and is provided as follows: ¹HNMR (CDCl₃): 1.3(m,14H), 1.4(m,9H), 2.45(m,12H), 3.05(t,2H), 3.4(m,6H), 4.0(m,4H), 7.35(m,8H), 7.8(m,8H).

Example 72

Preparation of 1,55-di(t-butoxycarbonyl)-1,4,7,17, 20,23,33,36,39,49,52,55-dodecane(p-toluenesulfonyl)-1,4,7,17,20,33,36,39,49,52,55-dodecanazapentapentacontane To a well stirred mixture of 2.67 g of 1,4,7,17,20,23-hexa (p-toluenesulfonyl)1,4,7,17,20,23-hexaazatricosene in 150 ml of DMF was added 5.55 g of Cs₂CO₃. The mixture was stirred at room temperature for 0.5 hours. 4.71 g of 16-butoxycarbonyl-10,13,16-tri(p-toluenesulfonyl)-10,13, 16-triazahexadecanol in 75 ml of DMF was added dropwise at room temperature. After addition was completed, the temperature was raised to 70° C. and stirring was continued for 24 hours. The reaction mixture was cooled and DMF was evaporated under reduced pressure. The residue was washed with CH₂Cl₂, the solid was filtered and discarded, and the solution was concentrated under reduced pressure to give 7.93 g of crude product, which was purified on silica gel and eluted with CH₂ClI₂/ethyl acetate (50/1 v/v). About 3.1 g of pure product was obtained. The preparation scheme is shown below.

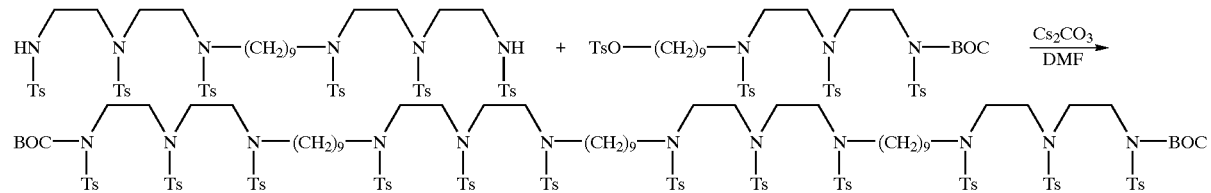

Data verifying the composition was collected using H NMR, and is provided as follows: ¹HNMR (CDCl₃): 1.2(s,30H), 1.35(m.18H), 1.5(m,12H), 2.4(m.36H), 3.0–3.5(m,40H), 4.0 (t,4H), 7.3(m,24H), 7.8(m,24H).

Example 73

Preparation of 1,4,7,17,20,23,33,36,39,49,52,55-dodecaneazapentapentacontane

About 1.5 g 1,55-di(t-butoxycarbonyl)-1,4,7,17,20,23,33, 36,49,52,55-dodecane {p-toluene sulfonyl)-1,4,7,17,20,33, 36,39,49,52,55-dodecaneazapentapentacontane, 1.22 g of phenol, and 100 ml of a 33% solution of HBr in acetic acid were heated at 70 to 80° C. for 2 days. After cooling the purple precipitate was isolated by filtration and washed thoroughly with Et₂O to give 1,4,7,20,23,33,36,39,49,52, 55-dodecaneazapentopentacontane 12HBr (100% yield). The preparation is shown below:

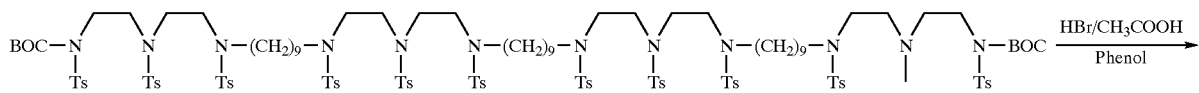

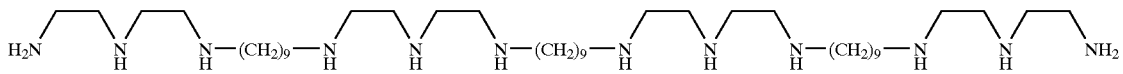

Data verifying the composition was collected using HNMR, and is provided as follows: $^1$HNMR($D_2O$): 1.65(m,30H), 1.75(m,12H), 3.2(t,12H), 3.5(m,32H).

Example 74

Preparation of 1,4,7,17,20,23,33,36,39,49,52,55-dodecaneazapentapentacontane Bonded to Silica Gel About 870 mg of 1,4,7,20,23,33,36,39,49,52,55-dodecaneazapentopentacontanee 12HBr was neutralized with 2N NaOH solution to pH 89. Then, 10 ml of buffer solution (pH 10) and 350 mg of glycidoxypropyl modified silica were added and stirred at 45° C. for 2 days. After cooling, the mixture was filtered and washed with $H_2O$ and MeOH to give silica gel with bounded amine. The preparation scheme is shown below:

(10:1), then (5:1) to give 1.43 g (33%) of the title compound as a pale yellow oil. The reaction is shown schematically as follows:

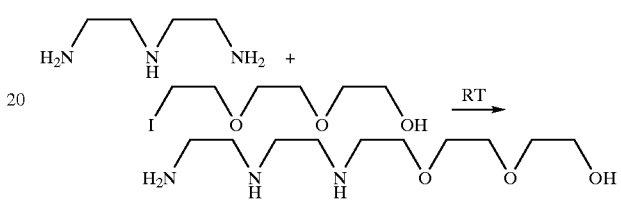

Data verifying the composition was collected using H NMR, and is provided as follows: $^{11}$HNMR ($CDCl_3$): 2.2(6s,2H), 2.8(m,100H), 3.7(m,10H).

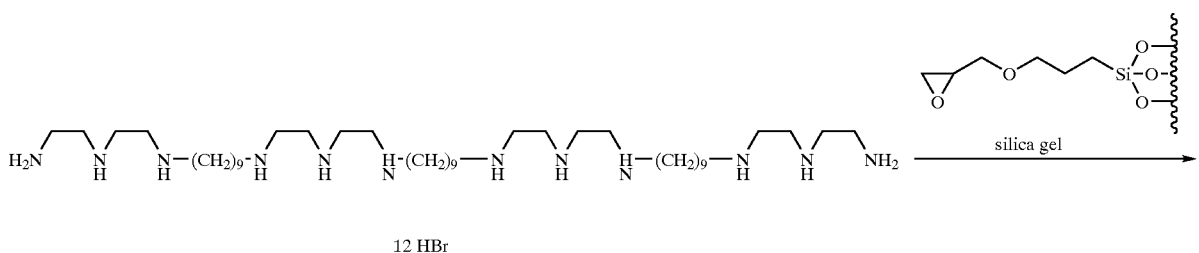

12 HBr

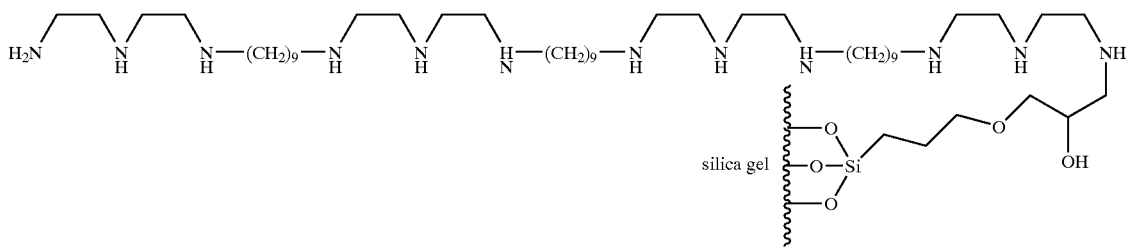

Example 75

Preparation of 9,12,15-triaza-3,6-dioxa-pentadecanol

A mixture of diethylene triamine (460 ml, 4.3 mole) and (2-iodoethoxy) ethoxyethanol (7.30 g, 28 mmole) was stirred-at room temperature for 1 hour. The excess of diethylenetriamine was removed by distillation under vacuum. The residue was then treated with aqueous Satd NaOH, extracted with $CH_2Cl_2$, dried over $MgSO4/Na_2CO_3$, filtered, and concentrated to give a yellow oil. This was purificated by column chromatography on silica with $CH_3OH/NH4OH$

Example 76

Preparation of 9,12,15-(tri-t-butoxycarbonyl)-9,12,15-triaza-3,6-dioxapentadecanol A solution of di-t-butyl-dicarbonate (4.75 g, 22 mmole) in 30 ml dioxane was added to a stirring mixture of the triamine produced from Example 75 (1.43 g, 6.1 mmole), NaOH (1.76, 44 mmole) in 60 ml $H_2O$ at 15° C. dropwise, and the reaction mixture was stirred overnight at room temperature. The reaction mixture was partitioned in $Et_2O/H_2O$. The ether layer was dried over $MgSO_4$, filtered, and concentrated to give 2.03 g (62% g) of crude material colorless oil. This product was used for the next step without further purification. The reaction is shown schematically as follows:

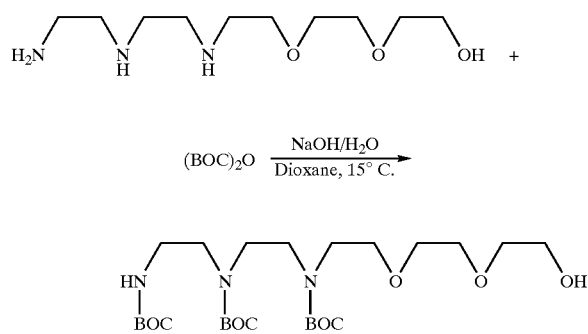

Data verifying the composition was collected using H NMR, and is provided as follows: $^1$HNMR (CDCl$_3$): 3.4(m,I OH), 3.6(m,10H).

Example 77

Preparation of 9,12,15-tri-t-butoxycarbonyl-9,12,15-triaza-3,6-dioxapentadecanol-p-toluenesulfonate A mixture of the nitrogen protected alcohol (2.0 g, 3.7 mmole), Et$_3$N (0.42 g, 4.2 mmole), DMAP(0.10 g, 0.82 mmole) and Tosyl Chloride (0.78 g, 4.1 mmole) in 80 ml of CH$_2$Cl$_2$ was allowed to stir overnight. The reaction mixture was then diluted with CH$_2$Cl$_2$ (200 ml) and washed with H$_2$O. The organic layer was dried over MgSO$_4$, filtered, and concentrated to give a pale yellow oil, crude material which was purified by column chromatography on silica with Hexanol/Ethyl Acetone (1:1), to give 2.13 g (84%) of the compound as a colorless oil. The reaction is shown schematically below.

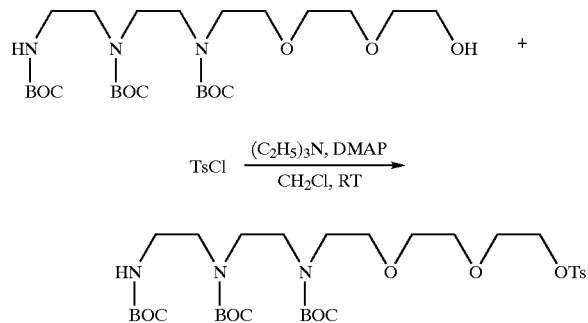

Data verifying the composition was collected using H NMR, and is provided as follows: $^1$HNMR (CDCl$_3$): 1.4(ms,27H), 2.4(6s,3H), 3.4–3.5(m,16H), 3.7(t,2H), 4.2(t,2H), 7.3(d,2H), 7.6(d,2H).

Example 78

Preparation of 10,13,16-triaza-1,4,7-trioxahexadecanyl-4(2,2',6'2"-terpyridyl) Phenyl Ether A mixture of N-Boc protected sulfonate (1.25 g, 1.8 mmole) hydroxy-phenylterpyridine (0.6 g, 1.8 mmole), and Cs$_2$CO$_3$ (0.90 g, 2.7 mmole) in DMF (50 ml), was heated to ~55° C. overnight. The reaction was cooled, and partitioned in CH2 Cl$_2$/H$_2$O and separated. The aqueous layer was extracted with CH$_2$Cl$_2$ (300 ml×2). The combined organic layers were dried over MgSO$_4$, filtered, and concentrated to give 1.0 g (66%) of crude material as a pale yellow oil which was used for the next step without purification. The deprotected reaction was as follows: the above/crude material (0.96 g, 0.75 mmole) was stirred in CF$_3$COOH(15 ml) at room temperature overnight. The volatiles were then removed under reduced pressure. The residue was then taken up in CH$_2$Cl$_2$ (200 ml), washed with Satd. Na$_2$CO$_3$ dried over MgSO$_4$, filtered, and concentrated to give the title compound (0.38 g, 94%) as a pale yellow oil. The scheme is shown schematically below:

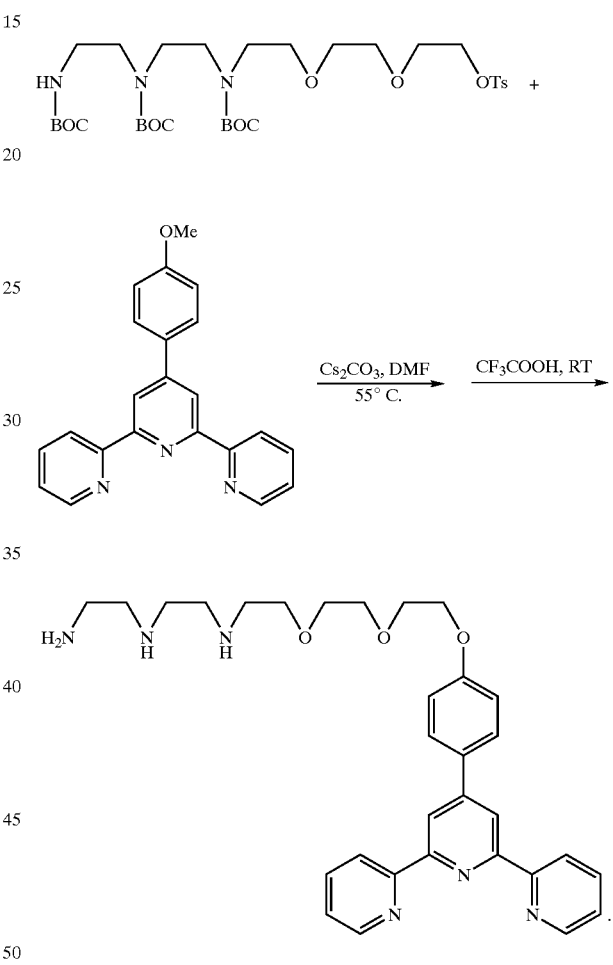

Data verifying the composition was collected using H NMR, and is provided as follows: $^1$HNMR (CDCl$_3$): 2.0(6s,4H), 2.8(m,10H), 3.6(m,6H), 3.9(t,2H), 4.2(t,2H), 7.3(m,2H), 7.8 (m,4H), 8.7(m,6H).

Example 79

Preparation of Silica Bound Triamine-Dioxa-Phenyl-Terpyridine

Triamine-dioxa-phenyl-terpyridine (0.30 g, 0.6 mmole) was heated with epoxy-activated silica gel (1.0 g) in 50 ml toluene at 80° C. for 20 hours. The product was collected by filtration, washed with toluene and CH$_3$OH, and dried in a vacuum oven at 55° C. for 20 hours. The reaction is shown schematically below.

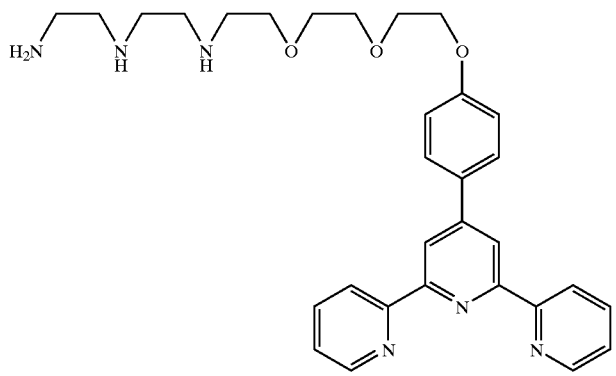
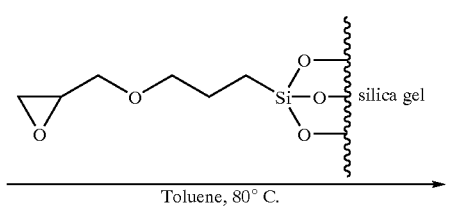

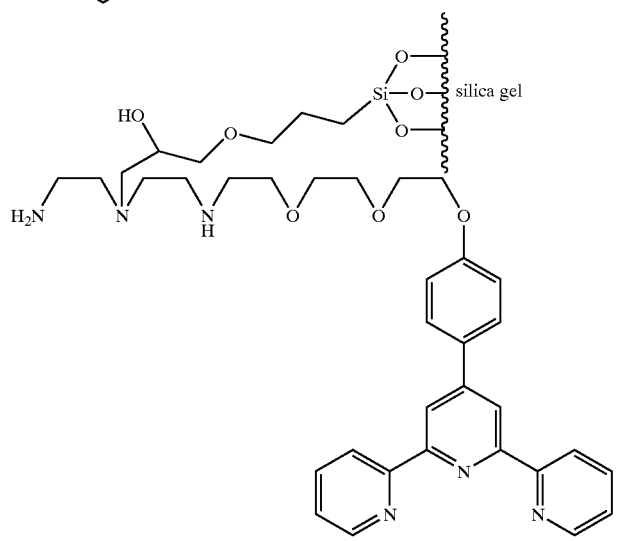

Example 80

Preparation of 7,10,13-triaza-1,4-dioxa-tridecanyl-4-(2,2'6',2"-terpyridyl) Phenyl Ether A mixture of diethylenetriamine (71.69 g, 0.69 mmole) and 0'-terpyridyl-phenyl-diethylglycol-tosylate (2.0 g, 3.5 mmole) was stirred at room temperature for 21 hours. The excess triamine was removed by distillation under reduced pressure. The residue was partitioned in CHCl$_3$/H$_2$O. The organic layer was dried, filtered and concentrated to leave the title compound as a yellow oil (2.05 g, quantitative). The reaction is shown schematically below:

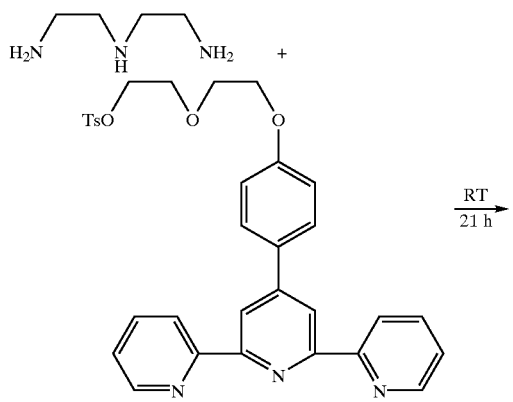

-continued

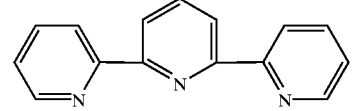

Data verifying the composition was collected using H NMR, and is provided as follows: $^1$HNMR (CDCl$_3$): 2.7(m,10H), 3.6(t,2H), 3.8(t,2H), 3.6(t,2H), 3.8(t,2H), 4.2(t,2H), 7.1(m, 2H), 7.3(m,2H), 7.8(m,6H), 8.7(m,6H).

Example 81

Preparation of Silica Bound Triamine-Trioxa-Phenyl-Terpyridine

A mixture of triamine-trioxa-phenyl-terpyridine (0.35 g, 0.65 mmole) and epoxy-activated silica gel (1.20 g) was heated to 80° C. in 60 ml of toluene for 20 hours. The product was collected by filtration, washed with toluene and methanol, and then dried in a vacuum oven for 15 hours. The reaction is shown according to the scheme below.

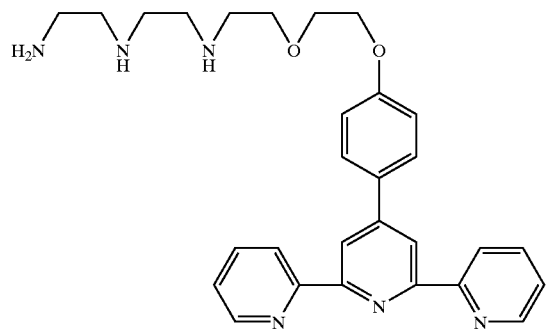
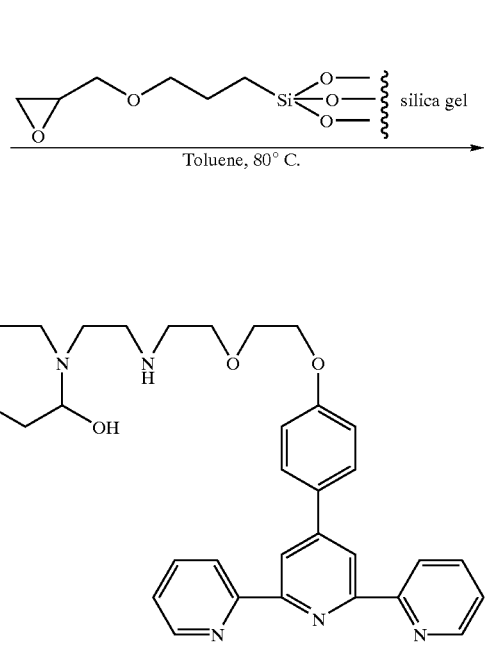

Example 82

Preparation of 7,10,13,22,25,28-hexaaza-1,4,16,19-tetraoxaoctacosanyl -4'''-(2,2'6'2''-terpyridyl) Phenylether A mixture of hexamine (4.09 g, 12.8 mmole), terpyridylphenyl-diethyglycol tosylate (1.81 g, 3.2 mmole) was refluxed in $CH_2Cl_2$ for 4 days. An oil thus formed was separated from $CH_2Cl_2$ by decanting. The oil was washed with $CH_2Cl_2$. The combined $CH_2Cl_2$ solution was concentrated to give a crude oil, which was passed through a short pad of silica gel, eluted with $CH_3OH$, and then $CH_3OH/NH_4OH$. Two major fractions were collected and checked. The last fraction (0.48 g) was taken up in $CH_2Cl_2$, and washed with $H_2O$ to remove trace amount of SuperLig® hexamine. After drying and concentration, 0.43 g (5%) of the title compound was obtained as a pale yellow oil. The reaction is shown schematically below.

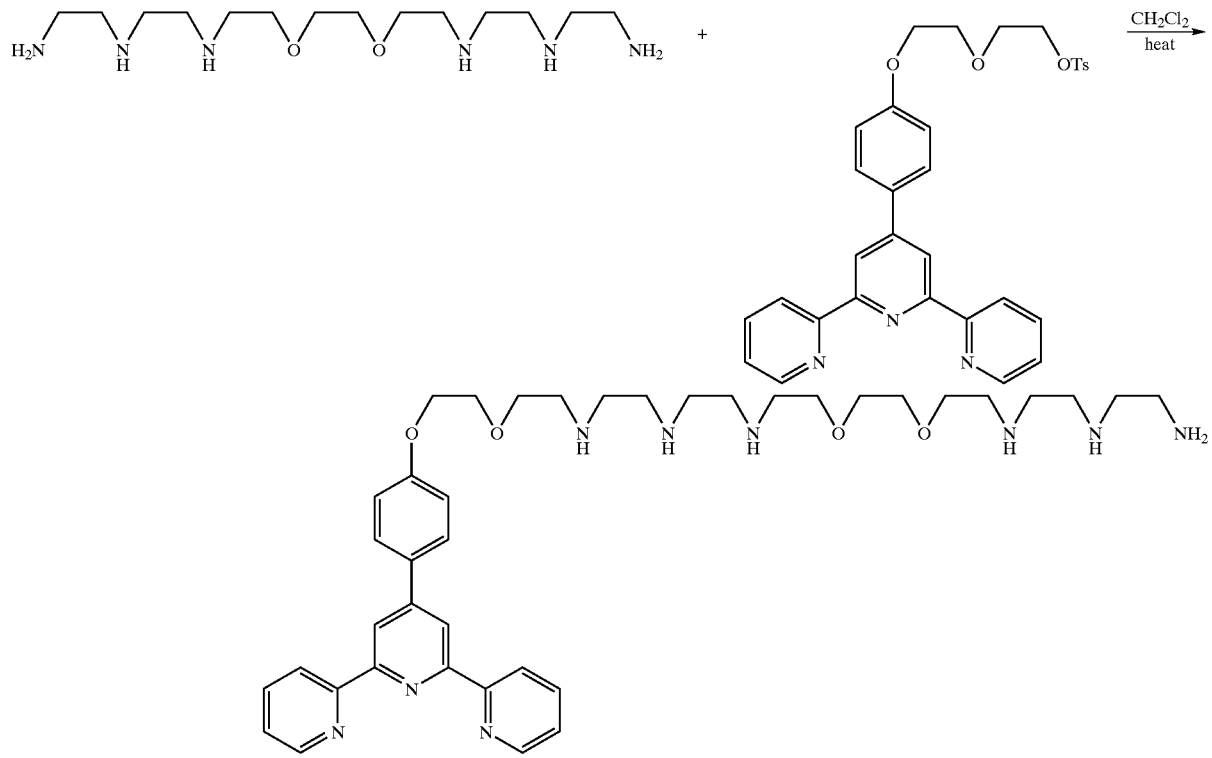

Data verifying the composition was collected using H NMR, and is provided as follows: ¹HNMR (CDCl₃): 1.6(6s,7H), 2.7(m,22H), 3.7(m,10H), 3.8(t,2H), 4.2(t,2H), 7.1(m,2H), 7.3(m,2H), 7.8(m,4H).

Example 83

Preparation of Silica Bound 7,10,13,22,25,26-hexane-1,4,16,19-tetraoxa octacosanyl-4"(2,2',6',2"-terpyridyl) Phenylether An amount of 7,10,13,22,25,26-hexane-1,4,16,19-tetraoxa octacosanyl-4"(2,2',6',2"-terpyridyl) phenylether (0.18 g, 0.25 mmole) was heated with epoxy activated silica gel (0.46 g) in 50 ml of toluene at 85° C. for 19 hours. The product was collected by filtrate, washed with toluene and methanol and then dried in the vacuum oven for 20 hours. The reaction is shown schematically below:

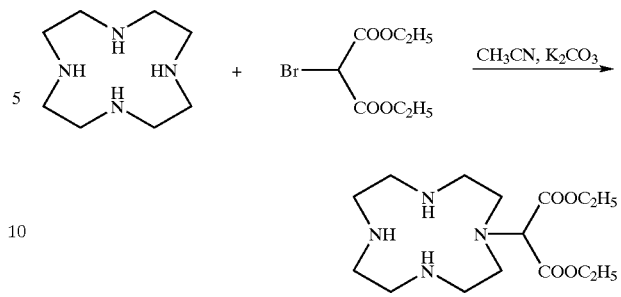

The 4-N-malonate-tetraaza-12-crown was identified by ¹H NMR spectroscopy as follows: ¹HNMR (CDCl₃): 4.9(bs.—OH—NH), 4.3(m), 3.0(m).

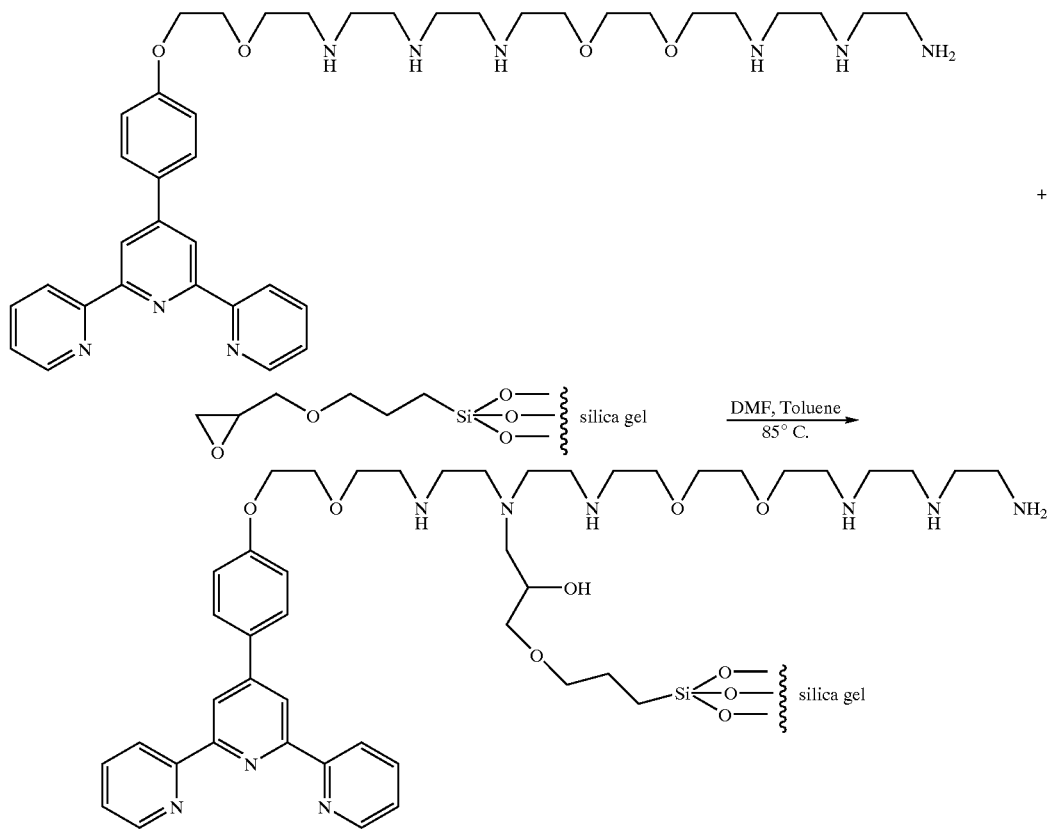

Example 84

Preparation of 4-N-malonate-tetraaza-12-crown

A mixture of cyclene (3.0 g, 17.4 mmole), bromomalonate (1.38 g, 5.8 mmole), and K₂CO₃ (4.80 g, 34.6 mmole) was heated to gentle reflux for 24 hours. The insoluble material was filtered off, and washed with CH₃CN. The compound filtrate was concentrated to leave an oil which was further purified by column chromatography on Al₂O₃ to give 2.10 g (40%) of the impure compound. The reaction is shown schematically below.

Example 85

Preparation of N-tetraaza-12-crown-4-N-malonate Dilithium-Salt

About 1 g of N-malonate tetraaza-12-crown (1.0 g, 3.0 mmole) was treated with LiOH (0.44 g, 1.8 mmole) in CH₃OH (60 ml) at room temperature for 20 hours. The reaction mixture was then concentrated by evaporation. To the residue, CHCl₃ was added while shaking. The insoluble matter was then filtered and washed with CHCl₃. The combined CHCl₃ solution was concentrated to give a yellow solid (0.91 g, 92% crude yield). The reaction is shown schematically below:

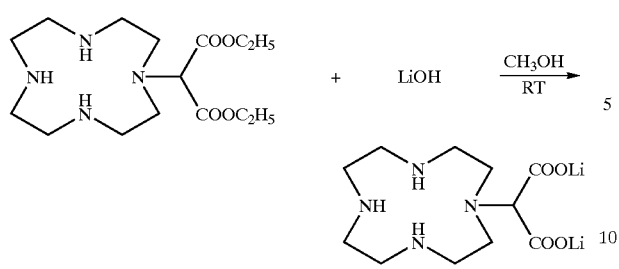

The N-tetraaza-12-crown-4-N-malonate dilithium-salt was identified by means of H NMR spectroscopy as follows: $^1$HNMR (CD$_3$OD): 4.9(bs, —OH,—NH), 4.5(m), 3.6(m), 2.6(m).

Example 86

Preparation of tetraaza-12-crown-4-N-malonate, Dilithium-Salt Bonded to Silica Gel The title compound was attached to silica gel according to the scheme shown below by employing the title compound (0.40 g, 1.4 mmole) and silica gel(0.40 g) in 50 ml of toluene at 80° C. for 21 hours. The product was filtered, washed with toluene and dried under vacuum at 55° C. for 20 hours. The reaction is shown schematically below:

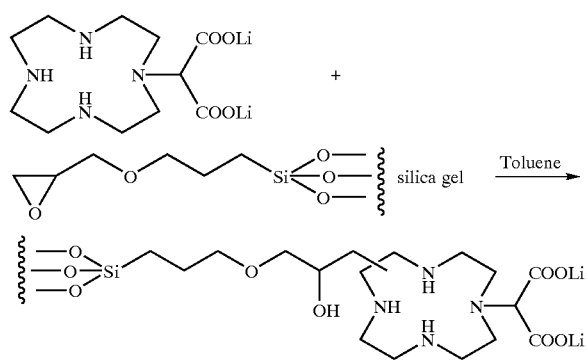

Example 87

Preparation of 9,12,15,25,28,31-hexa(p-toluenesulfonyl)-9,12,15,25,28,31-hexaaza-3,6-dioxaheneitriacontanol A mixture of 9-bis-(N,N'N"-tri-p-tolysulfonyl-diethylenetriamine)nonane (3.50 g, 2.8 mmole) and cesium carbonate (1.81 g, 5.60 mmole) in DMF (450 ml) was heated to 95° C. Then a solution of (2-chloroethoxy)ethoxy ethanol (0.479, 2.8 mmole) in DMF (100 ml) was added dropwise over 30 mins, and the temperature maintained at 95° C. overnight. The volatiles were evaporated off under reduced pressure and the residue was evaporated with toluene twice (250 ml×2). The final residue was partitioned in CH$_2$Cl$_2$/H$_2$O. The organic layer was collected, dried over MgSO$_4$, filtered, and concentrated to give a crude material which was further purified by column chromatography on silica with Hexane/Ethyl Acetate (10:1); (5:1); (2:1); (1:1); (1:2); to give the title compound (1.80 g. 46%). The reactionis shown schematically below:

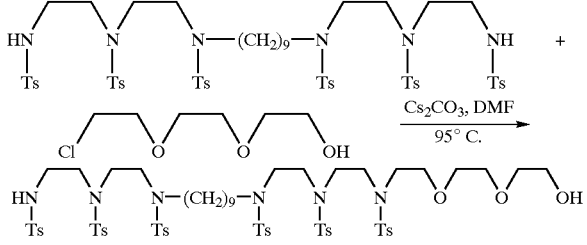

Data verifying the composition was collected using HNMR and is provided as follows: $^1$HNMR (CDCl$_3$): 7.75 (m,12H), 7.35(m,12H), 3.65(m,10H), 3.23(m,22H), 1.50 and 1.20 (2bs/14H)

Example 88

Preparation of 9,12,15,25,28,31-hexa(p-toluenesulfonyl)-9,12,15,25,28,31-hexaaza-3,6-dioxatritriacontanol To a stirring mixture of 9,12,15,25,28,31-hexa(p-toluenesulfonyl)-9,12,15,25,28,31-hexaaza-3,6-dioxahenetriacontanol (1.80 g, 1.3 mmole) and Cs$_2$CO$_3$ (0.70 g, 2.0 mmole) in DMF (50 ml), ethyliodide (0.30 g, 2.0 mmole) was added at room temperature. Then the temperature was raised to 65° to 70° C. for 4.5 hours. After being cooled, the reaction mixture was partitioned in CH$_2$Cl$_2$/H$_2$O. The organic layer was dried over MgSO$_4$, filtered, and concentrated to give a crude oil. This was further purified by column chromatography with silica and Hexane/Ethyl Acetate (1:1), then (1:2), to give 1.41 g (77%) of title compound. The reaction is shown schematically below:

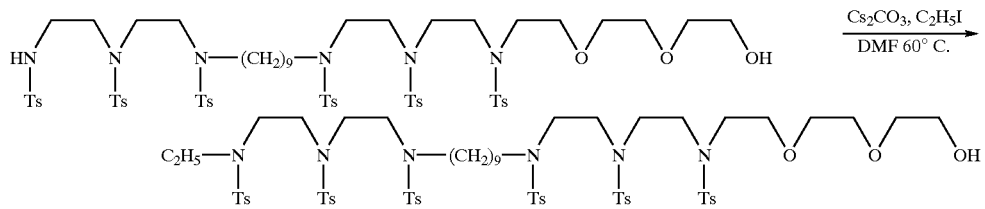

Data verifying the composition was collected using H NMR and is provided as follows: $^1$HNMR (CDCl$_3$): 7.7(m,12H), 7.35(m,12H), 3.6(m,10H), 3.3(m,24H), 2.4(s's, 18H), 1.5 and 1.3(2bs, 14H), 1.2(t,3H)

Example 89

Preparation of 9,12,15,25,28,31-hexaaza-3,6-dioxatritriacontanol

A mixture of 9,12,15,25,28,31-hexa(p-toluenesulfonyl)-9,12,15,25,28,31-hexaaza-3,6-dioxatritriacontanol (1.30 g, 0.92 mmole), Na/Hg (10.85 g), and phosphoric acid disodium salt (1.96 g, 13.8 mmole) in methanol/dioxane (70 ml/40 ml) was heated to gentle reflux for 24 hours. Additional Na/Hg (2.0 g) was then added. The reaction mixture was maintained at reflux for another 24 hours, then cooled. The insoluble material was filtered and washed with CH₃OH. The filtrate was concentrated to give an oily residue which was then treated with 2 N HCl (aq) and washed with CH₂Cl₂ (200 ml×2). The aqueous acidic solution was then made basic with 10% NaOH (aq), extracted with CH₂Cl₂ (250 ml×3), dried over MgSO₄, filtered and concentrated to give a pale yellow oil (0.25 g, 55% crude yield) which was used further without purification. The reaction is shown schematically below:

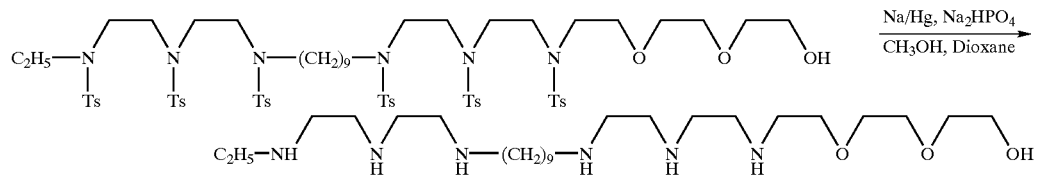

Data verifying the composition was collected using HNMR and is provided as follows: ¹HNMR (CDCl₃): 3.65(m,10H), 2.75(m,44H), 1.5 and 1.3(2bs, 14H), 1.15(t,3H)

Example 90
Preparation of 9,12,15,25,28,31-hexa(t-butoxycarbonyl)-9,12,15,25,28,31-hexaaza-3,6-dioxatritriacontanol A solution of di-t-butyl-dicarbonate (0.75 g, 3.4 mmole) in 1,4-dioxane (30 ml) was added to a mixture of 9,12,15, 25,28,31-hexaaza-3,6-dioxatriacontanol (0.24 g, 0.49 mmole), and sodium hydroxide (0.27 g, 0.68 mmole) in 30 ml of H₂O at 10–15° C. dropwise. After stirring for 2 hours, the reaction mixture was diluted with water, extracted with Et₂O (200 ml×2), dried over MgSO₄, filtered and concentrated by evaporation to give 0.36 (66%) of title compound as a colorless oil. The reaction is shown schematically below:

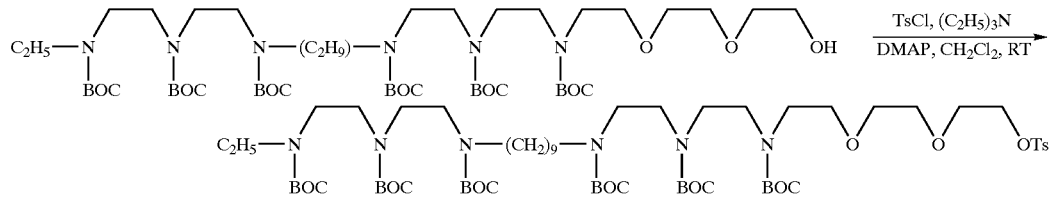

Data verifying the composition was collected using H NMR and is provided as follows: ¹HNMR (CDCl₃): 3.65(m,10H), 3.35(m,24H), 1.45(s,54H), 1.45 and 1.3(bs, 14H), 1.1(t,3H).

Example 91

Preparation of 9,12,15,25,28,31-hexa-(t-butoxycarbonyl)-9,12,15,25,28,31-hexaaza-3,6-dioxa-tritriacontanyl-p-tosyl-sulfonate A mixture of 9,12,15,25,28,31-hexaaza(t-butoxycarbonyl)-9,12,15,25,28,31-hexaaza-3,6-dioxatritriacontanol (0.35 g, 0.32 mmole), triethylamine (0.036 g, 0.36 mmole), 4-dimethylaminopyridine (0.05 g, 4.1 mmole), and tosyl chloride (0.07 g 0.35 mmole) was stirred at room temperature in CH₂Cl₂ (50 ml) for 20 hours, and then stirred at 50° C. for 30 minutes. The reaction mixture was diluted with CH₂Cl₂, washed with H₂O, dried over MgSO₄, filtered and concentrated to give an oil. The final title compound was obtained after purification by column chromotagraphy on silica gel with Ethyl Acetate/Hexanes (2:1), to give a colorless oil (0.22 g, 55%). The reaction is shown schematically below:

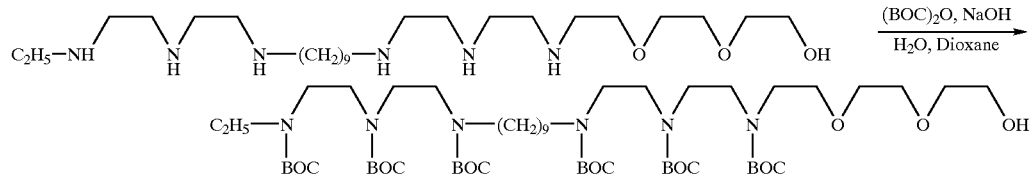

The title compound was characterized by H NMR (CDCl₃): 7.6(d,2H), 7.4(d,2H), 4.2(t,2H), 3.7(m,2H), 3.5(m,6H), 3.4 (m,24H), 2.4(S,3H), 1.4(S, 54H), 1.48 and 1.2(m,14H), 1.1(t,3H).

Example 92
Preparation of 10,13,16,26,29,32-hexaaza-1,4,7-trioxatetratriacontanyl-4'''-(2,2',6',2''-terpyridyl) Phenyl Ether A mixture of 9,12,15,25,28,31-hexa-(t-butoxycarbonyl)-9,12,15,25,28,31-hexaaza-3,6-dioxa tritriacontanyl-p-toluenesulfonate (0.21 g, 0.17 mmole), 4'(-4-hydroxyphenyl)-terpyridine(0.06 g, 0.19 mmole), and Cs₂CO₃ (0.06gmn 0.19 mmole) was heated to 80° C. in DMF (30 ml) overnight, The reaction mixture was partitioned in $CH_2Cl_2/H_2O$. The organic layer was dried over $MgSO_4$, filtered and concentrated to give an oily crude product which was then dissolved in 20 ml of $CF_3COOH$. The reaction mixture was stirred overnight. The volatiles were evaporated and the residue was taken up in $CH_2Cl_2$, washed with $Na_2CO_3$(aq), dried over $MgSO_4$, filtered and concentrated to give a 10,13,16,26,29,32-hexaaza-1,4,7-trioxatetratriacontanyl-4'''-(2,2',6',2''-terpyridyl) phenyl ether oil (0.07 g, 52%). The reaction is shown schematically as follows:

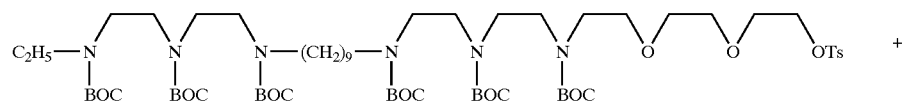

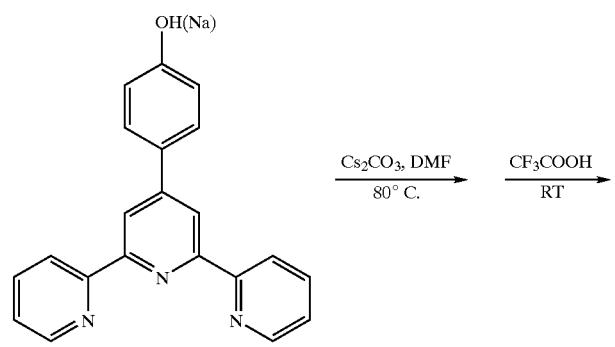

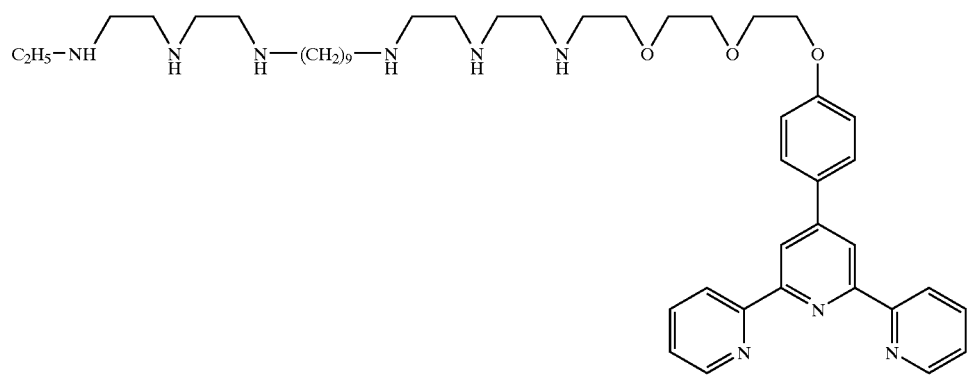

The title compound was characterized by H NMR spectroscopy in $CDCl_3$:8.7 (m,6H), 7.8(m,4H), 7.2(m,2H), 7.4(m, 2H), 4.2(t,2H), 3.8(t,2H), 3.6(m,6H), 2.6(m,24H), 1.4 and 1.2(m,14H), 1.1(t,3H).

Example 93

Preparation of 10,13,16,26,29,32-hexaaza-1,4,7-trioxatetratriacontanyl-4'''-(2,2',6',2''-terpyridyl) Phenyl Ether A mixture of triamine-nonane-triamine-para-trioxa-phenyl-terpyridine (0.07, 0.09 mmole) and epoxy-activated silica gel (0.20 g) was heated to 90° C. in 50 ml of toluene overnight. The product was collected by filtration, washed with toluene and $CH_3OH$, and dried in a vacuum oven for 15 hours. The reaction is shown schematically below:

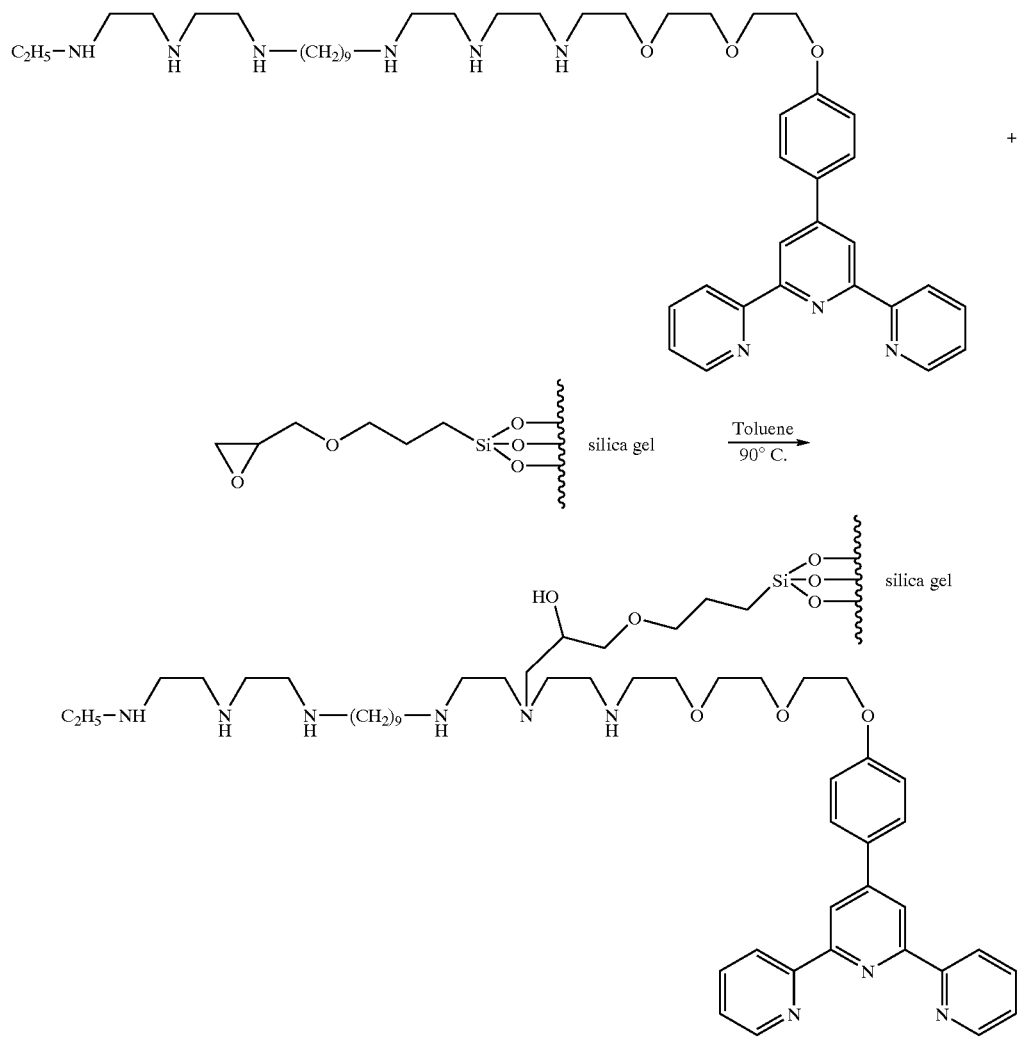

Separation and selectivity examples are now provided that utilize palladium(II)-bound ligands bonded to solid supports as described in Examples 1 to 93.

Example 94

Separation of Guanosine Monophosphate

A 0.0406 g (wet) amount of methylated ethylene triamine covalently bonded to silica material as described in Example 3 loaded with palladium was placed in a column. A 25° C. 4 ml source solution consisting of 1.25 mMolar each of adenosine monophosphate (hereinafter "AMP"), cytidine monophosphate (hereinafter "CMP"), thymidine monophosphate (hereinafter "TMP"), guanosine monophosphate (hereinafter "GMP"), and uridine monomonophosphate (hereinafter "UMP") in 0.01 Molar pH 7 phosphate buffer (Na salts) was drawn through the column at a flowrate of 0.02 ml/min. The column was then washed with 1 ml of 0.01 Molar phosphate pH 7 buffer at 0.05 ml/min flowrate followed by 2 ml of 2.5 Molar phosphate pH 5 buffer at a flowrate of 0.05 ml/min. The column was eluted or stripped using 1 ml of 0.5 Molar $NH_3$ at a flowrate of 0.01 ml/min. The collected 1 ml of elution contained guanine monophosphate at a purity of >99% compared to all of the other mononucleotides present as measured by HPLC (High Pressure Liquid Chromatography). The other mononucleotides could not be detected in the 0.161 mMolar guanine monophosphate collected.

Example 95

Separation of Guanosine Monophosphate

A 0.0421 g (wet) amount of a palladium loaded nonmethylated diethylene triamine covalently bonded to silica material of Example 1 was placed in a column. A 25° C. 1.9 ml source solution consisting of 1.25 mMolar each of AMP, CMP, TMP, GMP, and UMP in 0.01 Molar pH 7.3 phosphate buffer (Na salts) was drawn through the column at a flowrate of 0.02 ml/min. The column was then washed with 1 ml of 0.01 molar phosphate pH 7 buffer at 0.05 ml/min flowrate followed by 2 ml of pH 5 2.5 Molar phosphate buffer at a flowrate of 0.05 ml/min flowrate. Finally, the column was eluted or stripped using 1 ml of 1 Molar $NH_3$ at a flowrate of 0.015 ml/min. The collected 1 ml of elution contained guanosine monophosphate at a purity of >99% versus all of the other mononucleotides as measured by HPLC (High Pressure Liquid Chromatography). All of the other mononucleotides were below detection in the 0.755 mMolar guanosine monophosphate solution. Greater concentrations can be achieved by using a larger scale.

Example 96

Separation of Guanylyl (3'-5') Guanosine

A 0.0045 g (wet) amount of a bis-diethylene triamine covalently bonded to silica material as described in Example 10 loaded with palladium was placed in a column. A 25° C. 1.05 ml source solution consisting of 0.18 mMolar each of adenylyl (3'-5')adenosine (hereinafter "AA"), cytidylyl (3'-5') cytidine (hereinafter "CC"), thymidylyl (3'-5') thymidine (hereinafter "TT"), guanylyl (3'-5') guanosine (hereinafter "GG"), and uridylyl (3'-5') uridine (hereinafter "WU") in 0.01 Molar pH 7 phosphate buffer (Na salts) was drawn through the column at a flowrate of 0.05 ml/min. The column was then washed with 0.6 ml of 0.01 Molar phosphate buffer at 0.05 ml/min flowrate followed by 1.1 ml of pH 5 2.5 Molar phosphate buffer at a flowrate of 0.05 ml/min flowrate. The column was eluted or stripped using 0.6 ml of Molar NH3 at a flowrate of 0.05 Ml/min. The collected 0.6 ml of elution contained GG at a priority of >99% versus all of the other dinucleotides as measured by HPLC (High Pressure Liquid Chromatography). The other dinucleotides were not detected in the 0.058 mMolar guanyl (3'-5') guanosine eluent sample.

Example 97

Separation of Adenosine Monophosphate

A 0.1 ml amount of amino diphosphonic acid covalently bonded to silica material of Example 25 (and loaded with palladium) was placed in a column. A 25° C. 6 ml source solution consisting of 2 mMolar each of AMP, CMP, TMP, GMP, and UMP in 0.01 Molar pH 7.3 phosphate buffer (Na salts) was drawn through the column at a flowrate of 0.04 ml/min. The column was then washed with 1 ml of 0.01 Molar phosphate pH 7 buffer at 0.04 ml/min flowrate followed by 2 ml of pH 7 0.5 Molar phosphate buffer (Na salts) at a flowrate of 0.04 m/min. Finally the column was eluted or stripped using 1 ml of 0.1 Molar $NH_3$ at a flowrate of 0.04 Ml/min. The collected 1 ml of elution contained adenosine monophosphate at a purity of about 96% versus all of the other mononucleotides as measured by HPLC (High Pressure Liquid Chromatography). The adenosine monophosphate was collected at 0.497 mMolar in this small scale example.

Example 98

Separation of Thymidine Monophosphate

About 0.04 g (wet) of a palladium loaded phenyl terpyridine covalently bonded to silica material of Example 28 was placed in a column. A 25° C. 2.5 ml source solution consisting of 1.00 mMolar each of AMP, CMP, TMP, and GMP in 0.01 Molar pH 7.3 phosphate buffer (Na salts) was drawn through the column at a flowrate of 0.02 ml/min. The column was then washed with 0.55 ml of 0.01 Molar phosphate pH 7 buffer at 0.02 ml/min flowrate followed by 2 ml of pH 4 2.5 Molar phosphate buffer at a flowrate of 0.02 ml/min flowrate to strip the TMP. The collected 2 ml of elution contained TMP at a purity of >90% versus all of the other mononucleotides as measured by HPLC (High Pressure Liquid Chromatography). Greater concentrations can be achieved by using a larger scale.

Example 99

Selectivity for TTT over TT and T

A 0.0106 g (wet) amount of a tertiary phenyl terpyridine covalently bonded to silica material of Example 35 (loaded with palladium) was soaked in 1.5 ml of a solution for 24 hours. The solution contained 0.1 mM each of TMP, TT, and thymidylyl (3'-5') thymidylyl (3'-5') thymidine (hereinafter "TTT") in 0.01 molar pH 7 phosphate buffer (Na salts). The starting and ending concentration of each of the nucleotides was measured using HPLC (High Pressure Liquid Chromatography). The results showed the TTT was reduced to 0.0106 mMolar, the TT was reduced to 0.0408 mMolar, and the TMP was reduced to 0.072 mMolar. Selectivity amongst the three nucleotides is calculated from the equilibrium data by comparing or calculating the ratio of the mMolarity removed divided by the final equilibrium concentration (in mMolar) for each nucleotide. This formula is shown below:

$$\text{Selectivity} = \frac{[\text{Starting conc. nucleotide } X - \text{Final conc. nucleotide } X]}{\text{Final conc. nucleotide } X} \Big/ \frac{[\text{Starting conc. nucleotide } Y - \text{Final conc. nucleotide } Y]}{\text{Final conc. nucleotide } Y}.$$

Hence, the selectivity of TTT over T (TMP) is 22 and the selectivity of TTT over TT is 12. This high selectivity shows the ability to selectively bind the TTT for use in making separations or analytical detection.

Example 100

Selectivity of TTT over AAA and CCC

A 0.0119 g (wet) amount of palladium loaded tertiary phenylterpyridine covalently bonded to silica material of Example 35 was soaked in 1.5 ml of a solution for 24 hours. The solution contained 0.086 mM each of adenylyl (3'-5') adenylyl (3'-5') adenosine (hereinafter "AAA"), cytidylyl (3'-5') cytidylyl (3'-5') cythdine (hereinafter "CCC"), and TTT in 0.01 molar pH 7 phosphate buffer (Na salts). The starting and ending concentration of each of the nucleotides was measured using HPLC (High Pressure Liquid Chromatography). The results showed the TTT was reduced to 0.033 mMolar, the CCC was reduced to 0.0675 mMolar, and the AAA was reduced to 0.0734 mMolar. Selectivity amongst the three nucleotides is calculated from the equilibrium data by comparing or calculating the ratio of the mMolarity removed divided by the final equilibrium concentration (in mMolar) for each nucleotide. This formula is shown below:

$$\text{Selectivity} = \frac{[\text{Starting conc. nucleotide } X - \text{Final conc. nucleotide } X]}{\text{Final conc. nucleotide } X} \Big/ \frac{[\text{Starting conc. nucleotide } Y - \text{Final conc. nucleotide } Y]}{\text{Final conc. nucleotide } Y}$$

Using this formula, the selectivity of TTT over CCC was determined to be 6.0 and the selectivity of TTT over AAA was determined to be 9.4. This high selectivity shows the ability to selectively bind the TTT for use in making separations or analytical detection.

Example 101

Separation of GG over AA, CC, TT, and UU

In this example, a 0.31 ml (wet) column of a palladium loaded Bis propyldithia covalently bonded to silica material of Example 18 was prepared. A 25° C. 1.75 ml source solution consisting of 0.2 mMolar each of AA, CC, GG, TT, and UU in 0.01 Molar pH 7.3 phosphate buffer (Na salts) was drawn through the column at a flowrate of 0.015 ml/min. The column was then washed with 0.45 ml of 0.01 Molar phosphate pH 7 buffer at 0.015 ml/min flowrate followed by 1.75 ml of pH 5 2.5 Molar phosphate buffer at a flowrate of 0.015 ml/min flowrate. Finally, the column was eluted or stripped using 1 ml of 1 Molar NH3 at a flowrate of 0.015 ml/min. The collected 1 ml of elution contained GG at a purity of >99% versus all of the other nucleotides as measured by HPLC (High Pressure Liquid Chromatography). All of the other nucleotides were below detection in the 19 mMolar guanosine monophosphate solution. Greater concentrations can be achieved by using a larger scale.

Example 102

Separation of GG over AA, CC, TT, and UU

A 0.02 g (wet) amount of a palladium loaded Bis 1,10-dithia-18-crown-6 covalently bonded to silica material of Example 23 was placed in a column. A 25° C. 5 ml source solution consisting of 50 mMolar each of AA, CC, GG, TT, and UU in 0.01 Molar pH 7.3 phosphate buffer (Na salts) was drawn through a column at a flowrate of 0.01 ml/min. The column was then washed with 1 ml of 0.01 molar phosphate pH 7 buffer at 0.01 ml/min flowrate. Finally, the column was eluted or stripped using 1 ml of 0.4 Molar $NH_3$ at a flowrate of 0.01 ml/min. The collected 1 ml of elution contained GG at a purity of >99% versus all of the other mononucleotides as measured by HPLC (High Pressure Liquid Chromatography). All of the other mononucleotides were below detection in the 0.239 mMolar guanosine monophosphate solution. Greater concentrations can be achieved by using a larger scale.

Example 103

Separation of TT over AA, CC, and GG

A 0.13 ml (wet) amount of a palladium loaded Bis phenyl terpyridine covalently bonded to silica material of Example 31 was placed in a column. A 250 C 2 ml source solution consisting of 0.25 mMolar each of AA, CC, GG, and TT was drawn through the column at a flowrate of 0.012 ml/min. The column was then washed with 0.45 ml of 0.01 molar phosphate pH 7 buffer at 0.012 ml/min flowrate followed by 0.95 ml of 0.1 M NH3 wash at a flowrate of 0.012 ml/min. Finally, the column was eluted or stripped using 0.95 ml of pH 4 0.5 M Phosphate Buffer at a flowrate of 0.012 ml/min. The collected 0.95 ml of elution contained TT at a purity of >99% versus all of the other mononucleotides as measured by HPLC (High Pressure Liquid Chromatography). All of the other mononucleotides were below detection in the 61 mMolar TT solution. Greater concentrations can be achieved by using a larger scale.

Example 104

Separation of TTT over GGG and AAA

A 0.411 g (wet) amount of a palladium loaded Tri Phenyl Terpyridine covalently bonded to silica material of Example 35 was placed in a column. A 25° C. 2 ml source solution consisting of 0.1 mMolar each of AAA, GGG (Guanyl (3'-5') guanyl (3'-5') guanidine) hereafter referred to as GGG, and TTT in 0.01 Molar pH 7.3 phosphate buffer (Na salts) was drawn through the column at a flowrate of 0.013 ml/min. The column was then washed with 0.55 ml of 0.01 molar phosphate pH 7 buffer at 0.013 ml/min flowrate followed by 1.05 ml of 0.1 Molar NH3 at a flowrate of 0.013 ml/min. Finally, the column was eluted or stripped using 2.18 ml of 0.5 Molar pH 4 Phosphate Buffer at 0.013 ml/min. The collected 2.18 ml of elution contained TTT at a purity of >99% versus all of the other mononucleotides as measured by HPLC (High Pressure Liquid Chromatography). All of the other mononucleotides were below detection in the 6 mMolar TTT solution. Greater concentrations can be achieved by using a larger scale.

Example 105

Selectivity of GMP over AMP, CMP, and TMP

The propyl dithia on silica material of Example 13 (preloaded with palladium) was soaked in a solution for 24 hours containing AMP, GMP, CMP, and TMP in 0.01 Molar pH 7 phosphate buffer (Na salts). The starting and ending concentration of each of the nucleotides was measured using HPLC and the selectivities calculated as done for Example 99 and 100. A selectivity of 6.3 for GMP over AMP, 12.6 for GMP over CMP, and 32 for GMP over TMP was measured. These selectivities show the ability to selectively bind the GMP for use in making separations or analytical detection.

Example 106

Selectivity of GG over GT

The Bis triamine bonded to silica material of Example 10 (preloaded with palladium) was soaked in a solution for 24 hours containing equal concentrations of GG and Guanyl (3'-5') Thymidine (hereafter referred to as GT) in 0.01 Molar pH 7 phosphate buffer (Na salts). The starting and ending concentration of each of the nucleotides was measured using HPLC and the selectivities calculated as done for Examples 99 and 100. A selectivity of 2.0 was measured. This selectivity shows the ability to selectively bind the GG for use in making separations or analytical detection even when the very similar GT is present.

Example 107

Selectivity for GG over AA, CC, TT, and UU

The Bis dithia-18-crown-6 on silica material of Example 23 (preloaded with palladium) was soaked in a solution for 24 hours containing equal concentrations of GG, AA, CC, TT, and UU in 0.01 Molar pH 7 phosphate buffer (Na Salts). The starting and ending concentration of each of the nucleotides was measured using HPLC and the selectivities calculated as done for Examples 99 and 100. A selectivity of 5 for GG over AA, 6 for GG over CC, 5 over GG over TT, and 4 for GG over UU was measured. These selectivities show the ability to selectively bind the GG for use in making separations or analytical detection.

Example 108

Selectivity for GG over AA, CC, and TT

The Bis dipropylene trithia on silica material of Example 50 (preloaded with palladium) was soaked in a solution for 24 hours containing equal concentrations of GG, AA, CC, and TT, in 0.01 Molar pH 7 phosphate buffer (Na Salts). The starting and ending concentration of each of the nucleotides was measured using HPLC and the selectivities calculated as done for Examples 99 and 100. A selectivity of 7 for GG over AA, 9 for GG over CC, and 2.3 for GG over TT was measured. These selectivities show the ability to selectively bind the GG for use in making separations or analytical detection.

Example 109

Selectivity of AA over GG, TT and UU

The Bis amino diphosphonic acid on silica material of Example 27 (preloaded with palladium) was soaked in a solution for 24 hours containing equal concentrations of AA, GG, TT and UU in 0.01 Molar pH 7 phosphate buffer (Na Salts). The starting and ending concentration of each of the nucleotides was measured using HPLC and the selectivities calculated as done for Examples 99 and 100. A selectivity of 16 for AA over CC, 8 for AA over GG, and >100 for AA over TT or UU was measured. These selectivities show the ability to selectively bind the AA for use in making separations or analytical detection.

Example 110

Selectivity of TT over GG, and GT

The Bis phenyl terpyridine on silica material of Example 31 (preloaded with palladium) was soaked in a solution for 24 hours containing equal concentrations of TT, GG, and GT in 0.01 Molar pH 7 phosphate buffer (Na Salts). The starting and ending concentration of each of the nucleotides was measured using HPLC and the selectivities calculated as done for Examples 99 and 100. A selectivity of 4.4 for TT over GG and 2.4 for TT over GT was measured. These selectivities show the ability to selectively bind the TT for use in making separation or analytical detection even when the very similar GT is present.

Example 111

Selectivity of GGG over AAA, CCC, and TTT

The Tri triamine on silica material of Example 67 (preloaded with palladium) was soaked in a solution for 24 hours containing equal concentrations of GGG, AAA, CCC, and TTT in 0.01 Molar pH 7 phosphate buffer (Na Salts). The starting and ending concentration of each of the nucleotides was measured using HPLC and the selectivities calculated as done for Examples 99 and 100. A selectivity of 103 for GGG over AAA, 8 for GGG over CCC, and 3 for GGG over TTT was measured. These selectivities show the ability to selectively bind the GGG for use in making separations or analytical detection.

Example 112

Selectivity of GGG over AAA, CCC, and TTT

The Tri propylene dithia on silica material of Example 47 (preloaded with palladium) was soaked in a solution for 24 hours containing equal concentrations of GGG, AAA, CCC, and TTT in 0.01 Molar pH 7 phosphate buffer (Na Salts). The starting and ending concentration of each of the nucleotides was measured using HPLC and the selectivities calculated as done for Examples 99 and 100. A selectivity of 33 for GGG over TTT, 13 for GGG over AAA, and 8 for GGG over CCC was measured. These selectivities show the ability to selectively bind the GGG for use in making separations or analytical detection.

Example 113

Selectivity of GGGG over TGGT, TTTT, GGTT, TTGT, and TTTG

The Tetra triamine on silica material of Example 74 (preloaded with palladium) was soaked in a solution for 24 hours containing equal concentrations of Guanyl(3'-5')-Guanyl(3'-5')-Guanyl(3'-5')-Guanidine (hereinafter "GGGG"), Thymidyl(3'-5')-Guanyl(3'-5')-Guanyl(3'-5')-Thymidine (hereinafter "TGGT"), Thymidyl(3'-5')-Thymidyl(3'-5')-Thymidyl(3'-5')-Thymidine (hereinafter "TTTT"), Guanyl(3'-5')-Guanyl(3'-5')-Thymidyl.(3'-5')-Thymidine (hereinafter "GGTT"), Thymidyl(3'-5')-Thymidyl(3'-5')-Guanyl(3'-5')-Thymidine (hereinafter "TTGT"), and Thymidyl(3'-5')-Thymidyl(3'-5')-Thymidyl(3'-5')-Guanine (hereinafter "TTTG") in 0.01 Molar pH 7 phosphate buffer (Na Salts). The starting and ending concentration of each of the nucleotides was measured using HPLC and the selectivities calculated as done for Examples 99 and 100. A selectivity of 1.8 for GGGG over GGGT, 2 for GGGG over TGGT, 2.2 for GGGG over TTTT, 1.9 for GGGG over GGTT, 2.3 for GGGG over TTGT, and 2.7 for GGGG over TTTG was measured. These selectivities show the ability to selectively bind the GGGG for use in making separations or analytical detection even in the presence of very similar nucleotides.

Example 114

Selectivity of TTTT over GGGG, CCCC, and AAAA

The Tetra phenyl terpyridine on silica material of Example 39 (preloaded with palladium) was soaked in a solution for 24 hours containing equal concentration of GGGG, TTTT, CCCC, and AAAA in 0.01 Molar pH 7 phosphate buffer (Na Salts). The starting and ending concentration of each of the nucleotides was measured using HPLC and the selectivities calculated as done for Examples 99 and 100. A selectivity of 55 for TTTT over GGGG, 5 for TTTT over CCCC, and >100 for TTTT over AAAA was measured. These selectivities show the ability to selectively bind the TTTT for use in making separations or analytical detection.

Example 115

Selectivity of GT over TT, GG, CC, and AA

The Triamine-phenyl terpyridine on silica with Trioxa Bridge material of Example 79 (preloaded with palladium) was soaked in a solution for 24 hours containing GT, TT, GG, CC, and AA in 0.01 Molar pH 7 phosphate buffer (Na Salts). The starting and ending concentration of each of the nucleotides was measured using HPLC and the selectivities calculated as done for Examples 99 and 100. A selectivity of 1.2 was measured for GT over TT, 1.4 for GT over GG, 4 for GT over CC, and 6 for GT over AA was measured. These selectivities show the ability to selectively bind the GT for use in making separations or analytical detection with similar or completely different nucleotides present.

Example 116

Selectivity of GTG over GTG, TTT, GGG, TGT, CCC, and AAA

The Triamine-phenyl terpyridine-triamine on silica material with meta-oxa-hexane bridges of Example 64 (preloaded with palladium) was soaked in a solution for 24 hours containing GTG, TTT, GGG, TGT, CCC, and AAA in 0.01 Molar pH 7 phosphate buffer (Na Salts). The starting and ending concentration of each of the nucleotides was measured using HPLC and the selectivities calculated as done for Examples 99 and 100. A selectivity of 3 for GTG over TTT, 1.5 for GTG over GGG, 3 for GTG over TGT, 8 for GTG over CCC, and 22 for GTG over AAA was measured. These selectivities show the ability to selectively bind the GTG for use in making separations or analytical detection with similar or very different nucleotides present.

Example 117

Selectivity of GGT over GTG, TGT, TTT, GGG, AGA, and CCC

The Triamine-triamine-phenyl terpyridine on silica material with a nonane and diethylene trioxa bridge of Example 93 (preloaded with palladium) was soaked in a solution for 24 hours containing GGT, GTG, TGT, TTT, GGG, AGA, and CCC in 0.01 Molar pH 7 phosphate buffer (Na Salts). The starting and ending concentration of each of the nucleotides was measured using HPLC and the selectivities calculated as done for Examples 99 and 100. A selectivity of 1.2 for GGT over GTG, 1.3 for GGT over TGT, 3.6 for GGT over TTT, 1.8 for GGT over GGG, 5.1 for GGT over AGA, and 5.4 for GGT over CCC was measured. These selectivities show the ability to selectively bind the GGT for use in making separations or analytical detection with similar or very different nucleotides present.

Example 118

Selectivity of GGT over TGT, TTT, GGG, CCC, and AAA

The Trimine-triamine-phenyl terpyridine on silica material with ethylene dioxa bridges of Example 83 (preloaded with palladium) was soaked in a solution for 24 hours containing GGT, TGT, TTT, GGG, CCC, and AAA in 0.01 Molar pH 7 phosphate buffer (Na Salts). The starting and ending concentration of each of the nucleotides was measured using HPLC and the selectivities calculated as done for Examples 99 and 100. A selectivity of 1.3 for GGT over TGT, 1.3 for GGT over TTT, 1.3 for GGT over GGG, 3.2 for GGT over CCC, and 8.9 for GGT over AAA was measured. These selectivities show the ability to selectively bind the GGT for use in making separations or analytical detection with similar or very different nucleotides present.

Example 119 selectivity of CMP over AMP, GMP, and TMP

In this example, the tetra-aza-12-Crown-4 malonate on silica material of Example 86 (preloaded with palladium) was soaked in a solution for 24 hours containing AMP, GMP, CMP, and TMP in 0.01 Molar pH 7 phosphate buffer (Na Salts). The starting and ending concentration of each of the nucleotides was measured using HPLC and the selectivities calculated as done for Examples 99 and 100. A selectivity of 1.6 for CMP over AMP, 1 for CMP over GMP, and 5 for CMP over TMP was measured. These selectivities show the ability to selectively bind the CMP for use in making separations or analytical detection, particularly over AMP and TMP.

While the invention has been described with reference to certain preferred embodiments, those skilled in the art will appreciate that various modifications, changes, omissions, and substitutions can be made without departing from the spirit of the invention. It is therefore intended that the invention be limited only by the scope of the appended claims.

We claim:

1. A composition for selectively binding a desired nucleotide sequence, said composition comprising from 2 to 4 palladium(II)-bound ligands, said palladium(II)-bound ligands being tethered together by an organic backbone having from 3 to 20 atoms between each palladium(II)-bound ligand, thereby forming a palladium(II)-bound ligand backbone grouping, said palladium(II)-bound ligand backbone grouping being covalently bonded to a solid support, and wherein each palladium(II)-bound ligand is independently selective of a desired heterocyclic aromatic amine base of the nucleotide sequence to be selectively bound.

2. A composition as in claim 1, comprising 2 palladium (II)-bound ligands.

3. A composition as in claim 1, comprising 3 palladium (II)-bound ligands.

4. A composition as in claim 1, comprising 4 palladium (II)-bound ligands.

5. A composition as in claim 1 being configured to select a nucleotide sequence having predetermined adjacent heterocyclic aromatic amine bases.

6. A composition as in claim 1, wherein each palladium (II)-bound ligand is independently selective of the same heterocyclic aromatic amine base of the nucleotide sequence.

7. A composition as in claim 1, wherein each palladium (II)-bound ligand is independently selective of different heterocyclic aromatic amine base of the nucleotide sequence.

8. A composition as in claim 1, wherein at least one ligand of the 2 to 4 palladium(II)-bound ligands comprises the sequence:

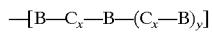

wherein C is carbon, each B is independently nitrogen, sulfur, or phosphene; x is 2 or 3; and y is 0, 1 or 2.

9. A composition as in claim 1 wherein at least one ligand of the 2 to 4 palladium(II)-bound ligands comprises the sequence:

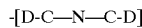

wherein C is carbon, N is nitrogen, and D is selected from the group consisting of carboxyl moieties, phosphonic moieties, and sulfonic moieties.

10. A composition as in claim 9, wherein at least one ligand of the 2 to 4 palladium(II)-bound ligands is selected from the group consisting of dipicolinic acid and aminodiphosphate.

11. A composition as in claim 1, wherein at least one ligand of the 2 to 4 palladium(II)-bound ligands comprises the sequence:

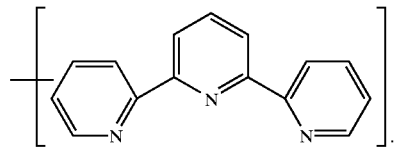

12. A composition as in claim 11, wherein the at least one ligand is:

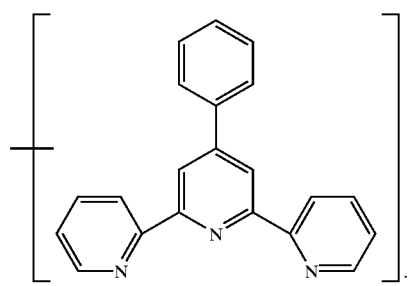

13. A composition as in claim 1, wherein at least one ligand of the 2 to 4 palladium(II)-bound ligands comprises the sequence:

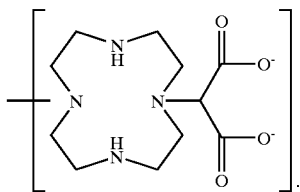

14. A composition as in claim 1, wherein at least one ligand of the 2 to 4 palladium(II)-bound ligands is selective of adenine (A).

15. A composition as in claim 1, wherein at least one ligand of the 2 to 4 palladium(II)-bound ligands is selective of guanine (G).

16. A composition as in claim 1, wherein at least one ligand of the 2 to 4 palladium(II)-bound ligands is selective of thymine (T).

17. A composition as in claim 1, wherein at least one ligand of the 2 to 4 palladium(II)-bound ligands is selective of uracil (U).

18. A composition as in claim 1, wherein at least one ligand of the 2 to 4 palladium(II)-bound ligands is selective of cytosine (C).

19. A composition as in claim 1, wherein said composition is configured for use in selectively binding DNA sequences.

20. A composition as in claim 1, wherein said composition is configured for use in selectively binding RNA sequences.

21. A composition as in claim 1, wherein the solid support is an inorganic solid support and the palladium(II)-bound ligand backbone grouping is bonded to the solid support through a silane covalent linkage mechanism and an organic spacer grouping having from 1 to 10 atoms.

22. A composition as in claim 1, wherein the solid support is an organic solid support and the palladium(II)-bound ligand backbone grouping is bonded to the solid support through an organic covalent linkage mechanism having from 1 to 10 atoms.

23. A composition, comprising a palladium(II)-bound ligand covalently bonded to a solid support, said palladium (II)-bound ligand being complexed to a heterocyclic aromatic amine base.

24. A composition as in claim 23, wherein the heterocyclic aromatic amine base is in the form of a nucleoside.

25. A composition as in claim 23, wherein the heterocyclic aromatic amine base is in the form of a nucleotide.

26. A composition as in claim 23, wherein the heterocyclic aromatic amine base comprises adenine (A).

27. A composition according to claim 26 wherein the ligand of the palladium(II)-bound ligand comprises the sequence:

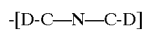

-[D-C—N—C-D]

wherein C is carbon, N is nitrogen, and D is selected from the group consisting of carboxyl moieties, phosphonic moieties, and sulfonic moieties.

28. A composition according to claim 27, the ligand is selected from the group consisting of dipicolinic acid and aminodiphosphate.

29. A composition as in claim 23, wherein the heterocyclic aromatic amine base comprises thymine (T).

30. A composition according to claim 29, wherein the ligand of the palladium(II)-bound ligand comprises the sequence:

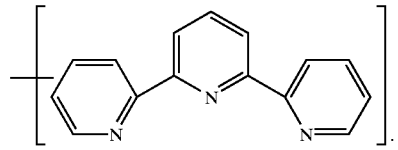

31. A composition according to claim 30, wherein the ligand is:

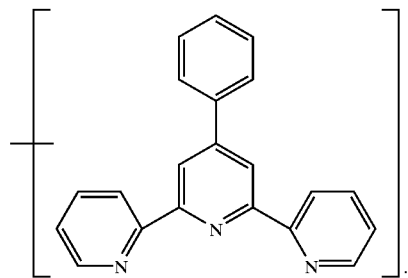

32. A composition as in claim 23, wherein the heterocyclic aromatic amine base comprises uracil (U).

33. A composition according to claim 32, wherein the ligand of the palladium(II)-bound ligand comprises the sequence:

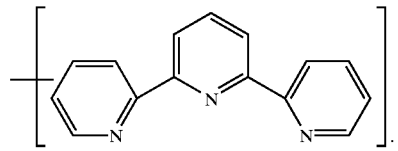

34. A composition according to claim 33, wherein the ligand is:

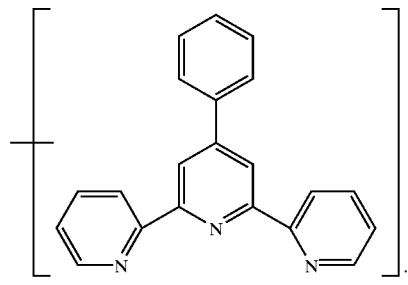

35. A composition as in claim 23, wherein the heterocyclic aromatic amine base comprises guanine (G).

36. A composition according to claim 35, wherein the ligand of the palladium(II)-bound ligand comprises the sequence:

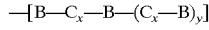

—[B—$C_x$—B—$(C_x$—B$)_y$]

wherein C is carbon, each B is independently nitrogen, sulfur, or phosphene; x is 2 or 3; and y is 0, 1 or 2.

37. A composition according to claim 36, wherein x is 2 and y is 1.

38. A composition according to claim 37, wherein B is nitrogen.

39. A composition as in claim 23, wherein the heterocyclic aromatic amine base comprises cytosine (C).

40. A composition according to claim 39, wherein the ligand of the palladium(II)-bound ligand comprises the sequence:

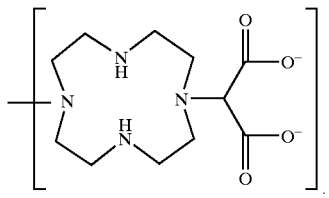

41. A composition as in claim 23, wherein the solid support is an inorganic solid support and the palladium(II)-bound ligand backbone grouping is bonded to the solid support through a silane covalent linkage mechanism and an organic spacer grouping.

42. A composition as in claim 23, wherein the solid support is an organic solid support and the palladium(II)-bound ligand backbone grouping is bonded to the solid support through an organic covalent linkage mechanism having from 1 to 10 atoms.

43. A composition, comprising a palladium(II)-bound ligand covalently bonded to a solid support through a spacer, said ligand portion of the palladium(II)-bound ligand comprising the sequence:

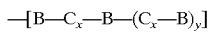

wherein C is carbon, each B is independently nitrogen, sulfur, or phosphene; x is 2 or 3; and y is 0, 1 or 2, and wherein the palladium(II)-bound ligand is complexed with guanine.

44. A composition, comprising a palladium(II)-bound ligand covalently bonded to a solid support through a spacer, said ligand portion of the palladium(II)-bound ligand comprising the sequence:

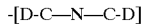

wherein C is carbon, N is nitrogen, and D is a negative binder, and wherein the palladium(II)-bound ligand is complexed with adenine.

45. A composition, comprising a palladium(II)-bound ligand covalently bonded to a solid support through a spacer, said ligand portion of the palladium(II)-bound ligand comprising the sequence:

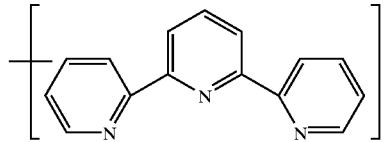

wherein the palladium(II)-bound ligand is complexed with thymine.

46. A composition as in claim 45, wherein the ligand is:

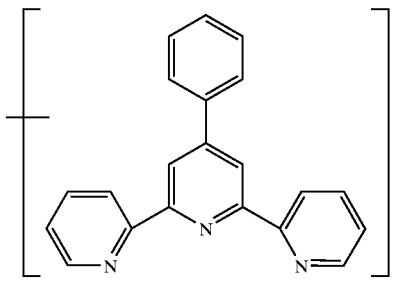

47. A composition, comprising a palladium(II)-bound ligand covalently bonded to a solid support through a spacer, said ligand portion of the palladium(II)-bound ligand comprising the sequence:

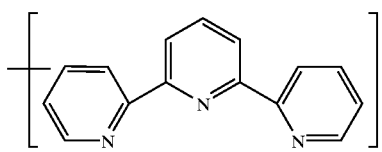

wherein the palladium(II)-bound ligand is complexed with uracil.

48. A composition as in claim 47, wherein the ligand is:

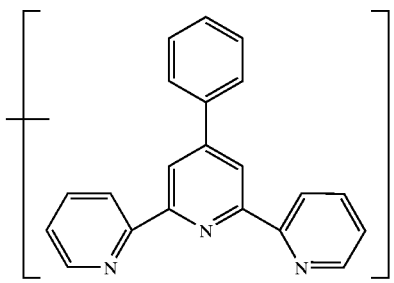

49. A composition, comprising a palladium(II)-bound ligand covalently bonded to a solid support through a spacer, said ligand portion of the palladium(II)-bound ligand comprising the sequence:

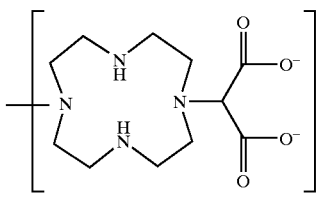

wherein the palladium(II)-bound ligand is completed with cytosine.

* * * * *